US007915281B2

(12) United States Patent
Moser et al.

(10) Patent No.: US 7,915,281 B2
(45) Date of Patent: *Mar. 29, 2011

(54) ISOXAZOLE, DIHYDROISOXAZOLE, AND OXADIAZOLE SUBSTITUTED IMIDAZO RING COMPOUNDS AND METHOD

(75) Inventors: William H. Moser, Saint Paul, MN (US); Joan T. Moseman, Saint Paul, MN (US); Tushar A. Kshirsagar, Saint Paul, MN (US); Philip D. Heppner, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 973 days.

This patent is subject to a terminal disclaimer.

(21) Appl. No.: 11/570,716

(22) PCT Filed: Jun. 17, 2005

(86) PCT No.: PCT/US2005/021570
§ 371 (c)(1),
(2), (4) Date: Dec. 15, 2006

(87) PCT Pub. No.: WO2006/065280
PCT Pub. Date: Jun. 22, 2006

(65) Prior Publication Data
US 2007/0287725 A1  Dec. 13, 2007

Related U.S. Application Data

(60) Provisional application No. 60/580,989, filed on Jun. 18, 2004, provisional application No. 60/665,520, filed on Mar. 25, 2005.

(51) Int. Cl.
*A61K 31/437* (2006.01)
*A61P 31/12* (2006.01)
*A61P 35/00* (2006.01)
*C07D 471/04* (2006.01)

(52) U.S. Cl. ............ 514/293; 514/303; 546/82; 546/118
(58) Field of Classification Search .................... 546/82, 546/118; 514/293, 303
See application file for complete search history.

(56) References Cited

U.S. PATENT DOCUMENTS

| | | |
|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster et al. |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |

(Continued)

FOREIGN PATENT DOCUMENTS

AU    2004220534 A1    9/2004

(Continued)

OTHER PUBLICATIONS

Zarubin et al., Russian Journal of Bioorganic Chemistry (Translation of Bioorganicheskaya Khimiya) (2002), 28(4), 284-292.*
International Search Report and Written Opinion for PCT/US2005/021570 mailed May 18, 2006.
International Preliminary Report on Patentability for PCT/US2005/021570 mailed Dec. 20, 2006.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.

(Continued)

*Primary Examiner* — D. Margaret Seaman
*Assistant Examiner* — Niloofar Rahmani

(57) ABSTRACT

Imidazo ring compounds, (e.g. imidazo[4,5-c]pyridine, imidazo[4,5-c]quinoline, 6,7,8,9-tetrahydro imidazo[4,5-c]quinoline, and imidazo[4,5-c]naphthyridine compounds) having an isoxazole, dihydroisoxazole, or oxadiazole substituent at the 1-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

9 Claims, No Drawings

U.S. PATENT DOCUMENTS

| | | | |
|---|---|---|---|
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |

| | | |
|---|---|---|
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1* | 11/2007 | Dellaria et al. .......... 514/253.03 |
| 2007/0259907 A1 | 11/2007 | Prince |
| 2007/0292456 A1 | 12/2007 | Hammerbeck et al. |
| 2008/0015184 A1* | 1/2008 | Kshirsagar et al. .......... 514/218 |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1* | 1/2009 | Lindstrom et al. .......... 514/227.8 |
| 2009/0023722 A1 | 1/2009 | Coleman et al. |
| 2009/0029988 A1 | 1/2009 | Kshirsagar et al. |
| 2009/0030030 A1* | 1/2009 | Bonk et al. .................... 514/293 |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1* | 4/2009 | Rice et al. .................. 514/228.5 |
| 2009/0105295 A1 | 4/2009 | Kshirsagar et al. |
| 2009/0124611 A1 | 5/2009 | Hays et al. |
| 2009/0163532 A1 | 6/2009 | Perman et al. |

| | | | |
|---|---|---|---|
| 2009/0163533 A1 | 6/2009 | Hays et al. | |
| 2009/0176821 A1 | 7/2009 | Kshirsagar et al. | |
| 2009/0240055 A1 | 9/2009 | Krepski et al. | |
| 2009/0253695 A1 | 10/2009 | Kshirsagar et al. | |
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |
| 2010/0240693 A1 | 9/2010 | Lundquist, Jr. et al. | |

FOREIGN PATENT DOCUMENTS

| | | |
|---|---|---|
| AU | 2004229478 A1 | 10/2004 |
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 A1 | 10/1990 |
| EP | 0 425 306 A2 | 5/1991 |
| EP | 0 510 260 A2 | 10/1992 |
| EP | 0 556 008 A1 | 8/1993 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 A1 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 1180156 A | 7/1989 |
| JP | 4066571 A | 3/1992 |
| JP | 4327587 A | 11/1992 |
| JP | 5286973 A | 11/1993 |
| JP | 9208584 A | 8/1997 |
| JP | 11222432 A | 8/1999 |
| JP | 2000247884 A | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO-02/36592 A1 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO-2005/018551 A2 | 3/2005 |
| WO | WO-2005/018555 A2 | 3/2005 |
| WO | WO-2005/018556 A2 | 3/2005 |
| WO | WO-2005/020999 A1 | 3/2005 |
| WO | WO-2005/023190 A2 | 3/2005 |
| WO | WO-2005/025614 A2 | 3/2005 |
| WO | WO-2005/029037 A2 | 3/2005 |
| WO | WO-2005/032484 A3 | 4/2005 |
| WO | WO-2005/041891 A2 | 5/2005 |
| WO | WO-2005/048933 A2 | 6/2005 |
| WO | WO-2005/048945 A2 | 6/2005 |
| WO | WO-2005/049076 A1 | 6/2005 |
| WO | WO-2005/051317 A2 | 6/2005 |
| WO | WO-2005/051324 A2 | 6/2005 |
| WO | WO-2005/054237 A1 | 6/2005 |
| WO | WO-2005/054238 A1 | 6/2005 |
| WO | WO-2005/065678 A1 | 7/2005 |
| WO | WO-2005/066169 A2 | 7/2005 |

| | | |
|---|---|---|
| WO | WO-2005/066170 A1 | 7/2005 |
| WO | WO-2005/066172 A1 | 7/2005 |
| WO | WO-2005/067500 A2 | 7/2005 |
| WO | WO-2005/076783 A2 | 8/2005 |
| WO | WO-2005/079195 A2 | 9/2005 |
| WO | WO-2005/094531 A2 | 10/2005 |
| WO | WO-2005/110013 A2 | 11/2005 |
| WO | WO-2005/123079 A2 | 12/2005 |
| WO | WO-2005/123080 A2 | 12/2005 |
| WO | WO-2006/004737 A2 | 1/2006 |
| WO | WO-2006/009826 A1 | 1/2006 |
| WO | WO-2006/009832 A1 | 1/2006 |
| WO | WO-2006/026760 A2 | 3/2006 |
| WO | WO-2006/028451 A1 | 3/2006 |
| WO | WO-2006/028545 A2 | 3/2006 |
| WO | WO-2006/028962 A2 | 3/2006 |
| WO | WO-2006/029115 A2 | 3/2006 |
| WO | WO-2006/031878 A2 | 3/2006 |
| WO | WO-2006/038923 A2 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

[No Author Listed] Encyclopedia of Pharmaceutical Technology. 2nd Ed. Marcel Dekker, Inc. 2002:856-60.

Agrawal et al., Synthetic agonists of Toll-like receptors 7, 8 and 9. Biochem Soc Trans. Dec. 2007;35(Pt 6):1461-7.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.

Akira et al., Toll-like receptors: critical proteins linking innate and acquired immunity. Nature Immunol. 2001;2(8):675-80.

Alexopoulou et al., Recognition of double-stranded RNA and activation of NF-kappaB by Toll-like receptor 3. Nature. Oct. 18, 2001;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Bachman et al., Synthesis of substituted quinolylamines. Derivatives of 4-amino-7-chloroquinoline. J Org Chem. 1950;15(6):1278-84.

Baffis et al., Use of interferon for prevention of hepatocellular carcinoma in cirrhotic patients with hepatitis B or hepatitis C virus infection. Ann Intern Med. Nov. 2, 1999;131(9):696-701.

Baker et al., Oral infection with Porphyromonas gingivalis and induced alveolar bone loss in immunocompetent and severe combined immunodeficient mice. Arch Oral Biol. Dec. 1994;39(12):1035-40.

Baldwin et al., Amino Acid Synthesis via Ring Opening of N-Sulphonyl Aziridine-2-Carboxylate Esters with Organometallic Reagents. Tetrahedron. 1993;49:6309-30.

Baranov et al., Imidazo[4-5c]quinolines. In Chemical Abstracts. 1976;85:637. Abstract 94362z.

Bártová et al., Th1 and Th2 cytokine profile in patients with early onset periodontitis and their healthy siblings. Mediators Inflamm. 2000;9(2):115-20.

Beck et al., Dental Infections and Atherosclerosis. Am Heart J. 1999;13:528-33.

Beckett et al., Configurational Studies in Synthetic Analgesics: the Synthesis of (−)-Methadone from D-(−)- Alanine. J Chem Soc. 1957;1:858-61.

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al, Some Methylhydrazonium Salts; An Improved Synthesis of Tetramethylhydrazine. J Am Chem Soc. 1956;78:2467-68.

Berenyi et al., Ring transformation of condensed dihyrdo-as-triazines. J Heterocyclic Chem. 1981;18:1537-40.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

Beutner et at, Treatment of genital warts with an immune-response modifier (imiquimod). J Am Acad Dermatol. Feb. 1998:38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et at., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Brennan et al., Automated bioassay of interferons in microtest plates. Biotechniques. Jun./Jul. 1983(1):78-82.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidypmethyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chollet et al., Development of a topically active imiquimod formulation. Pharm Dev Technol. Jan. 1999;4(1):35-43.

Chuang et al., Toll-like receptor 9 mediates CpG-DNA signaling. J Leukoc Biol. Mar. 2002;71(3): 538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3 + 2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et at., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Ilno et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretionecanol and Lupinine. J Org Chem. 1982;47:230-33.

Izumi et al., 1H-Imidazo[4,5-c]quinoline derivatives as novel potent TNF-alpha suppressors: synthesis and structure-activity relationship of 1-, 2-and 4-substituted 1H-imidazo[4,5-c]quinolines or 1H-imidazo[4,5-c]pyridines. Bioorg Med Chem. Jun. 12, 2003;11(12):2541-50.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jain et al., Chemical and pharmacological investigations of some omega-substituted alkylamino-3-aminopyridines. J Med Chem. Jan. 1968;11(1):87-92.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some ò -nitrokenes. J Am Chem Soc. 1947;69:2271-2275.

Kornman, Host modulation as a therapeutic strategy in the treatment of periodontal disease. Clin Infect Dis. Mar. 1999;28(3):520-6.

Kourafalos et at., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γδ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of Lactococcus lactis. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (Loxosceles reclusa) on human neutrophils. Toxicon. 1977;15(5):423-7.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of $N^{\alpha}$-Benzyloxycarbonyl-$_L$-Ornithine and of $N^{\alpha}$-(9-Fluorenylmethoxy)Carbonyl-$_L$-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stifle coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activity Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998;52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1 beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel of al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al, Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science.Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, Loxosceles reclusa. Lab invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR -7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Testerman et al., Cytokine induction by the immunomodulators imiquimod and S-27609. J Leukoc Biol. Sep. 1995;58(3):365-72.

Thesing et al., [Darstellung and Eigenschaften des $\Delta^1$-Pyrrolin-N-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (Trail) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells-the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Tray Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

ISOXAZOLE, DIHYDROISOXAZOLE, AND OXADIAZOLE SUBSTITUTED IMIDAZO RING COMPOUNDS AND METHOD

CROSS REFERENCE TO RELATED APPLICATIONS

This application is the National Stage of International Application No. PCT/US2005/021570, filed Jun. 17, 2005, which claims priority to U.S. Provisional Application Ser. No. 60/665,520, filed Mar. 25, 2005, and U.S. Provisional Application Ser. No. 60/580,989, filed Jun. 18, 2004, both of which are incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

It has now been found that compounds of Formula I are useful as immune response modifiers. The present invention, therefore, provides a new class of immune response modifying compounds of the following Formula I:

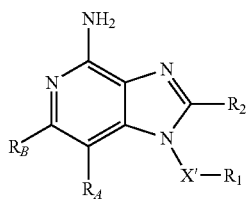

I wherein X', $R_1$, $R_A$, $R_B$, and $R_2$ are as defined below.

The compounds of Formula I are useful as immune response modifiers due to their ability to induce cytokine biosynthesis (e.g., induce the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I:

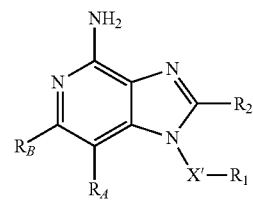

I as well as more specific compounds of the following Formulas II through VIII, IXa, IXb, IXc, and IXd:

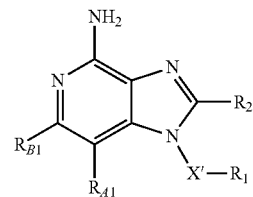

II

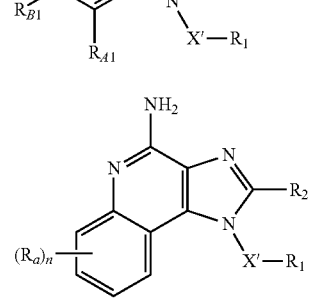

III

-continued

IV
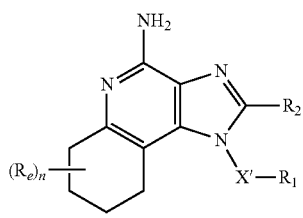

V
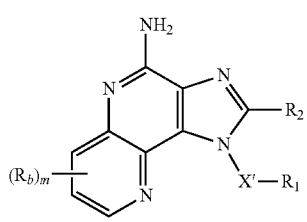

VI
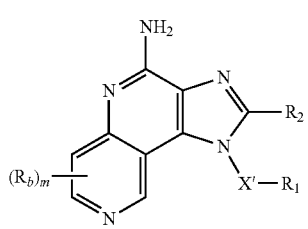

VII
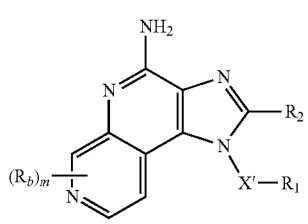

VIII
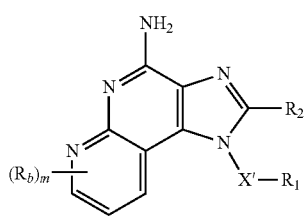

IXa
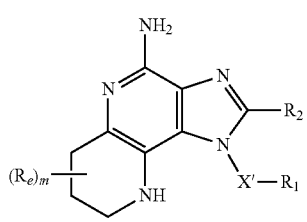

IXb
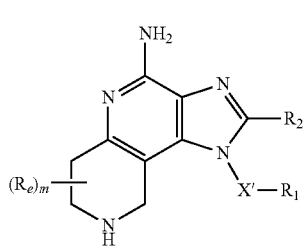

-continued

IXc
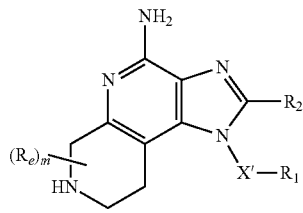

IXd
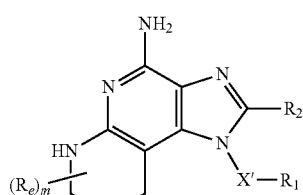

and intermediates of the following Formula X:

X
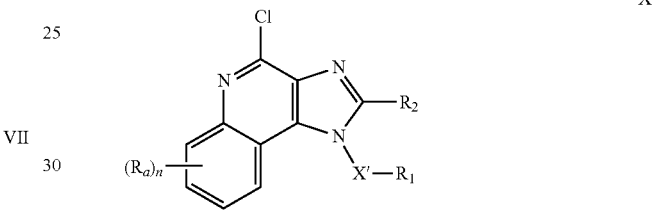

wherein X', $R_1$, $R_A$, $R_B$, $R_{A1}$, $R_{B1}$, $R_a$, $R_b$, $R_e$, $R_2$, m, and n are as defined below.

In one embodiment, the present invention provides a compound of Formula I:

I
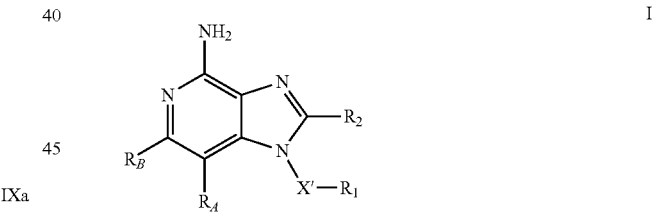

wherein:
X' is selected from the group consisting of —CH($R_9$)—, —CH($R_9$)-alkylene-, and —CH($R_9$)-alkenylene-;
$R_1$ is selected from the group consisting of:

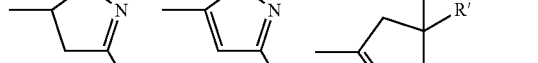
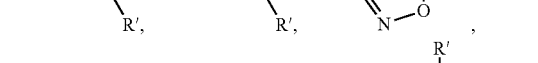
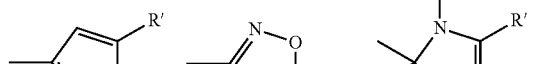
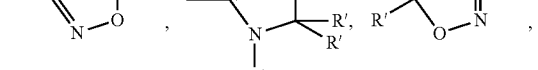

-continued

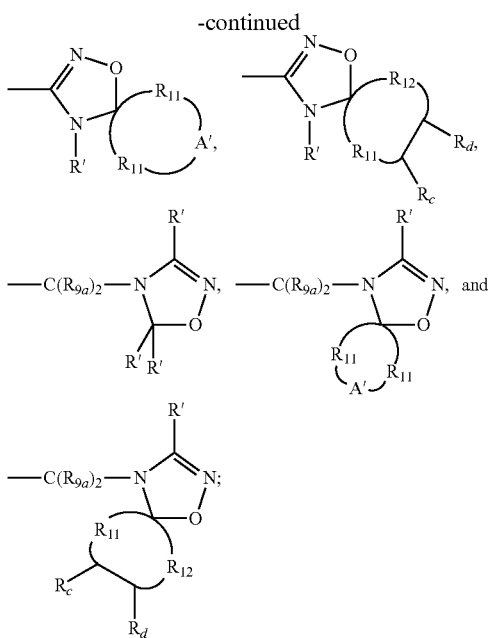

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;

R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;

R$_{11}$ is C$_{1-6}$ alkylene or C$_{2-6}$ alkenylene, wherein the alkylene or alkenylene is optionally interrupted by one heteroatom;

R$_{12}$ is selected from the group consisting of a bond, C$_{1-5}$ alkylene, and C$_{2-5}$ alkenylene, wherein the alkylene or alkenylene is optionally interrupted by one heteroatom;

wherein the total number of atoms in the ring which includes R$_{11}$ or R$_{12}$ is 4 to 9;

A' is selected from the group consisting of —O—, —S(O)$_{0-2}$—, —N(-Q-R$_4$)—, and —C(R$_{9a}$)$_2$—;

R$_A$ and R$_B$ are each independently selected from the group consisting of:
hydrogen,
halogen,
alkyl,
alkenyl,
alkoxy,
alkylthio, and
—N(R$_9$)$_2$;

or R$_A$ and R$_B$ taken together form either a fused aryl ring that is unsubstituted or substituted by one or more R$_a$ groups, or a fused 5 to 7 membered saturated ring that is unsubstituted or substituted by one or more R$_e$ groups;

or R$_A$ and R$_B$ taken together form a fused heteroaryl or 5 to 7 membered saturated ring containing one heteroatom selected from the group consisting of N and S, wherein the heteroaryl ring is unsubstituted or substituted by one or more R$_b$ groups, and the 5 to 7 membered saturated ring is unsubstituted or substituted by one or more R$_e$ groups;

R$_a$ is selected from the group consisting of halogen, alkyl, haloalkyl, alkoxy, and —N(R$_9$)$_2$;

R$_b$ is selected from the group consisting of halogen, hydroxy, alkyl, haloalkyl, alkoxy, and —N(R$_9$)$_2$;

R$_e$ is selected from the group consisting of halogen, hydroxy, alkyl, alkenyl, haloalkyl, alkoxy, alkylthio, and —N(R$_9$)$_2$;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

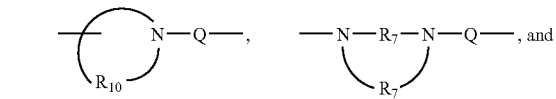

-continued

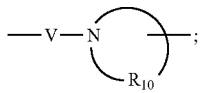

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

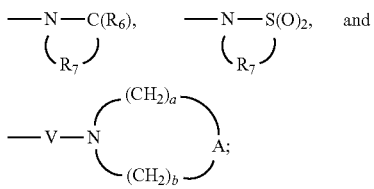

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, and arylalkylenyl;
$R_9$ is selected from the group consisting of hydrogen and alkyl;
$R_{9a}$ is selected from the group consisting of hydrogen and $C_{1-4}$ alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, and —S(O)$_2$—N(R$_8$)—;
V is selected from the group consisting of —C(R$_6$)—, —O—C(R$_6$)—, and —S(O)$_2$—; and
a and b are each independently an integer from 1 to 6 with the proviso that a+b is ≦7;
or a pharmaceutically acceptable salt thereof.

In one embodiment, the present invention provides a compound of Formula II:

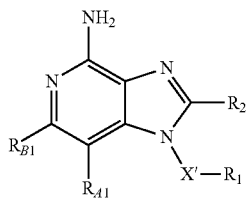

II wherein:
X' is selected from the group consisting of —CH(R$_9$)—, —CH(R$_9$)-alkylene-, and —CH(R$_9$)-alkenylene-;
R₁ is selected from the group consisting of:

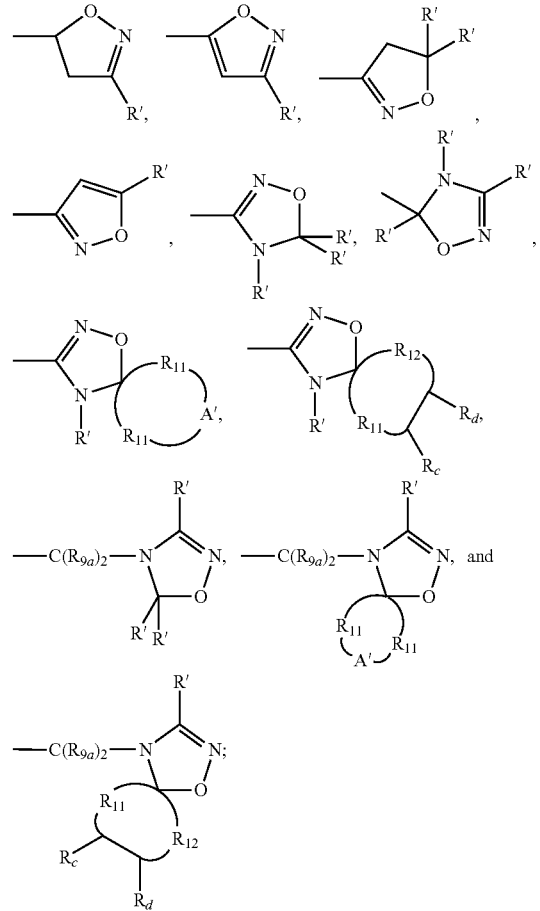

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen, nitrile,
nitro,
aryl,
heteroaryl,
heterocyclyl,
aryloxy,
arylalkyleneoxy,
—C(O)—O-alkyl,
—C(O)—N($R_8$)$_2$,
—N($R_8$)—C(O)-alkyl,
—O—(CO)-alkyl, and
—C(O)-alkyl;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

wherein the total number of atoms in the ring which includes $R_{11}$ or $R_{12}$ is 4 to 9;

A' is selected from the group consisting of —O—, —S(O)$_{0-2}$—, —N(-Q-$R_4$)—, and —C($R_{9a}$)$_2$—;

$R_{A1}$ and $R_{B1}$ are each independently selected from the group consisting of:
hydrogen,
halogen,
alkyl,
alkenyl,
alkoxy,
alkylthio, and
—N($R_9$)$_2$;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

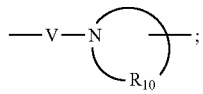, —N—$R_7$—N—Q—, and

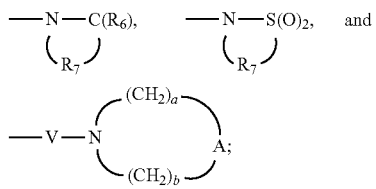

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

—N—C($R_6$),    —N—S(O)$_2$,    and
   |                |
   $R_7$            $R_7$ —V—N(—(CH$_2$)$_a$—)(—(CH$_2$)$_b$—)A;

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, and arylalkylenyl;
$R_9$ is selected from the group consisting of hydrogen and alkyl;
$R_{9a}$ is selected from the group consisting of hydrogen and $C_{1-4}$ alkyl;
$R_{10}$ is $C_{3-8}$ alkylene;
A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$)—, —S(O)$_2$—, and —S(O)$_2$—N($R_8$)—;
V is selected from the group consisting of —C($R_6$)—, —O—C($R_6$)—, and —S(O)$_2$—; and
a and b are each independently an integer from 1 to 6 with the proviso that a+b is ≦7;
or a pharmaceutically acceptable salt thereof.

In one embodiment, the present invention provides a compound of Formula III:

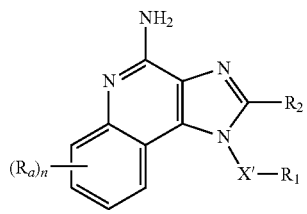

III wherein:

X' is selected from the group consisting of —CH(R$_9$)—, —CH(R$_9$)-alkylene-, and —CH(R$_9$)-alkenylene-;

R$_1$ is selected from the group consisting of:

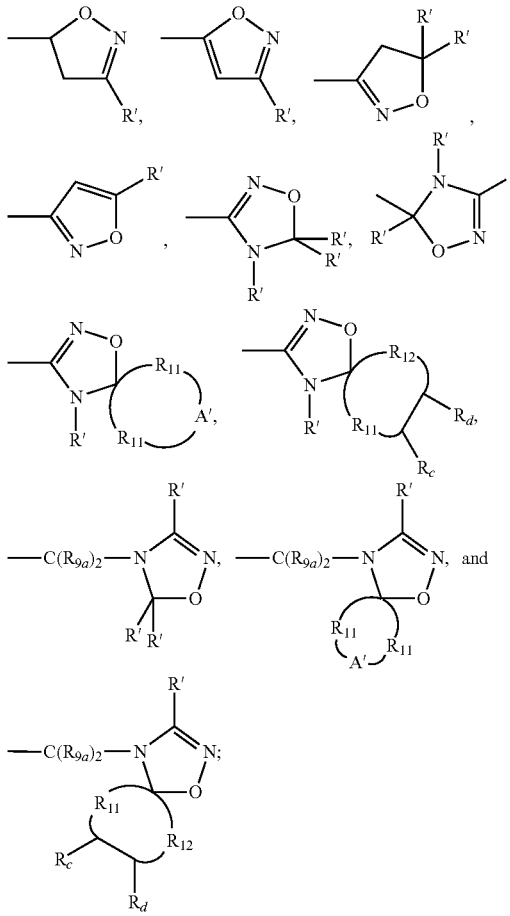

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;

R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;

R$_{11}$ is C$_{1-6}$ alkylene or C$_{2-6}$ alkenylene, wherein the alkylene or alkenylene is optionally interrupted by one heteroatom;

R$_{12}$ is selected from the group consisting of a bond, C$_{1-5}$ alkylene, and C$_{2-5}$ alkenylene, wherein the alkylene or alkenylene is optionally interrupted by one heteroatom;

wherein the total number of atoms in the ring which includes R$_{11}$ or R$_{12}$ is 4 to 9;

A' is selected from the group consisting of —O—, —S(O)$_{0-2}$—, —N(-Q-R$_4$)—, and —C(R$_{9a}$)$_2$—;

R$_a$ is selected from the group consisting of halogen, alkyl, haloalkyl, alkoxy, and —N(R$_9$)$_2$;

n is an integer from 0 to 4;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

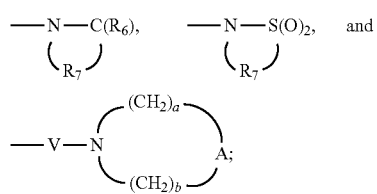

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, and arylalkylenyl;

$R_9$ is selected from the group consisting of hydrogen and alkyl;

$R_{9a}$ is selected from the group consisting of hydrogen and $C_{1-4}$ alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, and —S(O)$_2$—N(R$_8$)—;

V is selected from the group consisting of —C(R$_6$)—, —O—C(R$_6$)—, and —S(O)$_2$—; and a and b are each independently an integer from 1 to 6 with the proviso that a+b is ≦7;

or a pharmaceutically acceptable salt thereof.

In one embodiment, the present invention provides a compound of Formula IV:

IV

[Structure of Formula IV with NH$_2$, $(R_e)_n$, $R_2$, $X'$—$R_1$]

wherein:

X' is selected from the group consisting of —CH(R$_9$)—, —CH(R$_9$)-alkylene-, and —CH(R$_9$)-alkenylene-;

$R_1$ is selected from the group consisting of:

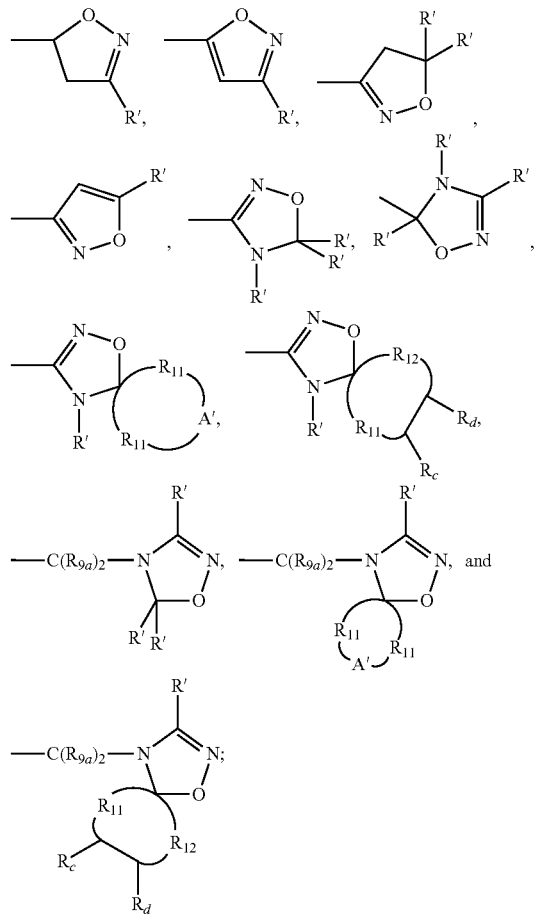

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro, aryl,
heteroaryl,
heterocyclyl,
aryloxy,
arylalkyleneoxy,
—C(O)—O-alkyl,
—C(O)—N($R_8$)$_2$,
—N($R_8$)—C(O)-alkyl,
—O—(CO)-alkyl, and
—C(O)-alkyl;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

wherein the total number of atoms in the ring which includes $R_{11}$ or $R_{12}$ is 4 to 9;

A' is selected from the group consisting of —O—, —S(O)$_{0-2}$—, —N(-Q-$R_4$)—, and —C($R_{9a}$)$_2$—;

$R_e$ is selected from the group consisting of halogen, hydroxy, alkyl, alkenyl, haloalkyl, alkoxy, alkylthio, and —N($R_9$)$_2$;

n is an integer of 0 to 4;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

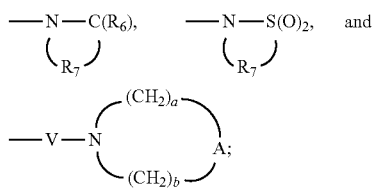

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$$-N-C(R_6),\quad -N-S(O)_2,\quad\text{and}$$
$$\phantom{xxx}\underset{R_7}{\underbrace{\phantom{xxxx}}}\quad\phantom{xx}\underset{R_7}{\underbrace{\phantom{xxxx}}}$$

$$-V-N\begin{pmatrix}(CH_2)_a\\ (CH_2)_b\end{pmatrix}A;$$

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, and arylalkylenyl;
$R_9$ is selected from the group consisting of hydrogen and alkyl;
$R_{9a}$ is selected from the group consisting of hydrogen and $C_{1-4}$ alkyl;
$R_{10}$ is $C_{3-8}$ alkylene;
A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$)—, —S(O)$_2$—, and —S(O)$_2$—N($R_8$)—;
V is selected from the group consisting of —C($R_6$)—, —O—C($R_6$)—, and —S(O)$_2$—; and
a and b are each independently an integer from 1 to 6 with the proviso that a+b is ≦7;
or a pharmaceutically acceptable salt thereof.

In one embodiment, the present invention provides a compound selected from the group consisting Formulas V, VI, VII, and VIII:

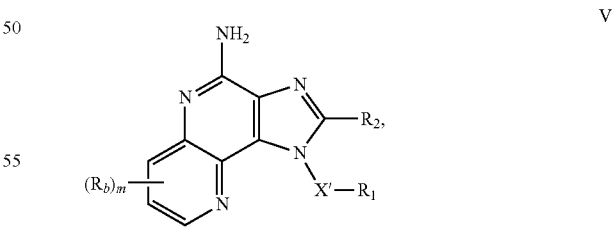

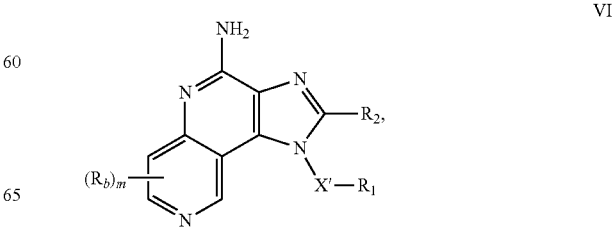

-continued

VII

[Chemical structure: imidazo-naphthyridine with NH2, R2, X'-R1, (Rb)m substituents]

VIII

[Chemical structure: imidazo-naphthyridine with NH2, R2, X'-R1, (Rb)m substituents]

wherein:
X' is selected from the group consisting of —CH(R$_9$)—, —CH(R$_9$)-alkylene-, and —CH(R$_9$)-alkenylene-;
R$_1$ is selected from the group consisting of:

[Chemical structures showing various isoxazoline, isoxazole, and oxadiazoline ring systems with R' substituents]

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;

R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;

R$_{11}$ is C$_{1-6}$ alkylene or C$_{2-6}$ alkenylene, wherein the alkylene or alkenylene is optionally interrupted by one heteroatom;

R$_{12}$ is selected from the group consisting of a bond, C$_{1-5}$ alkylene, and C$_{2-5}$ alkenylene, wherein the alkylene or alkenylene is optionally interrupted by one heteroatom;

wherein the total number of atoms in the ring which includes R$_{11}$ or R$_{12}$ is 4 to 9;

A' is selected from the group consisting of —O—, —S(O)$_{0-2}$—, —N(-Q-R$_4$)—, and —C(R$_{9a}$)$_2$—;

R$_b$ is selected from the group consisting of halogen, hydroxy, alkyl, haloalkyl, alkoxy, and —N(R$_9$)$_2$;

m is an integer from 0 to 3;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—, —O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

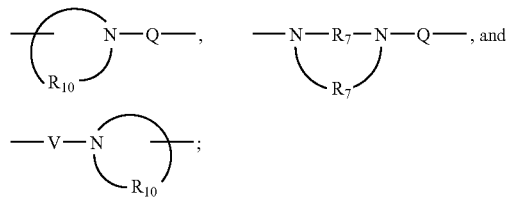

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

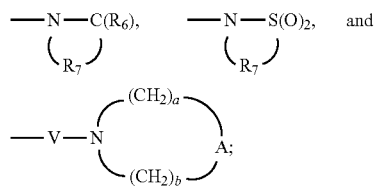

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, and arylalkylenyl;
R$_9$ is selected from the group consisting of hydrogen and alkyl;
R$_{9a}$ is selected from the group consisting of hydrogen and C$_{1-4}$ alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, and —S(O)$_2$—N(R$_8$)—;
V is selected from the group consisting of —C(R$_6$)—, —O—C(R$_6$)—, and —S(O)$_2$—; and
a and b are each independently an integer from 1 to 6 with the proviso that a+b is ≦7;
or a pharmaceutically acceptable salt thereof.

In one embodiment, the present invention provides a compound selected from the group consisting Formulas IXa, IXb, IXc, and IXd:

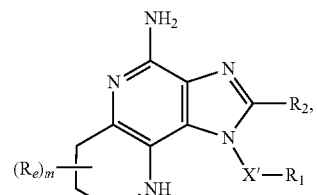
IXa

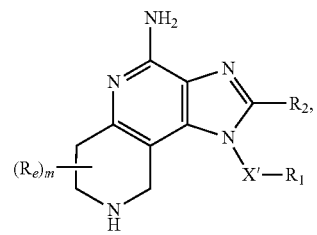
IXb

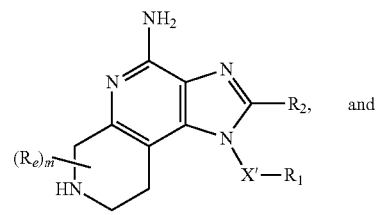
IXc and

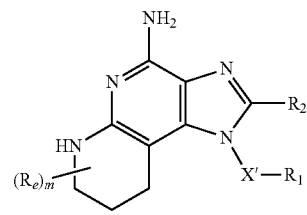
IXd wherein:
X' is selected from the group consisting of —CH(R$_9$)—, —CH(R$_9$)-alkylene-, and —CH(R$_9$)-alkenylene-;
R$_1$ is selected from the group consisting of:

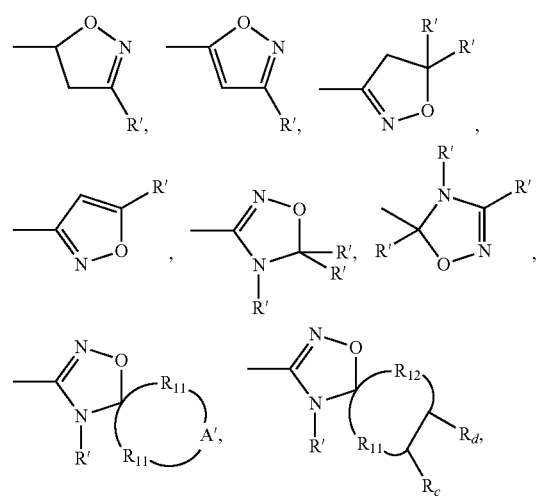

-continued $$-C(R_{9a})_2-N\underset{R'\ R'}{\overset{R'}{\underset{|}{\bigcirc}}}N, \quad -C(R_{9a})_2-N\underset{R_{11}\overset{A'}{\smile}R_{11}}{\overset{R'}{\underset{|}{\bigcirc}}}N, \text{ and}$$

$$-C(R_{9a})_2-N\underset{R_c\overset{R_{11}}{\smile}R_{12}\overset{|}{\underset{R_d}{\smile}}}{\overset{R'}{\underset{|}{\bigcirc}}}N;$$

R' is selected from the group consisting of:
hydrogen,
alkyl, alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—$N(R_8)_2$,
—$N(R_8)$—C(O)-alkyl,
—O—(CO)-alkyl, and
—C(O)-alkyl;

$R_c$ and $R_d$ are independently selected from the group consisting of hydrogen, halogen, hydroxy, alkyl, alkenyl, aryl, haloalkyl, alkoxy, alkylthio, and —$N(R_9)_2$; or $R_c$ and $R_d$ can join to form a fused aryl ring or fused 5-10 membered heteroaryl ring containing one to four heteroatoms;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

wherein the total number of atoms in the ring which includes $R_{11}$ or $R_{12}$ is 4 to 9;

A' is selected from the group consisting of —O—, —$S(O)_{0-2}$—, —N(-Q-$R_4$)—, and —$C(R_{9a})_2$—;

$R_e$ is selected from the group consisting of halogen, hydroxy, alkyl, alkenyl, haloalkyl, alkoxy, alkylthio, and —$N(R_9)_2$;

m is an integer from 0 to 3;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—, $$-\underset{R_{10}}{\overset{\frown}{\underset{\smile}{N}}}-Q-, \quad -N-R_7-\underset{R_7}{\overset{\frown}{\underset{\smile}{N}}}-Q-, \text{ and}$$

$$-V-\underset{R_{10}}{\overset{\frown}{\underset{\smile}{N}}};$$

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$$-\underset{R_7}{\overset{\frown}{\underset{\smile}{N}}}-C(R_6), \quad -\underset{R_7}{\overset{\frown}{\underset{\smile}{N}}}-S(O)_2, \quad \text{and}$$

-continued

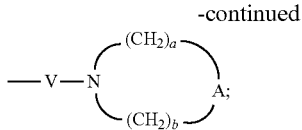

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, and arylalkylenyl;
$R_9$ is selected from the group consisting of hydrogen and alkyl;
$R_{9a}$ is selected from the group consisting of hydrogen and $C_{1-4}$ alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, and —S(O)$_2$—N(R$_8$)—;
V is selected from the group consisting of —C(R$_6$)—, —O—C(R$_6$)—, and —S(O)$_2$—; and
a and b are each independently an integer from 1 to 6 with the proviso that a+b is ≦7;
or a pharmaceutically acceptable salt thereof.

In one embodiment, the present invention provides an intermediate compound of Formula X:

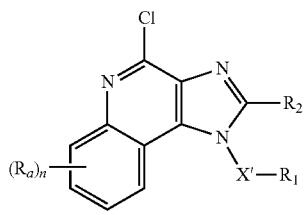

wherein:
X' is selected from the group consisting of —CH(R$_9$)—, —CH(R$_9$)-alkylene-, and —CH(R$_9$)-alkenylene-;
R$_1$ is selected from the group consisting of:

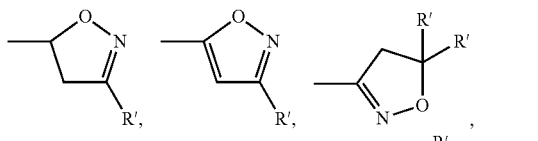

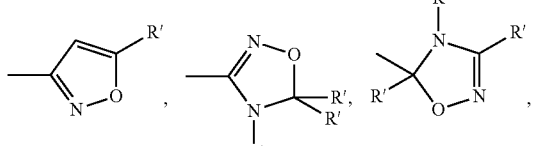

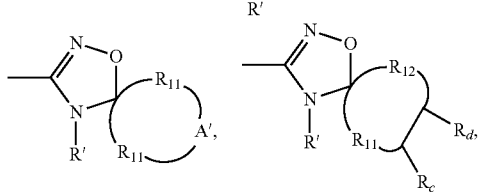

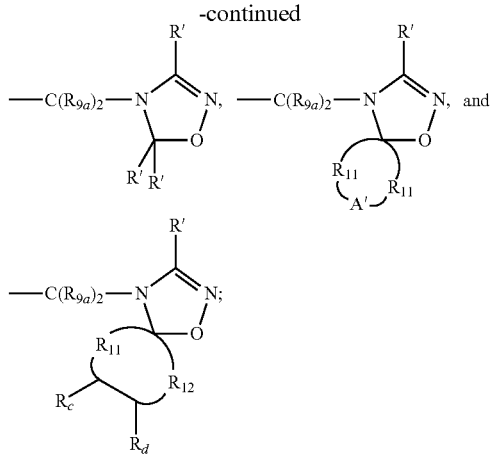

R' is selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;
R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;
R$_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

wherein the total number of atoms in the ring which includes $R_{11}$ or $R_{12}$ is 4 to 9;

A' is selected from the group consisting of —O—, —S(O)$_{0-2}$—, —N(-Q-R$_4$)—, and —C(R$_{9a}$)$_2$—;

$R_a$ is selected from the group consisting of halogen, alkyl, haloalkyl, alkoxy, and —N(R$_9$)$_2$;

n is an integer from 0 to 4;

$R_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—, —

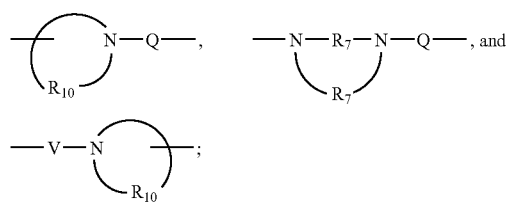

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, halo alkyl, halo alkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

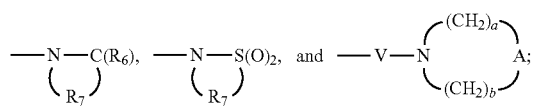

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, and arylalkylenyl;

$R_9$ is selected from the group consisting of hydrogen and alkyl;

$R_{9a}$ is selected from the group consisting of hydrogen and $C_{1-4}$ alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, and —S(O)$_2$—N(R$_8$)—;

V is selected from the group consisting of —C(R$_6$)—, —O—C(R$_6$)—, and —S(O)$_2$—; and a and b are each independently an integer from 1 to 6 with the proviso that a+b is ≤7;

or a pharmaceutically acceptable salt thereof.

For certain embodiments, there is provided a compound (which is a prodrug) of the Formula I-1:

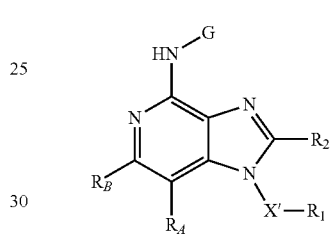

I-1 wherein:

G is selected from the group consisting of:
—C(O)—R",
α-aminoacyl,
α-aminoacyl-α-aminoacyl,
—C(O)—O—R",
—C(O)—N(R''')R",
—C(=NY')—R",
—CH(OH)—C(O)—OY',
—CH(OC$_{1-4}$ alkyl)Y$_0$,
—CH$_2$Y$_1$, and
—CH(CH$_3$)Y$_1$;

R" and R''' are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R''' can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

Y$_0$ is selected from the group consisting of $C_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl;

Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl; and $R_A$, $R_B$, X', $R_1$, and $R_2$ are as defined in Formula I above;

or a pharmaceutically acceptable salt thereof.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached. In another example, hydroxyalkylenyl, haloalkylenyl, and haloalkyleneoxy have the same meaning as hydroxyalkyl, haloalkyl, and haloalkoxy, respectively.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N. Examples of fused heteroaryl rings include pyrido and thieno.

The term "fused 5 to 7 membered saturated ring" includes rings which are fully saturated except for the bond where the ring is fused, for example a cyclohexene ring and a tetrahydropyridine ring (when one nitrogen atom is present).

When a group (or substituent or variable) is present more than once in any Formula described herein, each group (or substituent or variable) is independently selected, whether explicitly stated or not. For example, for the formula —C(O)—N($R_8$)$_2$— each $R_8$ group is independently selected. In another example, when two R' groups are present, each R' group is independently selected. In a further example, when more than one R' group is present and each R' group contains one or more $R_8$ groups, then each R' group is independently selected, and each $R_8$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., X', $R_1$, R', $R_2$, X, Y, $R_a$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I or I-1, $R_A$ and $R_B$ taken together form a fused aryl ring that is unsubstituted or substituted by one or more $R_a$ groups. For certain of these embodiments, the fused aryl ring is unsubstituted.

For certain embodiments of Formula I or I-1, $R_A$ and $R_B$ taken together form a fused 5 to 7 membered saturated ring that is unsubstituted or substituted by one or more $R_e$ groups. In certain of these embodiments the ring is unsubstituted.

For certain embodiments of Formula I or I-1, $R_A$ and $R_B$ taken together form a fused heteroaryl ring that is unsubstituted or substituted by one or more $R_b$ groups. For certain of these embodiments the fused heteroaryl ring is unsubstituted. In certain embodiments, the ring is pyrido.

For certain embodiments of Formula I or I-1, $R_A$ and $R_B$ taken together form a fused 5 to 7 membered saturated ring containing one heteroatom selected from the group consisting of N and S, wherein the ring is unsubstituted or substituted by one or more $R_e$ groups. For certain of these embodiments, the ring is unsubstituted. In certain embodiments, the ring is tetrahydropyrido. In certain of these embodiments, the ring is

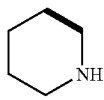

wherein the highlighted bond indicates the position where the ring is fused.

For certain embodiments of Formula II, $R_{A1}$ and $R_{B1}$ are independently selected from the group consisting of hydrogen and alkyl.

For certain embodiments of Formula II, $R_{A1}$ and $R_{B1}$ are each methyl.

For certain embodiments, including any one of the above embodiments of Formula III, Formula IV, or Formula X, n is 0.

For certain embodiments, the compound selected from the group consisting of Formulas V, VI, VII, and VIII, or a pharmaceutically acceptable salt thereof is the compound of Formula V or a pharmaceutically acceptable salt thereof.

For certain embodiments, the compound selected from the group consisting of Formulas IXa, IXb, IXc, and IXd, or a pharmaceutically acceptable salt thereof is the compound of Formula IXa or a pharmaceutically acceptable salt thereof.

For certain embodiments, including any one of the above embodiments of Formulas V, VI, VII, VIII, IXa, IXb, IXc, and/or IXd, m is 0.

For certain embodiments, including any one of the above embodiments of Formulas I, I-1, II, III, IV, V, VI, VII, VIII, X, or IXa-d, X' is $C_{1-4}$ alkylene. For certain of these embodiments, X' is —CH$_2$—. For certain of these embodiments, X' is —CH$_2$CH$_2$—.

For certain embodiments, including any one of the above embodiments of Formulas I, I-1, II, III, IV, V, VI, VII, VIII, X, or IXa-d, $R_1$ is selected from the group consisting of:

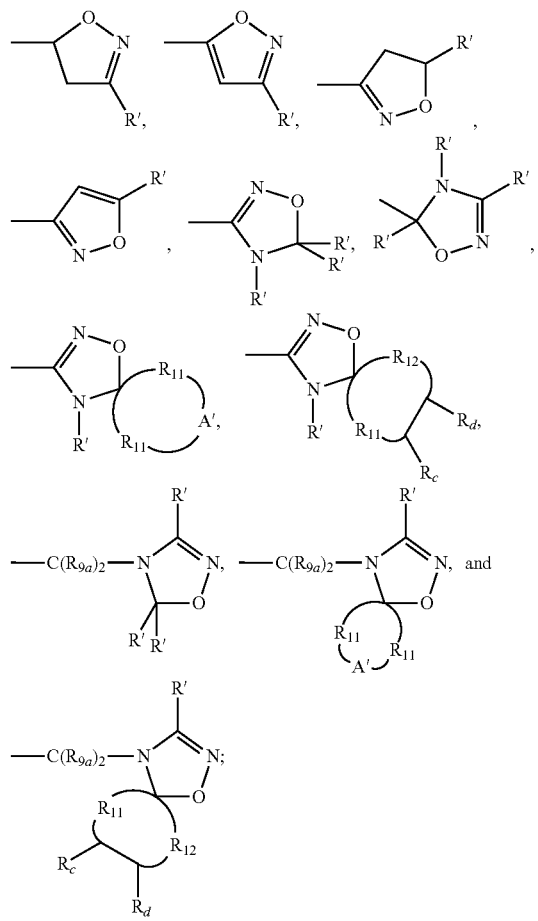

and $R_8$ is selected from the group consisting of hydrogen, alkyl, alkoxyalkylenyl, and arylalkylenyl.

For certain embodiments, including any one of the above embodiments of Formulas I, I-1, II, III, IV, V, VI, VII, VIII, X, or IXa-d which does not exclude this definition, $R_1$ is selected from the group consisting of:

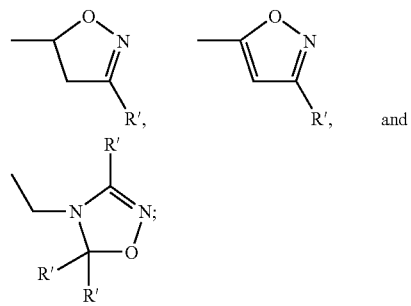

each $R_a$ is independently selected from the group consisting of fluorine, alkyl, haloalkyl, alkoxy, and —N(R$_9$)$_2$; and each $R_8$ is independently selected from the group consisting of hydrogen, alkyl, alkoxyalkylenyl, and arylalkylenyl.

For certain embodiments, including any one of the above embodiments of Formulas I, I-1, II, III, IV, V, VI, VII, VIII, X, or IXa-d which does not exclude this definition, $R_1$ is selected from the group consisting of

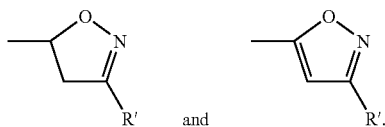

For certain of these embodiments, R₁ is

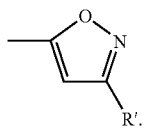

For certain embodiments, including any one of the above embodiments of Formulas I, I-1, II, III, IV, V, VI, VII, VIII, X, or IXa-d which does not exclude this definition, R₁ is selected from the group consisting of

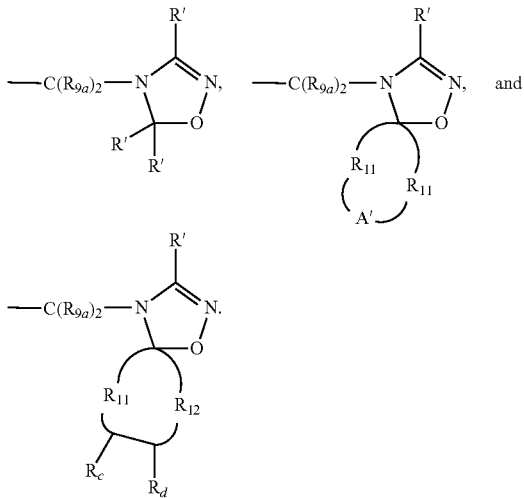

For certain of these embodiments, R_{9a} is hydrogen. For certain of these embodiments, R₁ is

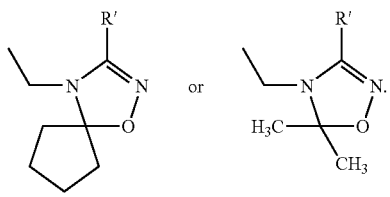

For certain of these embodiments, R₁ is

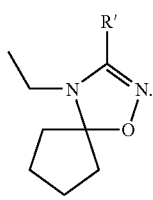

For certain embodiments, including any one of the above embodiments of Formulas I, I-1, II, III, IV, V, VI, VII, VIII, X, or Ixa-d which does not exclude this definition, R₁ is

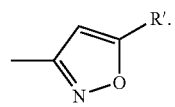

For certain embodiments, including any one of the above embodiments of Formulas I, I-1, II, III, IV, V, VI, VII, VIII, X, or IXa-d, R' is selected from the group consisting of alkyl, aryl, and heteroaryl, each of which is unsubstituted or substituted by one or more substituents selected from the group consisting of alkyl, alkoxy, halogen, and haloalkyl. For certain of these embodiments, R' is selected from the group consisting of methyl; butyl; phenyl which is unsubstituted or substituted by one or more substituents selected from the group consisting of fluorine and trifluoromethyl; and 3-pyridyl. For certain of these embodiments, R' is selected from the group consisting of methyl; phenyl which is unsubstituted or substituted by one or more substituents selected from the group consisting of fluorine and trifluoromethyl; and 3-pyridyl.

For certain embodiments, including any one of the above embodiments of Formulas I, I-1, II, III, IV, V, VI, VII, VIII, X, or IXa-d, R₂ is hydrogen; alkoxyalkylenyl; hydroxyalkylenyl; haloalkylenyl; heterocyclylalkylenyl that is unsubstituted or substituted by one or more substituents selected from the group consisting of methyl, hydroxy, hydroxymethyl, and dimethylamino; —R₄; —X—R₄; or —X—Y—R₄; wherein X is $C_{1-2}$ alkylene optionally terminated by heterocyclylene;

Y is —S(O)$_{0-2}$—, —S(O)$_2$—N(R₈)—, —C(R₆)—, —C(R₆)—O—, —O—C(R₆)—, —O—C(O)—O—, —N(R₈)-Q-, —C(R₆)—N(R₈)—, —O—C(R₆)—N(R₈)—, or —C(R₆)—N(OR₉)—; wherein R₈ is selected from the group consisting of hydrogen, alkyl, arylalkylenyl, and hydroxyalkylenyl; and R₄ is alkyl that is unsubstituted or substituted by one or more substituents selected from the group consisting of hydroxy and cyano, aryl; or heterocyclyl that is unsubstituted or substituted by alkyl with the proviso that when Y is —C(R₆)—O— or —C(R₆)—N(R₈)—, then R₄ may also be hydrogen.

For certain embodiments, including any one of the above embodiments of Formulas I, I-1, II, III, IV, V, VI, VII, VIII, X, or IXa-d, R₂ is hydrogen, alkoxyalkylenyl, hydroxyalkylenyl, —R₄, —X—R₄, or —X—Y—R₄; wherein X is $C_{1-2}$ alkylene;

Y is —S(O)$_{0-2}$—, —S(O)$_2$—N(R₈)—, —C(R₆)—, —C(R₆)—O—, —O—C(R₆)—, —O—C(O)—O—, —N(R₈)-Q-, —C(R₆)—N(R₈)—, —O—C(R₆)—N(R₈)—, or —C(R₆)—N(OR₉)—; and R₄ is alkyl.

For certain of these embodiments, R₈ is selected from the group consisting of hydrogen, alkyl, and arylalkylenyl.

For certain embodiments, including any one of the above embodiments of Formulas I, I-1, II, III, IV, V, VI, VII, VIII, X, or IXa-d, R₂ is hydrogen, $C_{1-4}$ alkyl, $C_{1-4}$ alkyl-O—$C_{1-4}$ alkylenyl, or hydroxy$C_{1-4}$ alkylenyl. For certain of these embodiments, R₂ is methyl, ethyl, n-propyl, n-butyl, ethoxymethyl, 2-methoxyethyl, hydroxymethyl, or 2-hydroxyethyl.

For certain embodiments, including any one of the above embodiments of Formulas I, I-1, II, III, IV, V, VI, VII, VIII, X, or IXa-d which does not exclude this definition, $R_2$ is methyl, ethyl, n-propyl, n-butyl, ethoxymethyl, 2-methoxyethyl, hydroxymethyl, 2-hydroxyethyl, or fluoromethyl.

For certain embodiments, the present invention provides a pharmaceutical composition comprising a therapeutically effective amount of a compound or salt of any one of the above embodiments of Formulas I, I-1, II, III, IV, V, VI, VII, VIII, and IXa-d and a pharmaceutically acceptable carrier.

For certain embodiments, the present invention provides a method of inducing cytokine biosynthesis in an animal comprising administering an effective amount of a compound or salt of any one of the above embodiments of Formulas I, I-1, II, III, IV, V, VI, VII, VIII, and IXa-d or a pharmaceutical composition of any one of the above embodiments of Formulas I, I-1, II, III, IV, V, VI, VII, VIII, and IXa-d to the animal.

For certain embodiments, the present invention provides a method of treating a viral disease in an animal in need thereof comprising administering a therapeutically effective amount of a compound or salt of any one of the above embodiments of Formulas I, I-1, II, III, IV, V, VI, VII, VIII, and IXa-d or a pharmaceutical composition of any one of the above embodiments of Formulas I, I-1, II, III, IV, V, VI, VII, VIII, and IXa-d to the animal.

For certain embodiments, the present invention provides a method of treating a neoplastic disease in an animal in need thereof comprising administering a therapeutically effective amount of a compound or salt of any one of the above embodiments of Formulas I, I-1, II, III, IV, V, VI, VII, VIII, and IXa-d or a pharmaceutical composition of any one of the above embodiments of Formulas I, I-1, II, III, IV, V, VI, VII, VIII, and IXa-d to the animal.

For certain embodiments, $R_a$ is selected from the group consisting of halogen, alkyl, haloalkyl, alkoxy, and —$N(R_9)_2$.

For certain embodiments, $R_a$ is selected from the group consisting of fluorine, alkyl, haloalkyl, alkoxy, and —$N(R_9)_2$.

For certain embodiments, $R_b$ is selected from the group consisting of halogen, hydroxy, alkyl, haloalkyl, alkoxy, and —$N(R_9)_2$.

For certain embodiments, $R_b$ is selected from the group consisting of halogen, hydroxy, alkyl, and alkoxy.

For certain embodiments, $R_b$ is hydroxy.

For certain embodiments, $R_e$ is selected from the group consisting of halogen, hydroxy, alkyl, alkenyl, haloalkyl, alkoxy, alkylthio, and —$N(R_9)_2$.

For certain embodiments, $R_e$ is selected from the group consisting of halogen, hydroxy, alkyl, and alkoxy.

For certain embodiments, $R_{A1}$ and $R_{B1}$ are each independently selected from the group consisting of hydrogen, halogen, alkyl, alkenyl, alkoxy, alkylthio, and —$N(R_9)_2$.

For certain embodiments, $R_{A1}$ and $R_{B1}$ are each independently selected from the group consisting of hydrogen and alkyl.

For certain embodiments, $R_{A1}$ and $R_{B1}$ are each methyl.

For certain embodiments, $R_1$ is selected from the group consisting of:

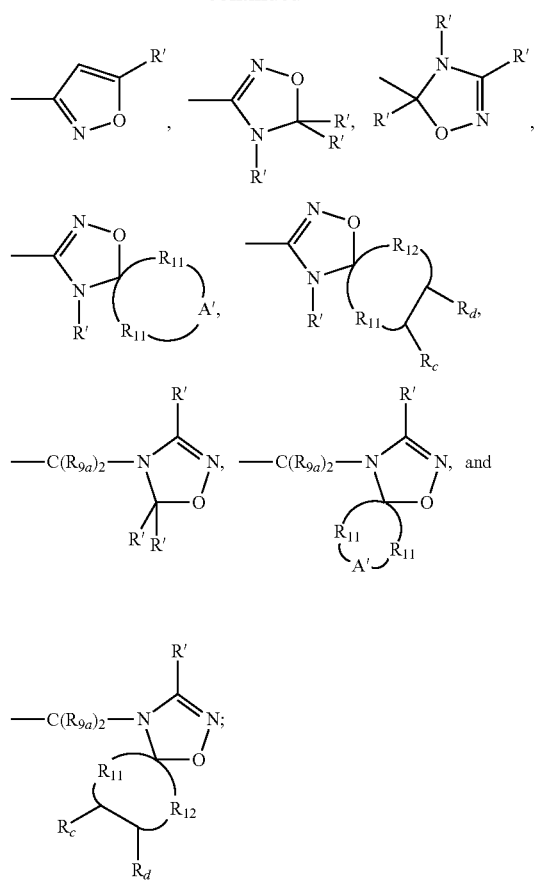

For certain embodiments, $R_1$ is selected from the group consisting of:

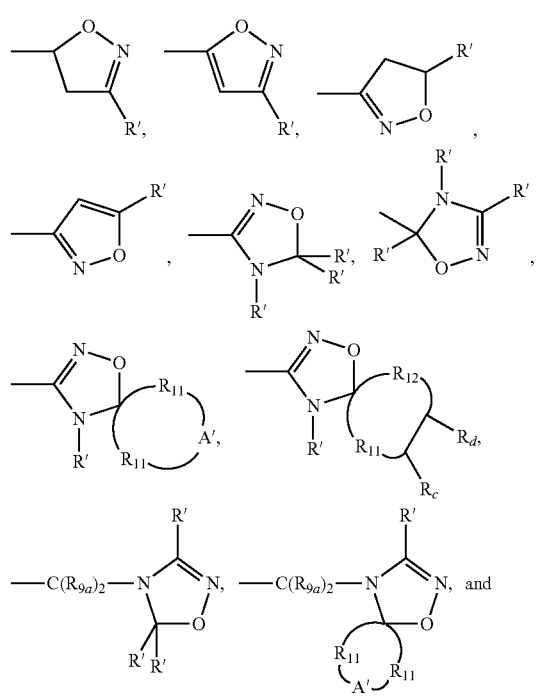

-continued

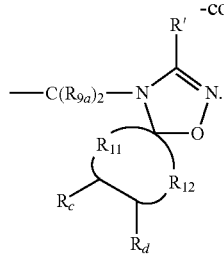

For certain embodiments, R$_1$ is selected from the group consisting of:

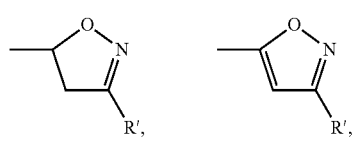

For certain embodiments, R$_1$ is selected from the group consisting of:

For certain embodiments, R$_1$ is selected from the group consisting of:

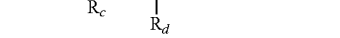

For certain embodiments, R$_1$ is

For certain embodiments, R$_1$ is selected from the group consisting of:

For certain embodiments, R$_1$ is

For certain embodiments, R$_1$ is

For certain embodiments, R$_1$ is selected from the group consisting of:

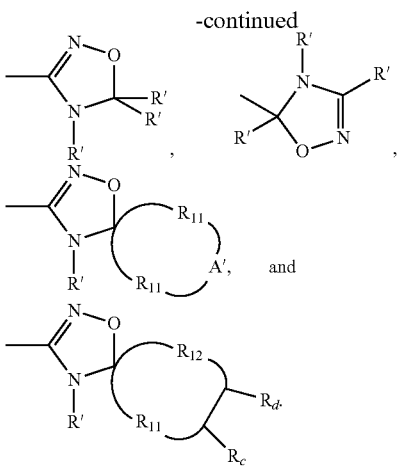

For certain embodiments, $R_1$ is

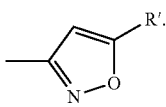

For certain embodiments, $R_2$ is selected from the group consisting of:
—$R_4$,
—X—$R_4$,
—X—Y—$R_4$, and
—X—$R_5$.

For certain embodiments, $R_2$ is hydrogen; alkoxyalkylenyl; hydroxyalkylenyl; haloalkylenyl; heterocyclylalkylenyl that is unsubstituted or substituted by one or more substituents selected from the group consisting of methyl, hydroxy, hydroxymethyl, and dimethylamino; —$R_4$; —X—$R_4$; or —X—Y—$R_4$. In certain of these embodiments, X is $C_{1-2}$ alkylene optionally terminated by heterocyclylene; Y is —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl that is unsubstituted or substituted by one or more substituents selected from the group consisting of hydroxy and cyano, aryl; or heterocyclyl that is unsubstituted or substituted by alkyl with the proviso that when Y is —C($R_6$)—O— or —C($R_6$)—N($R_8$)—, then $R_4$ may also be hydrogen. In certain of these embodiments, $R_8$ is selected from the group consisting of hydrogen, alkyl, arylalkylenyl, and hydroxyalkylenyl. In certain of these embodiments, $R_8$ is selected from the group consisting of hydrogen, alkyl, and arylalkylenyl.

For certain embodiments, $R_2$ is hydrogen, alkoxyalkylenyl, hydroxyalkylenyl, —$R_4$, —X—$R_4$, or —X—Y—$R_4$; wherein: X is $C_{1-2}$ alkylene; Y is —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl. In certain of these embodiments, $R_8$ is selected from the group consisting of hydrogen, alkyl, arylalkylenyl, and hydroxyalkylenyl. In certain of these embodiments, $R_8$ is selected from the group consisting of hydrogen, alkyl, and arylalkylenyl.

For certain embodiments, $R_2$ is hydrogen, $C_{1-4}$ alkyl, $C_{1-4}$ alkyl-O—$C_{1-4}$ alkylenyl, or hydroxy$C_{1-4}$ alkylenyl.

For certain embodiments, $R_2$ is methyl, ethyl, n-propyl, n-butyl, ethoxymethyl, 2-methoxyethyl, hydroxymethyl, or 2-hydroxyethyl.

For certain embodiments, $R_2$ is methyl, ethyl, n-propyl, n-butyl, ethoxymethyl, 2-methoxyethyl, hydroxymethyl, 2-hydroxyethyl, or fluoromethyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is alkyl.

For certain embodiments, $R_5$ is selected from the group consisting of:

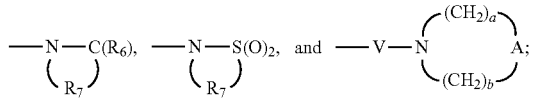

For certain embodiments, $R_6$ is selected from the group consisting of =O and =S.

For certain embodiments, $R_6$ is =O.

For certain embodiments, $R_7$ is $C_{2-7}$ alkylene.

For certain embodiments, $R_8$ is selected from the group consisting of hydrogen, alkyl, alkoxyalkylenyl, hydroxyalkylenyl, and arylalkylenyl.

For certain embodiments, $R_8$ is selected from the group consisting of hydrogen, alkyl, alkoxyalkylenyl, and arylalkylenyl.

For certain embodiments, $R_8$ is selected from the group consisting of hydrogen and alkyl.

For certain embodiments, $R_8$ is hydrogen.

For certain embodiments, $R_9$ is selected from the group consisting of hydrogen and alkyl.

For certain embodiments, $R_{9a}$ is selected from the group consisting of hydrogen and $C_{1-4}$ alkyl.

For certain embodiments, $R_{9a}$ is hydrogen.

For certain embodiments, $R_{9a}$ is methyl.

For certain embodiments, $R_{10}$ is $C_{3-8}$ alkylene.

For certain embodiments, $R_{11}$ is $C_{1-6}$ alkylene or $C_{2-6}$ alkenylene, wherein the alkylene or alkenylene is optionally interrupted by one heteroatom; and wherein the total number of atoms in the ring which includes $R_{11}$ is 4 to 9. For certain of these embodiments, $R_{11}$ is $C_{1-6}$ alkylene. For certain of these embodiments, the total number of atoms in the ring which includes $R_{11}$ is 5.

For certain embodiments, $R_{12}$ is selected from the group consisting of a bond, $C_{1-5}$ alkylene, and $C_{2-5}$ alkenylene, wherein the alkylene or alkenylene is optionally interrupted by one heteroatom; and wherein the total number of atoms in the ring which includes $R_{12}$ is 4 to 9.

For certain embodiments, R' is selected from the group consisting of hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, nitrile, nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—(CO)-alkyl, and —C(O)-alkyl.

For certain embodiments, R' is selected from the group consisting of alkyl, aryl, and heteroaryl, each of which is unsubstituted or substituted by one or more substituents selected from the group consisting of alkyl, alkoxy, halogen, and haloalkyl.

For certain embodiments, R' is selected from the group consisting of methyl; butyl; phenyl which is unsubstituted or substituted by one or more substituents selected from the group consisting of fluorine and trifluoromethyl; and 3-pyridyl.

For certain embodiments, R' is selected from the group consisting of methyl; phenyl which is unsubstituted or substituted by one or more substituents selected from the group consisting of fluorine and trifluoromethyl; and 3-pyridyl.

For certain embodiments, R' is methyl.

For certain embodiments, R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms.

For certain embodiments, R$_c$ and R$_d$ are each hydrogen.

For certain embodiments, R$_c$ and R$_d$ join to form a benzo ring.

For certain embodiments, A is selected from the group consisting of —O—, —C(O)—, —S(O)$_{0-2}$—, —CH$_2$—, and —N(R$_4$)—.

For certain embodiments, A is —O—.

For certain embodiments, A' is selected from the group consisting of —O—, —S(O)$_{0-2}$—, —N(-Q-R$_4$)—, and —C(R$_{9a}$)$_2$—.

For certain embodiments, A' is —C(R$_{9a}$)$_2$—.

For certain embodiments, Q is selected from the group consisting of a bond, —C(R$_6$)—, —C(R$_6$)—C(R$_6$)—, —S(O)$_2$—, and —S(O)$_2$—N(R$_8$)—

For certain embodiments, Q is —C(O)—, —S(O)$_2$—, or —C(O)—NH—.

For certain embodiments, V is selected from the group consisting of —C(R$_6$)—, —O—C(R$_6$)—, and —S(O)$_2$—.

For certain embodiments, V is —C(O)—.

For certain embodiments, X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups.

For certain embodiments, X is C$_{1-4}$ alkylene.

For certain embodiments, X is C$_{1-2}$ alkylene.

For certain embodiments, X' is selected from the group consisting of —CH(R$_9$)—, —CH(R$_9$)-alkylene-, and —CH(R$_9$)-alkenylene-.

For certain embodiments, X' is C$_{1-4}$ alkylene.

For certain embodiments, X' is —CH$_2$—.

For certain embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

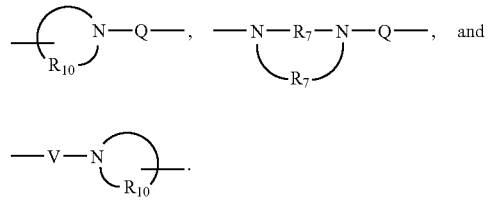

For certain embodiments, Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, or —C(R$_6$)—N(OR$_9$)—.

For certain embodiments, a and b are each independently an integer from 1 to 6 with the proviso that a+b is ≦7.

For certain embodiments, a and b are each independently 1 to 3.

For certain embodiments, a and b are each 2.

For certain embodiments, n is an integer from 0 to 4.

For certain embodiments, n is 0 or 1.

For certain embodiments, n is 0.

For certain embodiments, m is an integer from 0 to 3.

For certain embodiments, m is 0 or 1.

For certain embodiments, m is 0.

For certain embodiments of the compounds of Formulas I, I-1, II, III, IV, V, VI, VII, VIII, X, and IXa-d the —NH$_2$ group can be replaced by an —NH-G group, as shown in the compound of Formula I-1, to form prodrugs. In such embodiments, G is selected from the group consisting of —C(O)—R", α-aminoacyl, α-aminoacyl-α-aminoacyl, —C(O)—O—R", —C(O)—N(R'")R", —C(=NY')—R", —CH(OH)—C(O)—OY', —CH(OC$_{1-4}$alkyl)Y$_0$, —CH$_2$Y$_1$, and —CH(CH$_3$)Y$_1$. In some embodiments G is selected from the group consisting of —C(O)—R", α-aminoacyl, α-aminoacyl-α-aminoacyl, and —C(O)—O—R". Preferably, R" and R'" are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$. R'" may also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl. Preferably, Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments containing —NH-G, G is —C(O)—R", α-aminoacyl, α-aminoacyl-α-aminoacyl, or —C(O)—O—R".

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organzischenz Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention or pharmaceutically acceptable salts thereof, as well as various intermediates related thereto. Such techniques may include, for example, all types of chromatography (high performance liquid chromatography (HPLC), column chromatography using common absorbents such as silica gel, and thin layer chromatography, recrystallization, and differential (i.e., liquid-liquid) extraction techniques.

Compounds of the invention are prepared according to Reaction Scheme I, wherein $R_a$, $R'$, $R_2$, $X'$, and n are as defined above; the bond represented by the dotted line can either be present or absent; and $R_{1a}$ is a subset of $R_1$ that includes the rings:

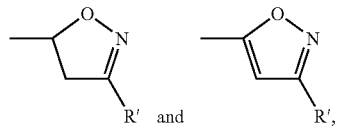

wherein R' is as defined above. In step (1) of Reaction Scheme I, an amine of Formula $NH_2-X'-CH=CH_2$ or $NH_2-X'-C\equiv C-H$ is combined with a 2,4-dichloro-3-nitroquinoline of Formula XV. This reaction is conveniently carried out by adding the amine to a solution of a compound of Formula XV in the presence of a base such as triethylamine. The reaction is carried out in a suitable solvent, such as dichloromethane, chloroform, or DMF and may be carried out at room temperature, a sub-ambient temperature such as 0° C., or an elevated temperature such as the reflux temperature of the solvent. Several compounds of Formula XV are known and can be made by known methods. See, for example, U.S. Pat. No. 4,689,338 (Gerster) and U.S. Pat. No. 4,988,815 (André et al). Amines of the Formula $NH_2-X'-CH=CH_2$ or $NH_2-X'-C\equiv C-H$ are commercially available or can be readily prepared by known methods.

The resultant compound of Formula XVI is reduced in step (2) of Reaction Scheme I to provide a 2-chloroquinoline-3,4-diamine of Formula XVII. Step (2) is conveniently carried out using a one- or two-phase sodium dithionite reduction. The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XVI in a mixture of dichloromethane and water at room temperature in the presence of potassium carbonate and ethyl viologen dibromide, ethyl viologen diiodide, or 1,1'-di-n-octyl-4,4'-bipyridinium dibromide. Alternatively, the reduction can be carried out by adding an aqueous solution of sodium dithionite to a compound of Formula XVI in a suitable solvent or solvent mixture such as ethanol/acetonitrile.

In step (3) of Reaction Scheme I, a 2-chloroquinoline-3,4-diamine of Formula XVII is treated with a carboxylic acid equivalent to provide a 1H-imidazo[4,5-c]quinoline of Formula XVIII. Suitable carboxylic acid equivalents include orthoesters of Formula $R_2C(O-alkyl)_3$, 1,1-dialkoxyalkyl alkanoates of Formula $R_2C(O-alkyl)_2(O-C(O)-alkyl)$, and acid chlorides of Formula $R_2C(O)Cl$. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a quinoline-3,4-diamine of Formula XVII in a suitable solvent such as toluene. Optionally, catalytic pyridine hydrochloride or pyridinium p-toluenesulfonate can be added. The reaction is carried out at a temperature high enough to drive off alcohol or water formed during the reaction. Conveniently, a Dean-Stark trap can be used to collect the volatiles.

Alternatively, step (3) can be carried out in two steps when an acid chloride of Formula $R_2C(O)Cl$ is used as the carboxylic acid equivalent. The first step is conveniently carried out by adding the acid chloride to a solution of a quinoline-3,4-diamine of Formula XVII in a suitable solvent such as dichloromethane to afford an amide. Optionally, a tertiary amine such as triethylamine, pyridine, or catalytic 4-dimethylaminopyridine (DMAP) can be added. The reaction can be carried out at or below room temperature. The amide product can be isolated and optionally purified using conventional techniques before it is heated and cyclized to provide a 1H-imidazo[4,5-c]quinoline of Formula XVIII. The cyclization reaction is conveniently carried out in a solvent such as ethanol or methanol or a solvent mixture such as ethanol/water in the presence of a base such as triethylamine, potassium carbonate, or sodium hydroxide and may be carried out at an elevated temperature, such as the reflux temperature of the solvent.

In step (4) of Reaction Scheme I, the alkene or alkyne group of a compound of Formula XVIII undergoes a cycloaddition reaction with a nitrile oxide formed from an α-chloroaldoxime of Formula XIX, to provide a isoxazole or dihydroisoxazole-substituted 1H-imidazo[4,5-c]quinoline of Formula Xa, a subgenus of Formula X. α-Chloroaldoximes of Formula XIX can be prepared by treating an aldoxime of Formula R'(H)C=N—OH with N-chlorosuccinimide in a suitable solvent such as N,N-dimethylformamide (DMF). The reaction may be carried out initially below room temperature, at 0° C. for example, and then heated at an elevated temperature in the range of 40° C. to 50° C. Aldoximes of Formula R'(H)C=N—OH are commercially available or can be prepared from aldehydes by methods well known to one skilled in the art. The resulting α-chloroaldoxime of Formula XIX can be isolated using conventional methods before it is combined with a compound of Formula XVIII in the presence of a base such as triethylamine to generate a nitrile oxide in situ and effect the cycloaddition reaction. The reaction with an α-chloroaldoxime can be carried out at room temperature in a suitable solvent such as dichloromethane.

In step (5) of Reaction Scheme I, a compound of Formula Xa is aminated to provide a 1H-imidazo[4,5-c]quinolin-4-amine of Formula IIIa, a subgenus of Formulas I and III. The reaction is conveniently carried out by adding a solution of ammonia in a suitable solvent such as methanol to a compound of Formula Xa and heating the reaction at an elevated temperature such as 150° C. The reaction may be carried out in a pressure vessel.

lines are also known and can be prepared by known methods as described in Reaction Scheme I. Related routes to tetrahydroquinolines of Formula XXI are known; see, for example, U.S. Pat. Nos. 5,352,784 (Nikolaides et al) and 6,670,372 (Charles et al).

In step (2) of Reaction Scheme II a compound of Formula XXI is reacted with an alkali metal azide to provide a tetrazole of Formula XXII. The reaction can be carried out by combining the compound of Formula XXI with an alkali metal azide, for example, sodium azide, in a suitable solvent such as acetonitrile/water, preferably 90/10 acetonitrile/water, in the presence of cerium (III) chloride, preferably cerium (III) chloride heptahydrate. Optionally, the reaction can be carried out with heating, for example, at the reflux temperature. Alternatively, the reaction can be carried out by combining the compound of Formula XXI with an alkali metal azide, for example, sodium azide, in a suitable solvent such as DMF and heating, for example in the range of 50° C. to 60° C., optionally in the presence of ammonium chloride. Other related routes to imidazonaphthyridines of Formula XXII have been reported; see, for example, U.S. Pat. No. 6,194,425 (Gerster et al).

In step (3) of Reaction Scheme II, the nitro group of the compound of Formula XXII is reduced to provide a diamine of Formula XXIII. The reduction can be carried out according

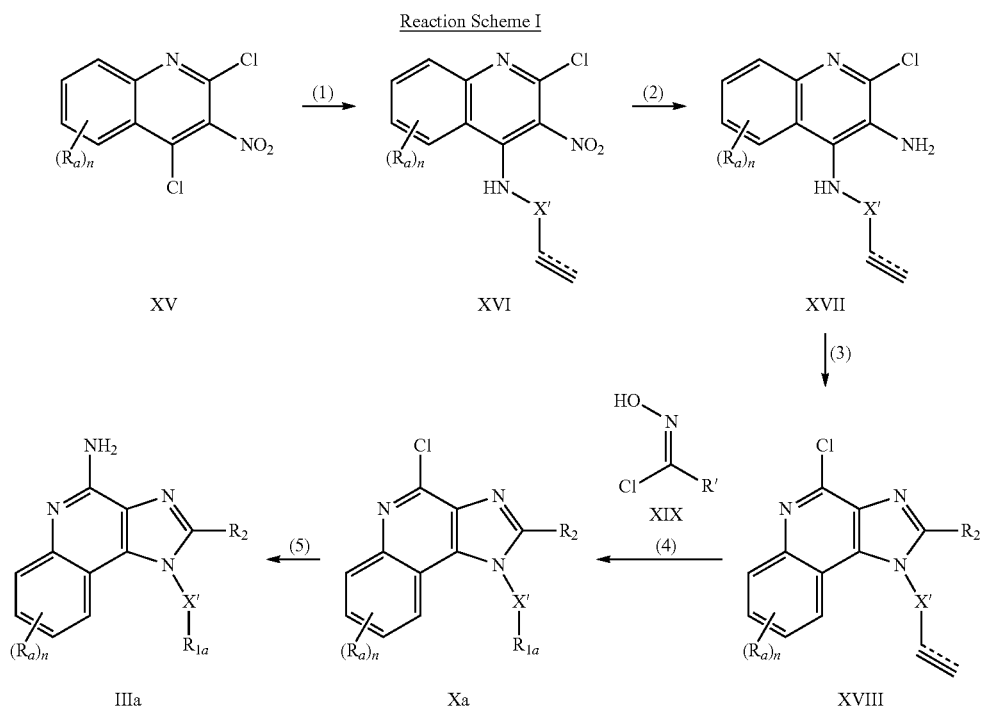

Reaction Scheme I

Compounds of the invention can be prepared according to Reaction Scheme II, wherein $R_A$, $R_B$, X', $R_2$, and $R_{1a}$ are as defined above. In step (1) of Reaction Scheme II, a compound of Formula XX is reacted with an amino alcohol of the Formula $H_2N$—X'—OH to form a compound of Formula XXI. The reaction is conveniently carried out according to the method described in step (1) of Reaction Scheme I. Many 2,4-dichloro-3-nitropyridines of the Formula XX are known and can be readily prepared using known synthetic methods. See, for example, Dellaria et al, U.S. Pat. No. 6,525,064 and the references cited therein. Many 2,4-dichloro-3-nitroquinoto one of the methods described in step (2) of Reaction Scheme I. Alternatively, the reduction can be carried out by hydrogenation using a heterogeneous hydrogenation catalyst such as platinum on carbon. The hydrogenation is conveniently carried out in a Parr apparatus in a suitable solvent such as toluene, a lower alcohol such as isopropanol or ethanol, or mixtures thereof. Other suitable solvents include ethyl acetate and acetonitrile. The reaction can be carried out at room temperature.

In step (4) of Reaction Scheme II, a diamine of Formula XXIII is reacted with a carboxylic acid equivalent to provide a compound of Formula XXIV. The reaction can be carried out as described in step (3) of Reaction Scheme I. Some pyridines of Formula XXIV are known; see, for example, U.S. Pat. No. 6,797,718 (Dellaria et al).

In step (5) of Reaction Scheme II, the alcohol of Formula XXIV is oxidized to an aldehyde-substituted compound of Formula XXV using conventional methods, for example, Swern oxidation conditions. The Swern oxidation is conveniently carried out by adding a compound of Formula XXIV followed by triethylamine to a mixture of oxalyl chloride and dimethylsulfoxide in a suitable solvent, such as dichloromethane. The reaction can be carried out at sub-ambient temperatures, such as −78° C.

In step (6) of Reaction Scheme II, an aldehyde-substituted compound of Formula XXV is converted to an alkenyl- or alkynyl-substituted compound of Formula XXVI. The conversion to an alkyne is conveniently carried out by adding diethyl 1-diazo-2-oxopropylphosphonate to the aldehyde-substituted compound of Formula XXV in the presence of a mild base such as potassium carbonate. The reaction is carried out in a suitable solvent such as methanol or dichloromethane at room temperature. The aldehyde-substituted compound of Formula XXV can be converted to an alkenyl-substituted compound of Formula XXVI using synthetic methods well known to those skilled in the art; such methods include the Wittig reaction.

In step (7) of Reaction Scheme II, the alkene or alkyne dipolarophile of Formula XXVI undergoes a cycloaddition reaction with a nitrile oxide generated from an α-chloroaldoxime of Formula XIX. The reaction can be run according to the methods described in step (4) of Reaction Scheme I to provide a product of Formula XXVII.

In step (8) of Reaction Scheme II, the tetrazole ring is removed from a compound of Formula XXVII by reaction with triphenylphosphine to form an N-triphenylphosphinyl intermediate. The reaction with triphenylphosphine can be run in a suitable solvent such as toluene or 1,2-dichlorobenzene under an atmosphere of nitrogen with heating, for example at the reflux temperature. The N-triphenylphosphinyl intermediate is then hydrolyzed to provide a compound of Formula Ia. The hydrolysis can be carried out by general methods well known to those skilled in the art, for example, by heating in a lower alkanol such as methanol in the presence of an acid such as hydrochloric acid.

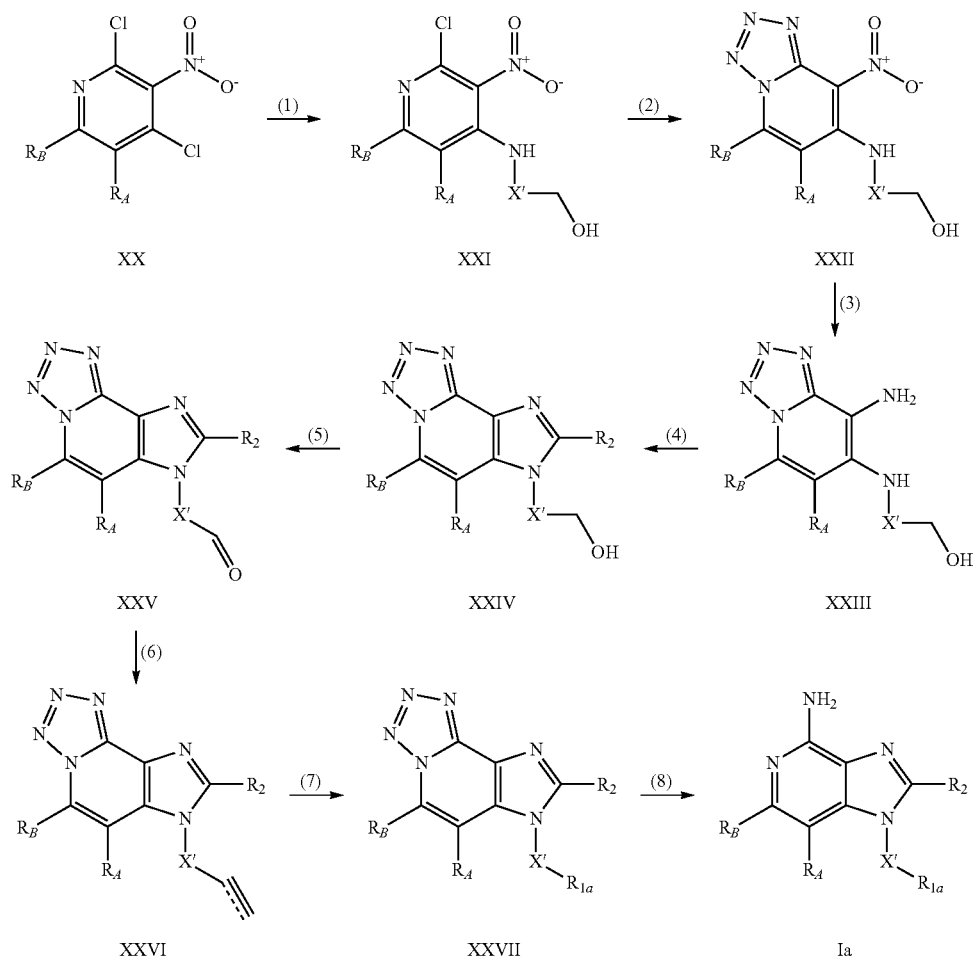

Reaction Scheme II

For certain embodiments, compounds of the invention are prepared according to Reaction Scheme III, wherein $R_a$, $R_2$, X', and n are as defined above, and $R_{1b}$ is a subset of $R_1$ that includes the rings:

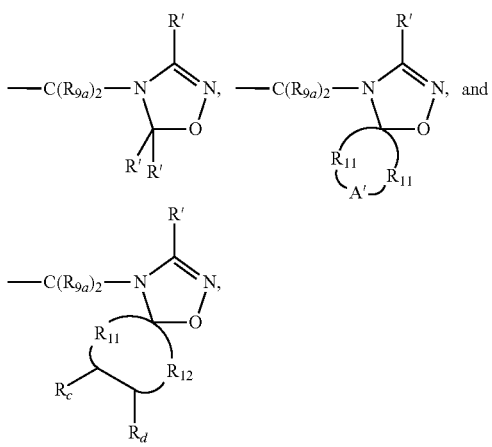

wherein R', $R_{9a}$, $R_{11}$, $R_{12}$, $R_c$, $R_d$, and A' are as defined above. In step (1) of Reaction Scheme III, a 1-aminoalkyl-substituted imidazoquinoline of Formula XXVIII is converted to an imine by reaction with a ketone or aldehyde of Formula (R')$_2$C=O and subsequently treated with an α-chloroaldoxime of Formula XIX. The reaction is conveniently carried out by combining an aminoalkyl-substituted imidazoquinoline of Formula XXVIII with a ketone or aldehyde of Formula (R')$_2$C=O,

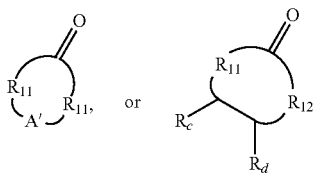

at room temperature in a suitable solvent such as dichloromethane. The reaction can optionally be carried out in the presence of magnesium sulfate. The resulting imine is then combined with an α-chloroaldoxime of Formula XIX according to the procedure described in step (4) of Reaction Scheme I. Some compounds of Formula XXVIII are known; see U.S. Pat. No. 6,069,149 (Nanba et al). Others can be readily prepared by known methods.

In step (2) of Reaction Scheme III, a 4-chloro-1H-imidazo[4,5-c]quinoline is aminated to provide a heterocyclyl-substituted 1H-imidazo[4,5-c]quinolin-4-amine of Formula IIIb. The reaction can be carried out according to the method described in step (5) of Reaction Scheme I.

Reaction Scheme III

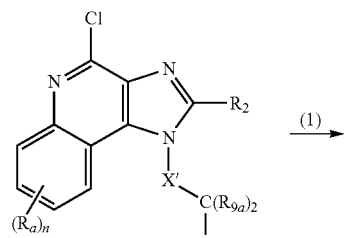

XXVIII

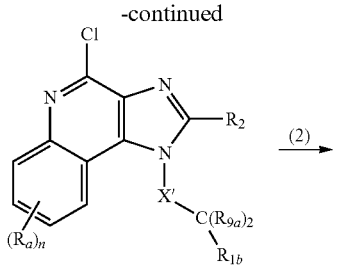

XXIX

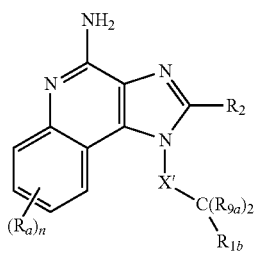

IIIb

An aldehyde-substituted compound of Formula XXV, shown in Reaction Scheme II, can also be used to make compounds of the invention wherein $R_1$ is

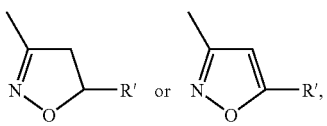

wherein R' is as defined above. The transformation is conveniently carried out by converting an aldehyde of Formula XXV to an aldoxime using methods well known to one of skill in the art, for example, by reaction with hydroxylamine hydrochloride in the presence of base such as aqueous sodium hydroxide in a suitable solvent such as ethanol, water, or mixtures thereof. The reaction can be run at room temperature. The aldoxime can then be converted to an α-chloroaldoxime and subsequently treated with triethylamine to generate a nitrile oxide in the presence of an alkene of formula R'—CH=CH$_2$ or an alkyne of formula R'—C≡C—H according to the methods described in step (4) of Reaction Scheme I. Numerous alkenes and alkynes of these formulas are commercially available; others can be prepared by known methods. The α-chloroaldoxime prepared by this method can also be treated with an imine generated from an amine of formula R'—NH$_2$ and a compound of formula (R')$_2$C=O,

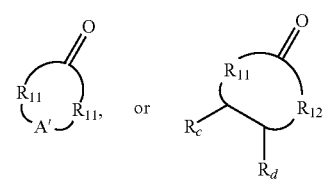

using the conditions described in step (1) of Reaction Scheme III to provide a compound of the invention wherein $R_1$ is

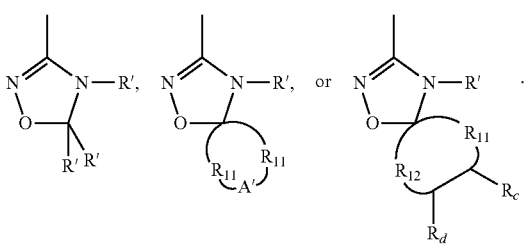

Numerous primary amines are commercially available and can be used to carry out this transformation.

Aldehydes of Formula XXV can also be used to prepare compounds of the invention wherein $R_1$ is

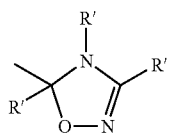

by first optionally converting it to a ketone using a Grignard reagent of formula R'MgHalide. Many Grignard reagents are commercially available, and their reaction with aldehydes to prepare secondary alcohols is well known to one of skill in the art. The secondary alcohol can then be oxidized to a ketone using one of numerous methods, such as the Swern oxidation described in step (5) Reaction Scheme II. The aldehyde of Formula XXV or the ketone prepared in this manner can be converted to an imine and reacted with an α-chloroaldoxime of Formula XIX according to the method described in step (1) of Reaction Scheme III. The method described in step (8) of Reaction Scheme II can be used after any of these alternative methods to provide a compound of Formula I.

Certain imidazonapthyridines of the invention can be prepared according to Reaction Scheme IV, wherein $R_b$, X', $R_2$, $R_{1a}$, R', and m are as defined above, and the bond represented by the dotted line can either be present or absent. Reaction Scheme IV begins with a 4-chloro-3-nitro[1,5]naphthyridine of Formula XXX. Compounds of Formula XXX and their preparation are known; see, for example, U.S. Pat. Nos. 6,194,425 (Gerster) and 6,518,280 (Gerster). Steps (1), (2), (3), and (4) of Reaction Scheme IV can be carried out according to the methods described in steps (1), (4), (2), and (3), respectively, of Reaction Scheme I to provide a substituted 1H-imidazo[4,5-c][1,5]naphthyridine of Formula XXXIV. Alternatively, step (3) of Reaction Scheme IV can be carried out by hydrogenation as described in step (3) of Reaction Scheme II.

In step (5) of Reaction Scheme IV, a 1H-imidazo[4,5-c][1,5]naphthyridine of Formula XXXIV is oxidized to provide a 1H-imidazo[4,5-c][1,5]naphthyridine-5N-oxide of Formula XXXV using a conventional oxidizing agent capable of forming N-oxides. The reaction is conveniently carried out by adding 3-chloroperoxybenzoic acid to a solution of a compound of Formula XXXIV in a solvent such as dichloromethane or chloroform. The reaction can be carried out at room temperature.

In step (6) of Reaction Scheme IV, a 5N-oxide of Formula XXXV is aminated to provide a 1H-imidazo[4,5-c][1,5]napthyridin-4-amine of Formula Va, a subgenus of Formulas I and V. Step (6) can be carried out by the activation of an N-oxide of Formula XXXV by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXXV in a suitable solvent such as dichloromethane or chloroform and then adding p-toluenesulfonyl chloride or benzenesulfonyl chloride. The reaction can be carried out at ambient temperature.

Steps (5) and (6) of Reaction Scheme IV may be carried out as a one-pot procedure by adding 3-chloroperoxybenzoic acid to a solution of a compound of Formula XXXIV in a solvent such as dichloromethane or chloroform and then adding ammonium hydroxide and p-toluenesulfonyl chloride or benzenesulfonyl chloride without isolating the N-oxide compound of Formula XXXV.

The amination reaction in step (6) of Reaction Scheme IV can alternatively be carried out by treating a 5N-oxide of Formula XXXV with trichloroacetyl isocyanate followed by hydrolysis of the resulting intermediate to provide a compound of Formula Va, a subgenus of Formulas I and V. The reaction is conveniently carried out in two steps by (i) adding trichloroacetyl isocyanate to a solution of a 5N-oxide of Formula XXXV in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

Reaction Scheme IV

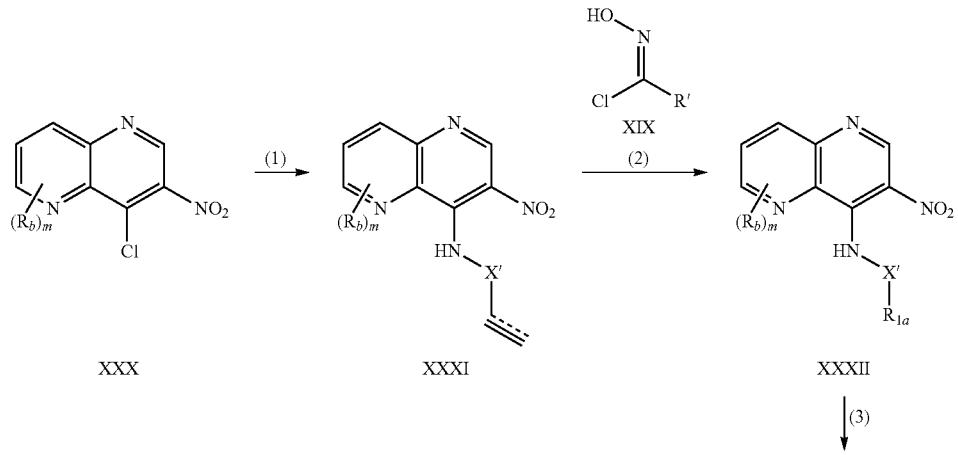

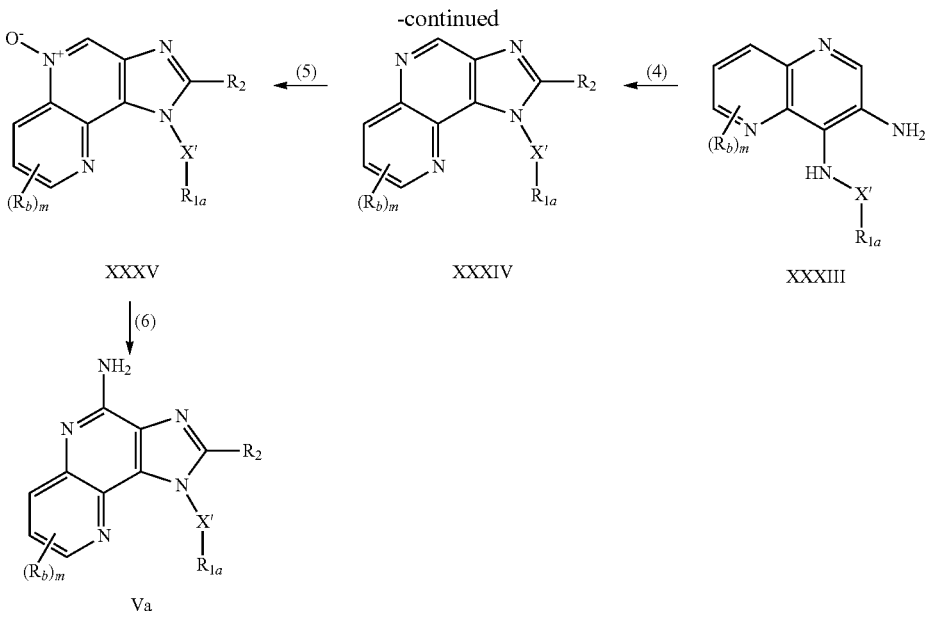

For certain embodiments, compounds of the invention can be prepared according to Reaction Scheme V, wherein $R_A$, $R_B$, X', $R_2$, $R_{9a}$, and $R_{1b}$ are as defined above. In Reaction Scheme V, an aminoalkyl-substituted compound of Formula XXXVI is converted to a heterocyclyl-substituted compound of Formula Ib according to the method described in step (1) of Reaction Scheme III. Many compounds of Formula XXXVI are known, including 1H-imidazo[4,5-c]quinolines and 6,7,8,9-tetrahydro-1H-imidazo[4,5-c]quinolines in U.S. Pat. Nos. 6,451,810 (Coleman et al) and 6,677,349 (Griesgraber), 1H-imidazo[4,5-c][1,5]naphthyridines in U.S. Pat. No. 6,194,425 (Gerster), and 1H-imidazo[4,5-c]pyridines in U.S. Pat. No. 6,545,016 (Dellaria et al).

Reaction Scheme V

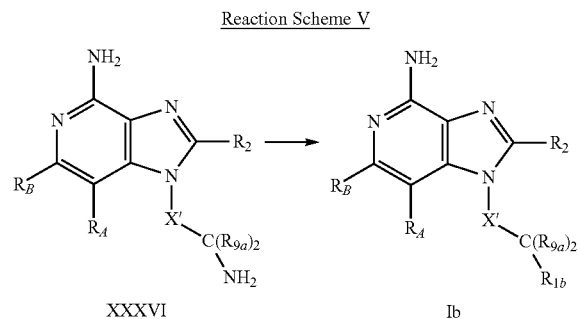

Compounds of the invention can also be prepared according to Reaction Scheme VI, wherein n is as defined above; $R_f$ is alkyl, alkoxy, or —N($R_9$)$_2$; X'$_c$ is —CH($R_9$)— or —CH($R_9$)-alkylene-; and $R_{2c}$ and $R_{1c}$ are subsets of $R_2$ and $R_1$ as defined above that do not include those substituents that one skilled in the art would recognize as being susceptible to reduction under the acidic hydrogenation conditions of the reaction. These susceptible groups include, for example, alkenyl and alkynyl groups and groups bearing nitro substituents.

As shown in Reaction Scheme VI, an 1H-imidazo[4,5-c]quinoline of Formula IIIf, prepared according to the methods described in any of Reaction Schemes I through III and V, is reduced to a 6,7,8,9-tetrahydro-1H-imidazo[4,5-c]quinolin-4-amine of Formula IVa, a subgenus of Formulas I and IV. The reaction is conveniently carried out under hetereogeneous hydrogenation conditions by adding platinum (IV) oxide to a solution of the compound of Formula IIIf in trifluoroacetic acid and placing the reaction under hydrogen pressure. The reaction can be carried out on a Parr apparatus at room temperature.

Reaction Scheme VI

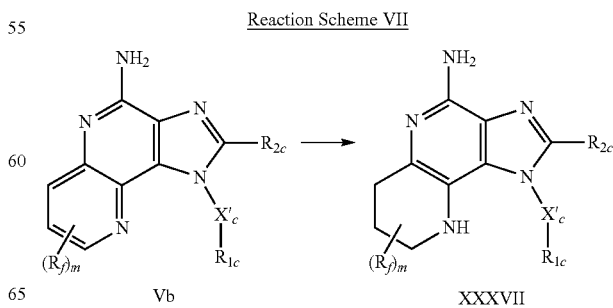

Compounds of the invention can also be prepared according to Reaction Scheme VII, wherein $R_{1c}$, $R_{2c}$, $R_f$, X'$_c$, and m are as defined above. In Reaction Scheme VII, a 1H-imidazo[4,5-c][1,5]naphthyridin-4-amine of Formula Vb, prepared as described in any one of Reaction Schemes II, IV, and V is reduced to a 6,7,8,9-tetrahydro-1H-imidazo[4,5-c][1,5]naphthyridin-4-amine of Formula XXXVII, a subgenus of Formulas I and IXa. The reaction is conveniently carried out using the conditions described in Reaction Scheme VI.

Reaction Scheme VII

Imidazo[4,5-c]pyridines of the invention can be prepared according to Reaction Scheme VIII, wherein $R_{A1}$, $R_{B1}$, X', R', $R_2$, and $R_{1a}$ are as defined above, the bond represented by the dotted line can either be present or absent, and Bn is benzyl or p-methoxybenzyl. In step (1) of Reaction Scheme VIII, a 2,4-dichloro-3-nitropyridine of Formula XXXVIII is reacted with an amine of Formula $NH_2$—X'—CH=$CH_2$ or $NH_2$—X'—C≡C—H as described in step (1) of Reaction Scheme I. Many 2,4-dichloro-3-nitropyridines of Formula XXXVIII are known as referenced in Reaction Scheme II.

In step (2) of Reaction Scheme VIII, the chloro group in a pyridine of Formula XXXIX is displaced by an amine of Formula $HN(Bn)_2$ to provide a pyridine of Formula XL. The displacement is conveniently carried out by combining an amine of Formula $HN(Bn)_2$ and a compound of Formula XXXIX in a suitable solvent such as toluene or xylenes in the presence of a base such as triethylamine and heating at an elevated temperature such as the reflux temperature of the solvent.

In step (3) of Reaction Scheme VIII, a compound of Formula XL is reduced to provide a pyridine-2,3,4-triamine of Formula XLI. The reduction can be carried out as described in step (2) of Reaction Scheme I. The reaction can be carried out using alternative methods as described in U.S. Pat. No. 5,395,937 (Nikolaides et al).

In step (4) of Reaction Scheme VIII, a quinoline-2,3,4-triamine of Formula XLI is cyclized to a 1H-imidazo[4,5-c]pyridine of Formula XLII. The reaction is carried out according to one of the methods described in step (3) of Reaction Scheme I.

In step (5) of Reaction Scheme VIII, the alkene or alkyne dipolarophile of Formula XLII undergoes a cycloaddition reaction with a nitrile oxide generated from a α-chloroaldoxime of Formula XIX. The reaction can be run according to the methods described in step (4) of Reaction Scheme I to provide a product of Formula XLIII.

In step (6) of Reaction Scheme VIII, the protecting groups are removed from the 4-amine of a pyridine of Formula XLIII to provide a substituted 1H-imidazo[4,5-c]pyridin-4-amine of Formula IIa, a subgenus of Formulas I and II. The deprotection is conveniently carried out on a Parr apparatus under hydrogenolysis conditions using a suitable heterogeneous catalyst such as palladium on carbon in a solvent such as ethanol. The reaction can also be carried out by adding trifluoroacetic acid to a compound of Formula XLIII and stirring at room temperature or heating at an elevated temperature such as 50° C. to 70° C.

Reaction Scheme VIII

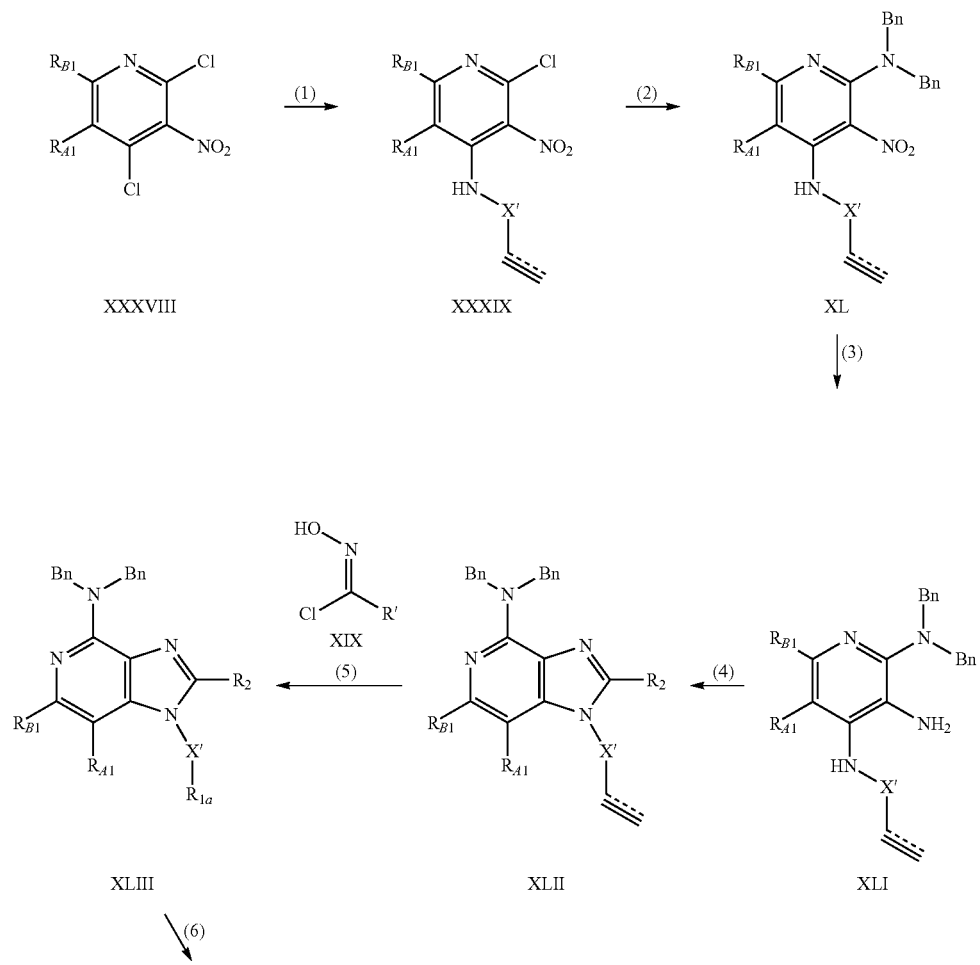

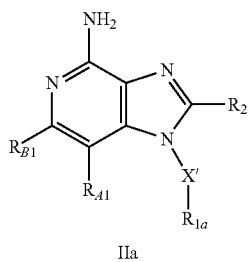

IIa

For some embodiments, tetrahydroquinolines of the invention can be prepared according to Reaction Scheme IX, wherein $R_f$, $X'_c$, $R_{2c}$, $R_{1a}$, and n are as defined above; Boc is a tert-butoxycarbonyl group; and PG is a hydroxy protecting group. In step (1) of Reaction Scheme I, the hydroxy group of a substituted quinoline of Formula XLIV is protected using conventional techniques to provide a substituted quinoline of Formula XLV. A number of suitable protecting groups can be used; in particular, protecting groups that would survive the reduction in step (2) are preferred. Suitable protecting groups include but are not limited to silyl groups such as the tert-butyldimethylsilyl group. The reaction is conveniently carried out by treating the hydroxy-substituted compound of Formula XLIV with tert-butyldimethylsilyl chloride in the presence of a base such as triethylamine and catalytic DMAP. The reaction can be carried out in a suitable solvent such as pyridine or dichloromethane at an elevated temperature such as 60° C. Compounds of Formula XLIV are available from the method described in step (1) of Reaction Scheme II.

In steps (2) and (3) of Reaction Scheme IX, the nitro group of a substituted quinoline of Formula XLV is first reduced to a 2-chloroquinolin-3,4-diamine of Formula XLVI, which is then cyclized to a 1H-imidazo[4,5-c]quinoline of Formula XLVII. Steps (2) and (3) of Reaction Scheme IX can be carried out as described in steps (2) and (3) of Reaction Scheme I.

In steps (4) and (5) of Reaction Scheme IX, a 1H-imidazo[4,5-c]quinoline of Formula XLVII is first aminated as described in step (5) of Reaction Scheme I to provide a 1H-imidazo[4,5-c]quinolin-4-amine of Formula XLVIII, which is then reduced to a 6,7,8,9-tetrahydro-1H-imidazo[4,5-c]quinolin-4-amine of Formula XLIX according to the method described in Reaction Scheme VI.

In step (6) of Reaction Scheme IX, the 4-amine of a 6,7,8,9-tetrahydro-1H-imidazo[4,5-c]quinolin-4-amine of Formula XLIX is protected with suitable protecting groups such as Boc groups. The protection reaction is conveniently carried out by combining a tetrahydro-1H-imidazo[4,5-c]quinolin-4-amine of Formula XLIX with di-tert-butyl dicarbonate in the presence of base, such as triethylamine, catalytic DMAP, or a combination thereof. The reaction can be carried out at room temperature in a suitable solvent such as toluene. Other protecting groups can be installed in this step using known synthetic methods.

In step (7) of Reaction Scheme IX, the hydroxy protecting group on a tetrahydro-1H-imidazo[4,5-c]quinoline of Formula L is removed to reveal the hydroxy group in a product of Formula LI. The deprotection reaction can be carried out using a variety of conventional methods, depending on the protecting group used. When PG is a silyl group such as tert-butyldimethylsilyl, the deprotection can be carried out by adding tetrabutylammonium fluoride to a compound of Formula L in a suitable solvent such as tetrahydrofuran (THF). The reaction can be carried out at a sub-ambient temperature, such as −78° C., and then warmed to room temperature.

Steps (8), (9), and (10) of Reaction Scheme IX can be carried out according to the methods described above in steps (5), (6), and (7) of Reaction Scheme II to provide a tetrahydro-1H-imidazo[4,5-c]quinoline of Formula LII, which is then deprotected to provide a tetrahydro-1H-imidazo[4,5-c]quinolin-4-amine of Formula IVb, a subgenus of Formulas I and IV. The removal of Boc protecting groups is conveniently carried out under acidic conditions by adding hydrogen chloride in ethanol to a compound of Formula LII in a suitable solvent such as ethanol. The reaction can be run at room temperature or at an elevated temperature such as 60° C.

Reaction Scheme IX

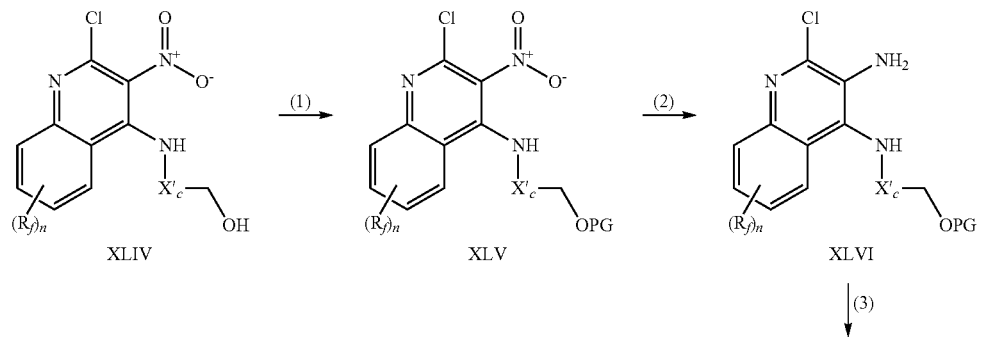

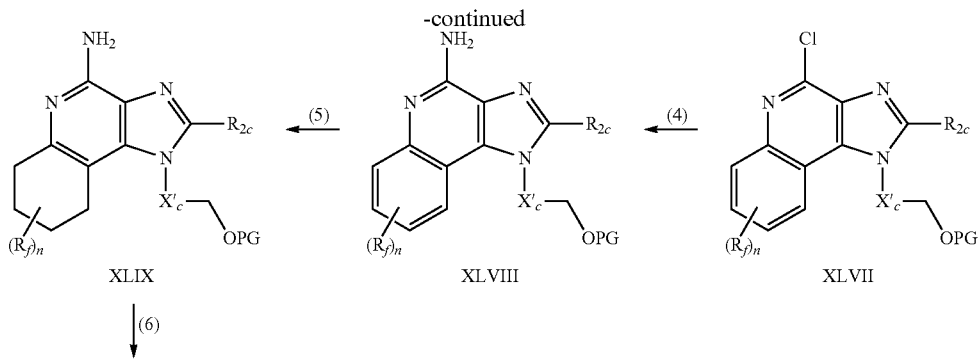

XLIX           XLVIII           XLVII

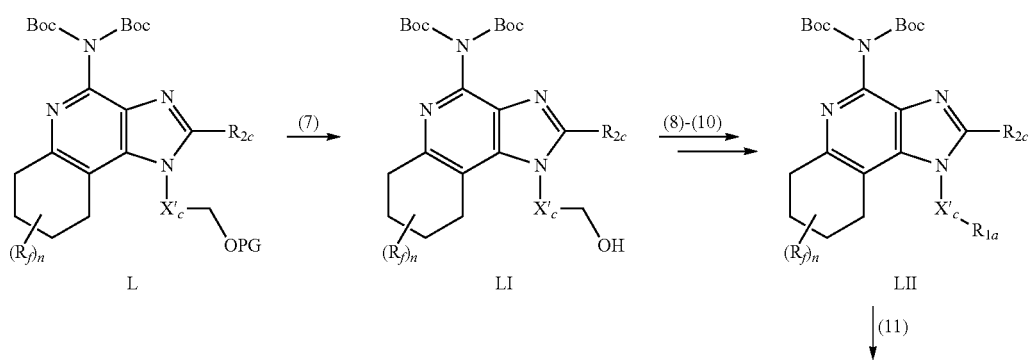

L           LI           LII

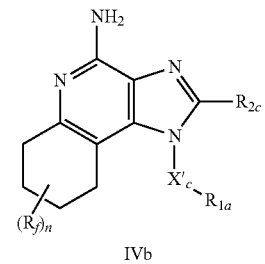

IVb

For some embodiments, tetrahydronapthyridines of the invention can be prepared according to Reaction Scheme X, wherein $R_f$, $X'_c$, $R_{2c}$, $R_{1a}$, PG, and m are as defined above. Steps (1) through (3) of Reaction Scheme X can be carried out according to the methods described in steps (1) through (3) of Reaction Scheme IX, starting with a [1,5]naphthyridine of Formula LIII. Some compounds of Formula LIII are known; others can be prepared according to known methods. See, for example, International Publication No. WO2005/018551.

In steps (4) and (5) of Reaction Scheme X, a 1H-imidazo[4,5-c][1,5]naphthyridine of Formula LV is first oxidized to a 5N-oxide of Formula LVI, which is aminated to yield a 1H-imidazo[4,5-c][1,5]naphthyridin-4-amine of Formula LVII. Steps (4) and (5) of Reaction Scheme X can be carried out as described in steps (5) and (6) of Reaction Scheme IV.

In step (6) of Reaction Scheme X, a 1H-imidazo[4,5-c][1,5]naphthyridin-4-amine of Formula LVII is reduced to a 6,7,8,9-tetrahydro-1H-imidazo[4,5-c][1,5]naphthyridin-4-amine of Formula LVIII, conveniently under the conditions described in Reaction Scheme VI.

Steps (7) through (12) of Reaction Scheme X can be carried out according to the methods described in steps (6) through (11) of Reaction Scheme IX, respectively, to provide a 6,7,8,9-tetrahydro-1H-imidazo[4,5-c][1,5]naphthyridin-4-amine of Formula XXVIIb, a subgenus of Formulas I and IXa.

Reaction Scheme X

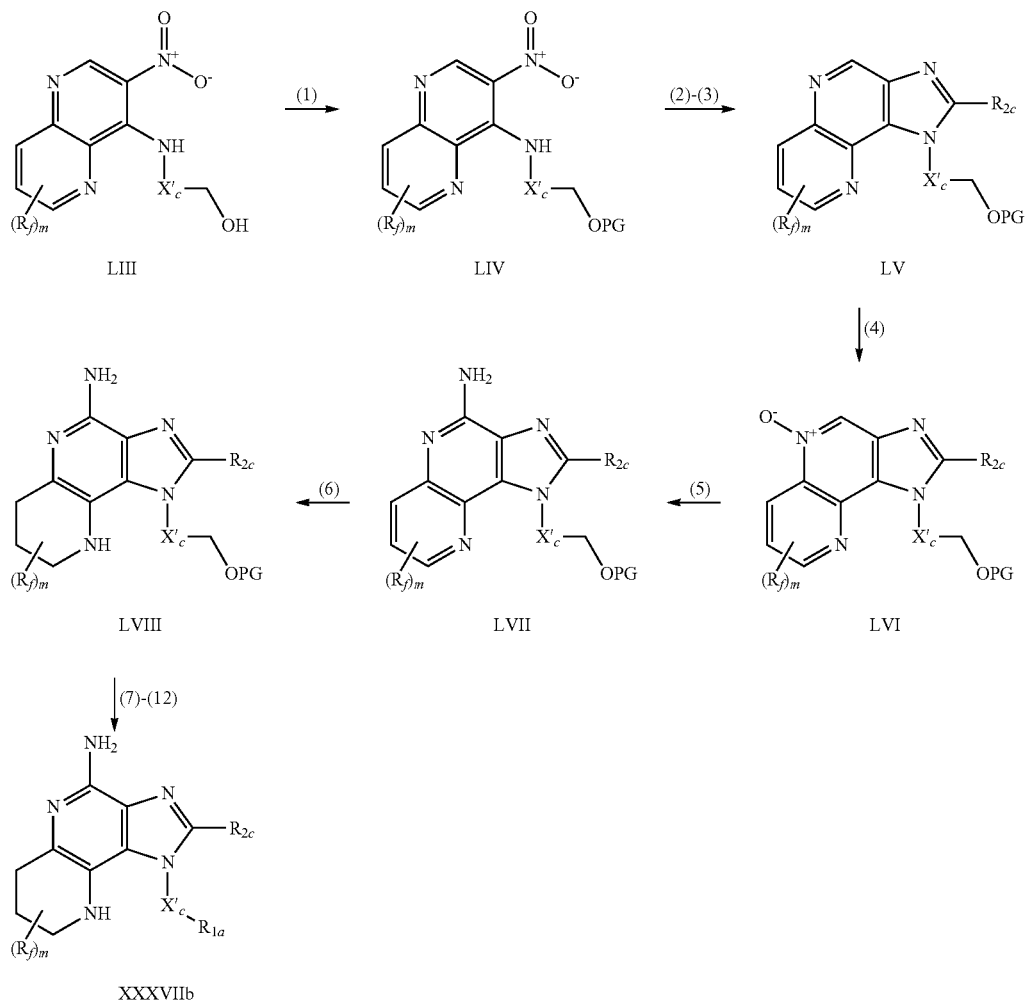

For some embodiments, compounds of the invention can be prepared according to Reaction Scheme XI, wherein $R_a$, X', $R_2$, and n are as defined above; $PG_1$ is a nitrogen protecting group; $R_{1d}$ is a subset of $R_1$ that includes the rings:

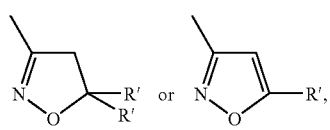

wherein R' is as defined above. In step (1) of Reaction Scheme XI, an aldehyde of Formula LIX is converted to an aldoxime of Formula LX using conventional methods. For example, an aldehyde of Formula LIX can be combined with hydroxylamine hydrochloride in the presence of base such as triethylamine in a suitable solvent such as dichloromethane. The reaction can be run at room temperature. Aldehydes of Formula LIX can be prepared using conventional methods. For example, phthalimidoacetaldehyde diethyl acetal is a commercially available compound that can be treated with acid to provide an aldehyde of Formula LIX.

In step (2) of Reaction Scheme XI, an aldoxime of Formula LX is converted to an α-chloroaldoxime of Formula LXI according to the method described in step (4) of Reaction Scheme I. The α-chloroaldoxime of Formula LXI is converted in step (3) of Reaction Scheme XI to an isoxazole or dihydroisoxazole-substituted compound of Formula LXII by treatment with a base such as triethylamine to generate a nitrile oxide in the presence of an alkene of formula R'—CH=CH$_2$ or an alkyne of formula R'—C≡C—H according to the methods described in step (4) of Reaction Scheme I. Numerous alkenes and alkynes of these formulas are commercially available; others can be prepared by known methods.

In step (4) of Reaction Scheme XI, the protecting groups are removed from a compound of Formula LXII to provide an amino-substituted isoxazole or dihydroisoxazole for Formula LXIII. The deprotection may be carried out in a variety of ways depending on the identity of the protecting group. For example, when a phthalimide protecting group is used, the deprotection can be carried out by combining a compound of Formula LXII with hydrazine or hydrazine hydrate in a suitable solvent such as ethanol or solvent mixture such as ethanol/THF. The reaction can be carried out at room temperature or at an elevated temperature such as the reflux temperature of the solvent.

In step (5) of Reaction Scheme XI, a 4-chloro-3-nitroquinoline of Formula LXIV is combined with an amine of Formula LXIII according to the method described in step (1) of Reaction Scheme I. In steps (6) and (7) of Reaction Scheme XI, the nitro group of a substituted quinoline of Formula LXV is first reduced to a quinolin-3,4-diamine of Formula LXVI, which is then cyclized to a 1H-imidazo[4,5-c]quinoline of Formula LXVII. Steps (6) and (7) of Reaction Scheme XI can be carried out as described in step (3) of Reaction Scheme II and step (3) of Reaction Scheme I, respectively.

In steps (8) and (9) of Reaction Scheme XI, a 1H-imidazo[4,5-c]quinoline of Formula LXVII is first oxidized to a 5N-oxide of Formula LXVIII, which is aminated to yield a 1H-imidazo[4,5-c]quinolin-4-amine of Formula IIIg, a sub- genus of Formulas I and III. Steps (8) and (9) of Reaction Scheme XI can be carried out as described in steps (5) and (6) of Reaction Scheme IV.

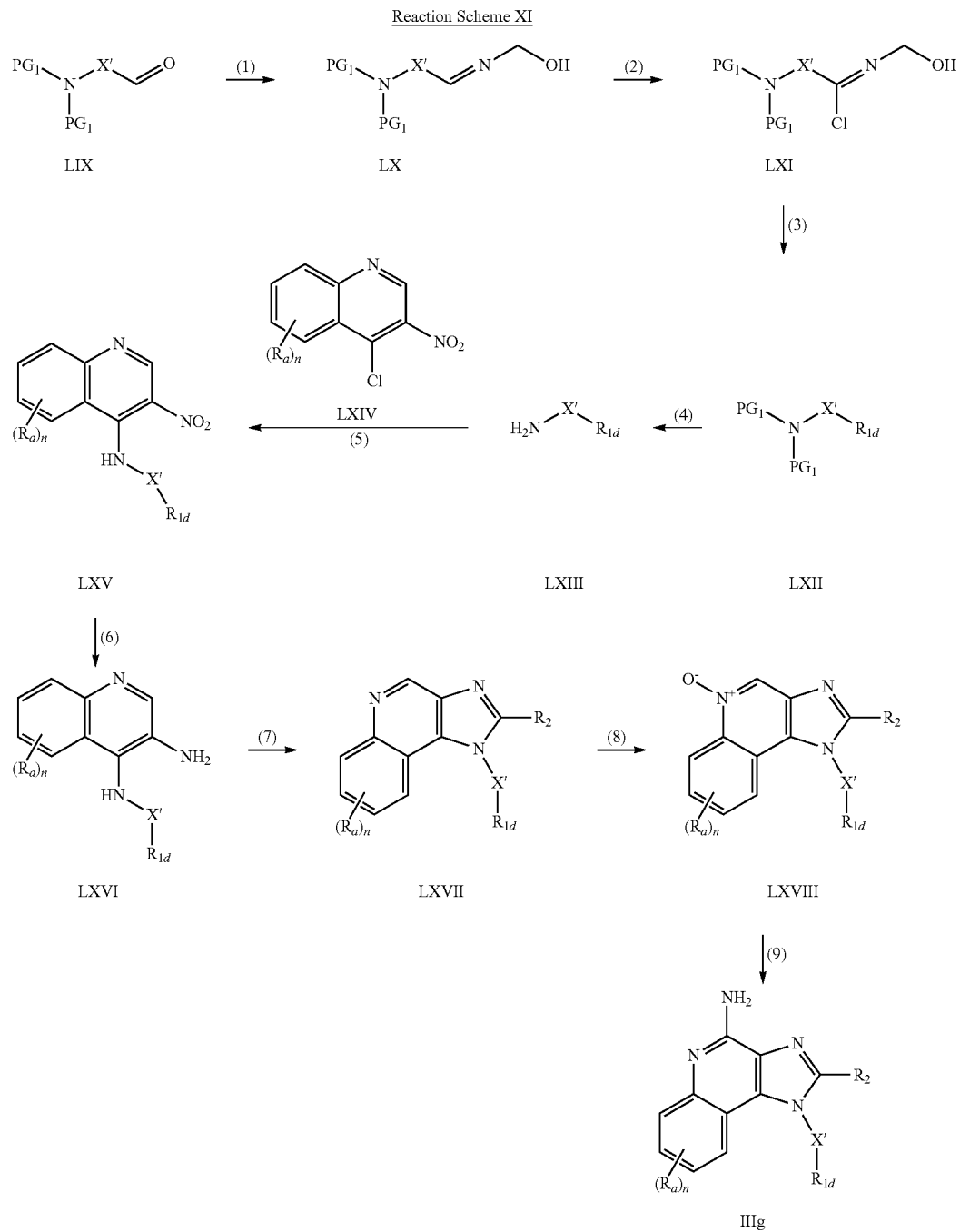

For some embodiments, compounds of the invention can be prepared according to Reaction Scheme XII, wherein $R_a$, $X'$, $R_{1a}$, $R_2$, and n are as defined above. In step (1) of Reaction Scheme XII, a 2,4-dichloro-3-nitroquinoline of Formula XV is combined with an amine of Formula LXIIIa according to the method described in step (1) of Reaction Scheme I. Amines of Formula LXIIIa can be prepared in two steps from a protected amino-substituted alkene or protected amino-substituted alkyne. In the first step, the alkene or alkyne group can be reacted with an α-chloroaldoxime of Formula XIX according to the method described in step (4) of Reaction Scheme I, and the resulting isoxazole or dihydroisoxazole is then deprotected to provide an amino of Formula LXIIIa. Some protected amino-substituted alkenes and protected amino-substituted alkynes are commercially available, such as N-(3-butynyl)phthalimide; others can be prepared by known methods. Steps (2), (3), and (4) of Reaction Scheme XII can then be carried out according to the methods described in step (3) of Reaction Scheme II, and step (3) and step (5) of Reaction Scheme I, respectively, to provide a compound of Formula IIIa.

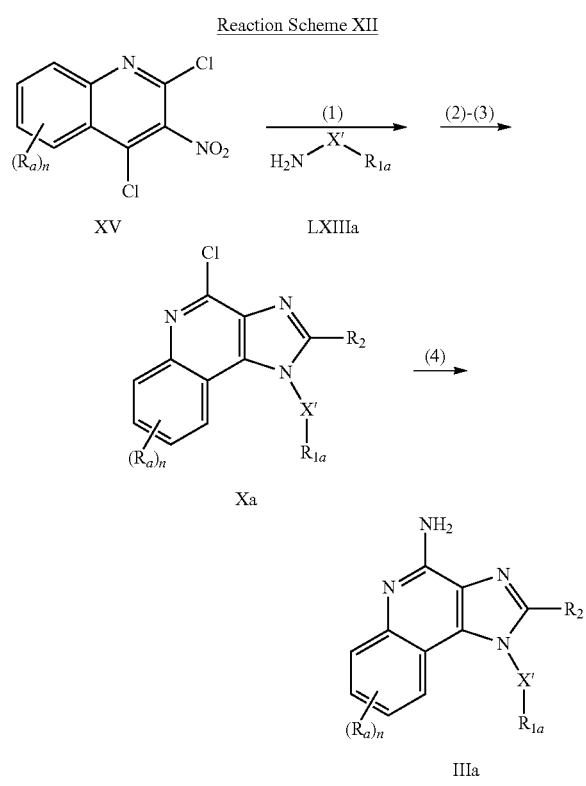

Synthetic transformations can be made at the $R_2$ position in many of the compounds shown in Reaction Schemes I through X, if, for example, the carboxylic acid or equivalent thereof used in step (3) of Reaction Scheme I, IX, or X, or step (4) of Reaction Scheme II, IV, or VIII contains a protected hydroxy or amino group. Some acid chlorides of this type are commercially available; others can be prepared by known synthetic methods. A protected hydroxy or amino group thus installed at the $R_2$ position can then be deprotected by a variety of methods well known to one of skill in the art. For example, hydroxyalkylenyl group is conveniently introduced at the $R_2$ position by the dealkylation of a methoxy- or ethoxy-alkylenyl group, which can be installed by using a methoxy- or ethoxy-substituted carboxylic acid equivalent, for example, methoxyacetyl chloride, 2-methoxypropionyl chloride, or ethoxyacetyl chloride, in step (3) of Reaction Scheme I or the analogous steps in the other Reaction Schemes. The dealkylation can be carried out by treating a compound wherein $R_2$ is an alkoxyalkylenyl group with boron tribromide in a suitable solvent such as dichloromethane at a sub-ambient temperature such as 0° C. Alternatively, acetoxy-acetyl chloride can be used in step (3) of Reaction Scheme I, and hydrolysis of the ester group to reveal a hydroxy group can be carried out by conventional methods. The resulting hydroxy group may then be oxidized to an aldehyde or carboxylic acid using conventional methods or converted to a leaving group such as, for example, a chloro group using thionyl chloride or a trifluoromethanesulfonate group using trifluoromethanesulfonic anhydride. The resulting leaving group can then be displaced by a variety of nucleophiles. Sodium azide can be used as the nucleophile to install an azide group, which can then be reduced to an amino group using heterogeneous hydrogenation conditions. An amino group at the $R_2$ position can be converted to an amide, sulfonamide, sulfamide, or urea using conventional methods. A leaving group at $R_2$, such as a chloro or trifluoromethanesulfonate group, can also be displaced with a secondary amine, a substituted phenol, or a mercaptan in the presence of a base such as potassium carbonate, triethylamine, or N,N-diisopropylethylamine in a suitable solvent such as N,N-dimethylacetamide (DMA) or DMF. For examples of these and other methods used to install a variety of groups at the $R_2$ position, see U.S. Pat. No. 5,389,640 (Gerster et al.). A hydroxyalkylenyl group at the $R_2$ position can also be converted to a fluoroalkylenyl group, by treating a hydroxy-substituted compound with (diethylamino)sulfur trifluoride (DAST) in a suitable solvent such as dichloromethane at a sub-ambient temperature, such as −78° C. These synthetic transformations may conveniently be carried out as the last steps in the synthesis.

Compounds of the invention can also be prepared using variations of the synthetic routes shown in Reaction Schemes I through XI that would be apparent to one of skill in the art. For example, the cycloaddition reaction described in step (4) of Reaction Scheme I may be carried out on a compound of Formula XVI or Formula XXXIX so that the order of steps in Reaction Schemes I and VIII is analogous to the order of steps in Reaction Scheme IV. In another example, a 4-chloro-3-nitro[1,5]naphthyridine of Formula XXX can be used instead of a 4-chloro-3-nitroquinoline of Formula LXIV in Reaction Scheme XI to provide naphthyridine compounds of the invention. Compounds of the invention can also be prepared using the synthetic routes described in the EXAMPLES below.

Prodrugs can be prepared in a variety of ways. For example, a compound wherein $R_2$ is —X—OH (e.g. hydroxyalkyl) can be converted into a prodrug wherein $R_2$ is, for example, —X—O—C($R_6$)—$R_4$, —X—O—C($R_6$)—O—$R_4$, or —X—O—C($R_6$)—N($R_8$)—$R_4$, wherein X, $R_4$, $R_6$, and $R_8$ are as defined above, using methods known to one skilled in the art. In addition, a compound wherein $R_b$ is hydroxy may also be converted to an ester, an ether, a carbonate, or a carbamate. For any of these compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. For compounds containing an alcohol functional group, particularly useful prodrugs are esters made from carboxylic acids containing one to six carbon atoms, unsubstituted or substituted benzoic acid esters, or esters made from naturally occurring L-amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R', α-aminoacyl, α-aminoacyl-α-aminoacyl, —C(O)—O—R', —C(O)—N(R")—R', —C(=NY')—R', —CH(OH)—C(O)—OY', —CH(OC$_{1-4}$ alkyl)Y$_0$, —CH$_2$Y$_1$, or —CH(CH$_3$)Y$_1$; wherein R' and R" are each independently C$_{1-10}$ alkyl, C$_{3-7}$ cycloalkyl, or benzyl, each of which may be unsubstituted or substituted by one or more substituents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH2, and —S(O)$_2$—NH$_2$, with the proviso that R" may also be hydrogen; each α-aminoacyl group is independently selected from racemic, D, or L-amino acids; Y' is hydrogen, C$_{1-6}$ alkyl, or benzyl; Y$_0$ is C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, or di-N,N—C$_{1-6}$ alkylaminoC$_{1-4}$ alkylenyl; and Y$_1$ is mono-N—C$_{1-6}$ alkylamino, di-N,N—C$_{1-6}$ alkylamino, morpholin-4-yl, piperidin-1-yl, pyrrolidin-1-yl, or 4-C$_{1-4}$ alkylpiperazin-1-yl. For compounds containing an amine functional group, particularly useful prodrugs are amides derived from carboxylic acids containing one to ten carbon atoms, amides derived from amino acids, and carbamates containing one to ten carbon atoms.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 (T$_H$1) cytokine IFN-γ may be induced indirectly and the production of the T helper type 2 (T$_H$2) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus,*

*Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carmii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus* influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

2-(Ethoxymethyl)-1-[(3-methyl-4,5-dihydroisoxazol-5-yl)methyl]-1H-imidazo[4,5-c]quinolin-4-amine

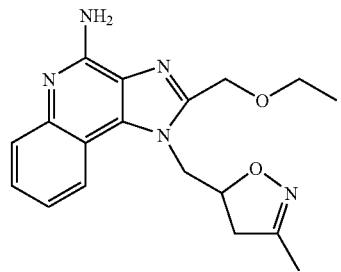

Part A

Triethylamine (17.0 mL, 123 mmol) was added to a 0° C. solution of 2,4-dichloro-3-nitroquinoline (20.0 g, 82.3 mmol) in dichloromethane (350 mL) followed by the dropwise addition of allylamine (5.90 mL, 78.2 mmol). The solution was allowed to stir and warm to room temperature overnight. The solvent was evaporated under reduced pressure and the resulting orange solid was suspended in water (300 mL). Solid sodium carbonate was added to adjust the pH to 10-11 and the suspension was stirred for 2 hours at 0° C. A yellow solid was isolated by filtration and dried under vacuum overnight to yield N-allyl-2-chloro-3-nitroquinolin-4-amine (21.7 g) that contained small amounts of an impurity and water.

Part B

An aqueous solution (200 mL) of potassium carbonate (55.3 g, 400 mmol) and sodium dithionate (62.7 g, 360 mmol) was added dropwise over 30 minutes to a mixture of N-allyl-2-chloro-3-nitroquinolin-4-amine (21.0 g, 79.9 mmol) and ethyl viologen dibromide (1.80 g, 4.80 mmol) in dichloromethane (320 mL) and water (40 mL) under a nitrogen atmosphere. The dark blue-green mixture was stirred rapidly and was heated at reflux overnight. The mixture was transferred to a separatory funnel and the layers were separated. The aqueous layer was extracted with dichloromethane. The combined organic layers were filtered through CELITE filter agent, dried over magnesium sulfate, filtered, and concentrated to a dark oil. The crude product was purified by suction filter chromatography (silica gel, gradient elution from 3:1 to 1:3 hexanes/ethyl acetate, then 4:1 dichloromethane/ethyl acetate) to afford pure product $N^4$-allyl-2-chloroquinoline-3,4-diamine (12.06 g) along with some impure product (3.10 g).

Part C

Ethoxyacetyl chloride (8.80 g, 71.8 mmol) was added dropwise to a solution of $N^4$-allyl-2-chloroquinoline-3,4-diamine (15.2 g, 65.3 mmol) in acetonitrile (300 mL) at room temperature. After 45 minutes, the reaction mixture was filtered and an orange solid (approximately 17 g) was isolated. The solid was dissolved in a solution of ethanol (240 mL) and water (80 mL). Sodium hydroxide (3.92 g, 98.0 mmol) was added and the solution was heated at reflux for 2 hours. The ethanol was removed under reduced pressure and the remaining aqueous solution was extracted several times with dichloromethane. The combined organic layers were dried over magnesium sulfate, filtered, and concentrated to an orange solid. The solid was triturated with ethyl acetate and isolated by filtration to yield 6 g of a pale yellow solid. The filtrate was concentrated and purified by suction filter chromatography (silica gel with 97:3 dichloromethane/methanol as the eluent) to yield an additional 5 g of product. The material was combined to provide 11 g of 1-allyl-4-chloro-2-(ethoxymethyl)-1H-imidazo[4,5-c]quinoline.

Part D

To a 0° C. solution of acetaldehyde oxime (1.22 mL, 20.0 mmol) in N,N-dimethylformamide (DMF, 20 mL) was added N-chlorosuccinimide (2.67 g, 20.0 mmol) over a period of 10 minutes. After 15 minutes, the solution was warmed to 50° C. for 1 hour. After cooling to room temperature, the solution was partitioned between ice water and ethyl acetate. The aqueous layer was extracted with two additional portions of ethyl acetate. The combined organic layers were washed with water and brine, dried over magnesium sulfate, filtered, and concentrated to provide N-hydroxyethanimidoyl chloride as a pale yellow oil.

Part E

Triethylamine (1.04 mL, 7.46 mmol) was added to a 0° C. solution of 1-allyl-4-chloro-2-(ethoxymethyl)-1H-imidazo[4,5-c]quinoline (1.50 g, 4.97 mmol) and N-hydroxyethanimidoyl chloride (581 mg, 6.21 mmol) in dichloromethane (80 mL). The reaction solution was allowed to warm slowly to room temperature and stir overnight under a nitrogen atmosphere. After 20 hours, the solution was washed with saturated aqueous sodium bicarbonate and brine, dried over magnesium sulfate, filtered, and concentrated. The crude product was purified by flash chromatography (silica gel, elution with 98:2 dichloromethane/methanol) to yield 4-chloro-2-(ethoxymethyl)-1-[(3-methyl-4,5-dihydroisoxazol-5-yl)methyl]-1H-imidazo[4,5-c]quinoline (1.34 g) as a white solid.

Part F

4-Chloro-2-(ethoxymethyl)-1-[(3-methyl-4,5-dihydroisoxazol-5-yl)methyl]-1H-imidazo[4,5-c]quinoline (1.30 g, 3.62 mmol) was treated with a solution of 7 M ammonia in methanol (60 mL), and the mixture was sealed in a pressure vessel and heated at 150° C. for 24 hours. The volatiles were removed under reduced pressure, and the residue was partitioned between saturated aqueous sodium bicarbonate and dichloromethane. The aqueous layer was extracted with two additional portions of dichloromethane. The combined organic layers were washed with brine, dried over magnesium sulfate, filtered, and concentrated. The crude product was purified by flash chromatography (silica gel, gradient elution using 98:2 to 96:4 dichloromethane/methanol) to afford 2-(ethoxymethyl)-1-[(3-methyl-4,5-dihydroisoxazol-5-yl)methyl]-1H-imidazo[4,5-c]quinolin-4-amine (1.10 g) as a white solid that was crystallized from acetonitrile to provide white needles, mp 204-205° C.

$^1$H NMR (300 MHz, CDCl$_3$) δ 7.90 (dd, J=8.2, 0.8 Hz, 1H), 7.83 (dd, J=8.4, 0.9 Hz, 1H), 7.53 (dt, J=7.1, 1.3 Hz, 1H), 7.32 (dt, J=8.2, 1.2 Hz, 1H), 5.46 (br s, 2H), 5.14 (m, 1H), 4.96 (d, J=12.7 Hz, 1H), 4.88 (dd, J=15.4, 7.7 Hz, 1H), 4.81 (d, J=12.7 Hz, 1H), 4.72 (dd, J=15.4, 4.4 Hz, 1H), 3.62 (q, J=7.0 Hz, 2H), 3.12 (dd, J=16.9, 10.6 Hz, 1H), 2.86 (dd, J=17.2, 6.5 Hz, 1H), 2.01 (s, 3H), 1.24 (t, J=7.0 Hz, 3H).

MS (APCI) m/z 340 (M+H$^+$).

Anal. calcd for C$_{18}$H$_{21}$N$_5$O$_2$: C, 63.70; H, 6.24; N, 20.63. Found: C, 63.44; H, 6.15; N, 21.00.

Example 2

2-(Ethoxymethyl)-1-[(3-phenyl-4,5-dihydroisoxazol-5-yl)methyl]-1H-imidazo[4,5-c]quinolin-4-amine

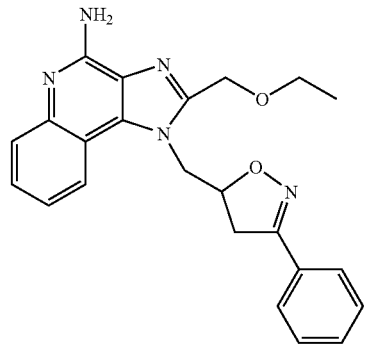

Part A

N-Hydroxybenzenecarboximidoyl chloride (13.7 g) was prepared according to the method described in Part D of Example 1 by reacting benzaldehyde oxime (11.5 g, 94.9 mmol) in DMF (20 mL) with N-chlorosuccinimide (12.6 g, 94.9 mmol) and was obtained as a white solid. Triethylamine (0.69 mL, 4.97 mmol) was added to a solution of N-hydroxybenzenecarboximidoyl chloride (644 mg, 4.14 mmol) and 1-allyl-4-chloro-2-(ethoxymethyl)-1H-imidazo[4,5-c]quinoline (prepared as described in Part C of Example 1, 1.00 g, 3.32 mmol) in dichloromethane (50 mL) at room temperature. The solution was stirred overnight and then was washed with saturated aqueous sodium bicarbonate, dried over magnesium sulfate, filtered, and concentrated. The crude product was purified by flash chromatography on silica gel to afford 4-chloro-2-(ethoxymethyl)-1-[(3-phenyl-4,5-dihydroisoxazol-5-yl)methyl]-1H-imidazo[4,5-c]quinoline as a pale yellow solid (1.19 g).

Part B

4-Chloro-2-(ethoxymethyl)-1-[(3-phenyl-4,5-dihydroisoxazol-5-yl)methyl]-1H-imidazo[4,5-c]quinoline (1.50 g, 3.56 mmol) was treated with a solution of 7 M ammonia in methanol (30 mL) at 140° C. for 15 hours according to the method described in Part F of Example 1. Chloroform was used in the work-up procedure instead of dichloromethane. The crude product was purified by flash chromatography (silica gel, elution with 97:3 dichloromethane/methanol) to afford 2-(ethoxymethyl)-1-[(3-phenyl-4,5-dihydroisoxazol-5-yl)methyl]-1H-imidazo[4,5-c]quinolin-4-amine (1.17 g) as a yellow solid. Recrystallization afforded white needles, mp 235-237° C.

$^1$H NMR (300 MHz, CDCl$_3$) δ 7.97 (dd, J=8.2, 0.9 Hz, 1H), 7.84 (dd, J=8.4, 1.0 Hz, 1H), 7.67-7.64 (m, 2H), 7.53 (ddd, J=8.4, 7.1, 1.3 Hz, 1H), 7.46-7.38 (m, 3H), 7.31 (ddd, J=8.2, 7.1, 1.3 Hz, 1H), 5.41 (br s, 2H), 5.37-5.34 (m, 1H), 5.02-4.77 (m, 4H), 3.59 (q, J=7.0 Hz, 2H), 3.53 (m, 1H), 3.34 (dd, J=16.8, 6.3 Hz, 1H), 1.18 (t, J=7.0 Hz, 3H).

MS (APCI) m/z 402 (M+H$^+$).

Anal. calcd for C$_{23}$H$_{23}$N$_5$O$_2$: C, 68.81; H, 5.77; N, 17.44. Found: C, 68.71; H, 5.91; N, 17.44.

Example 3

2-(Ethoxymethyl)-1-[(3-phenylisoxazol-5-yl)methyl]-1H-imidazo[4,5-c]quinolin-4-amine

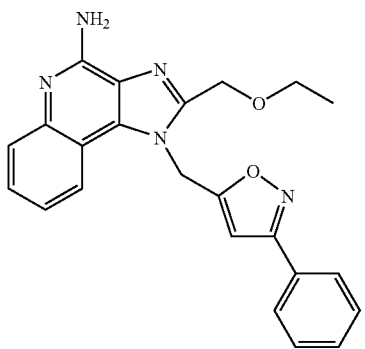

Part A

Propargylamine (25 mL, 0.36 mol) was added dropwise over a period of five minutes to a 4.5° C. solution of 2,4-dichloro-3-nitroquinoline (84.4 g, 0.347 mol) and triethylamine (73 mL, 0.52 mol) in dichloromethane (1.2 L). After one hour, the solution was allowed to warm to room temperature. After several days, the solvent was evaporated under reduced pressure and the resulting solid was triturated with water and isolated by filtration. The solid was rinsed with water and toluene (500 mL), then was dissolved in dichloromethane and toluene and concentrated under reduced pressure to remove residual water. The solid was dissolved in methanol and ether and concentrated under reduced pressure to afford 2-chloro-3-nitro-N-prop-2-ynylquinolin-4-amine as yellow-brown solid (79.5 g) that contained some impurities and was used without further manipulation.

Part B

An aqueous solution (1.5 L) of sodium dithionate (265 g, 1.52 mol) was added to a solution of 2-chloro-3-nitro-N-prop-2-ynylquinolin-4-amine (79.3 g, 0.303 mol) in ethanol (750 mL) and acetonitrile (950 mL). A fine white precipitate formed within seconds. The reaction was worked-up after thin layer chromatography (TLC) analysis of the reaction mixture indicated that the reaction was complete. The solids were removed by filtration and the filter cake was rinsed with dichloromethane. The filtrate was concentrated under reduced pressure to remove the volatiles, leaving an aqueous solution that was extracted with several portions of dichloromethane. The organic layers were combined, washed with brine, dried over magnesium sulfate, filtered, and concentrated to yield 2-chloro-N$^4$-prop-2-ynylquinoline-3,4-diamine (43.5 g) that was approximately 60% pure and was used without further purification.

Part C

Ethoxyacetyl chloride (89%, 28 g, 0.20 mol) was added dropwise to a solution of 2-chloro-N$^4$-prop-2-ynylquinoline-3,4-diamine (43.5 g, 0.188 mol) and triethylamine (39 mL, 0.28 mol) in dichloromethane (600 mL) at 6° C. After two hours, the reaction mixture was diluted with dichloromethane and washed with saturated aqueous sodium bicarbonate. The aqueous layer was back-extracted with dichloromethane three times. The organic layers were combined and washed twice with water and brine, dried over magnesium sulfate, filtered, and concentrated under reduced pressure. The resulting brown solid was triturated with toluene with heating. A fine tan solid was isolated by filtration, rinsed with diethyl ether, and dried to yield N-[2-chloro-4-(prop-2-ynylamino)quinolin-3-yl]-2-ethoxyacetamide (47.2 g).

Part D

A solution of N-[2-chloro-4-(prop-2-ynylamino)quinolin-3-yl]-2-ethoxyacetamide (26.7 g, 84.0 mmol) and triethylamine (17.5 mL, 126 mmol) in ethanol (250 mL) was heated at 60° C. for 1.7 days. Additional triethylamine (17.5 mL) was added and the solution was heated at 60° C. for two more days. The volatiles were removed under reduced pressure and the resulting white solid was triturated with water, isolated by filtration, and dried to provide 4-chloro-2-(ethoxymethyl)-1-prop-2-ynyl-1H-imidazo[4,5-c]quinoline (24.2 g, 96%).

Part E

N-Hydroxybenzenecarboximidoyl chloride (prepared as described in Part A of Example 2, 1.72 g, 10.5 mmol) was added to a solution of 4-chloro-2-(ethoxymethyl)-1-prop-2-ynyl-1H-imidazo[4,5-c]quinoline (3.00 g, 10.0 mmol) and triethylamine (1.70 mL, 12.0 mmol) in dichloromethane (40 mL). The solution was heated at reflux under a nitrogen atmosphere for 3.5 hours and additional N-hydroxybenzenecarboximidoyl chloride (0.1 g) was added. The solution was heated at reflux for one hour more, then was allowed to cool to room temperature and was diluted with dichloromethane. The solution was transferred to a separatory funnel and was washed with water and brine, dried over sodium sulfate, filtered, and concentrated. The crude product was purified by flash chromatography (silica gel, gradient elution from 4:1 to 3:2 hexanes/ethyl acetate) to provide pure 4-chloro-2-(ethoxymethyl)-1-[(3-phenylisoxazol-5-yl)methyl]-1H-imidazo[4,5-c]quinoline (1.48 g).

Part F

4-Chloro-2-(ethoxymethyl)-1-[(3-phenylisoxazol-5-yl)methyl]-1H-imidazo[4,5-c]quinoline (1.48 g, 3.53 mmol) was treated with a solution of 7 M ammonia in methanol (25 mL) at 150° C. for 17 hours. The volatiles were removed under reduced pressure and the resulting oil was diluted with dichloromethane and 1 M hydrochloric acid. A white solid formed and 50% aqueous sodium hydroxide was added to dissolve the solid. The aqueous layer was separated and extracted with dichloromethane. The organic layers were combined, washed with brine, dried over magnesium sulfate, filtered, and concentrated to an oil. Upon treatment of the oil with diethyl ether, a solid formed. The solid was purified by flash chromatography (silica gel, eluting with a mixture of 95% dichloromethane and 5% of a solution of 80% chloroform, 18% methanol, and 2% NH$_4$OH (CMA)) followed by several recrystallizations from acetonitrile to provide 2-(ethoxymethyl)-1-[(3-phenylisoxazol-5-yl)methyl]-1H-imidazo[4,5-c]quinolin-4-amine (0.505 g) as a white powder, mp 215.0-216.0° C.

$^1$H NMR (300 MHz, DMSO-d$_6$) δ 7.98 (d, J=7.6 Hz, 1H), 7.79 (m, 2H), 7.61 (d, J=7.5 Hz, 1H), 7.38-7.43 (m, 4H), 7.17 (t, J=7.5, 1H), 6.85 (s, 1H), 6.69 (s, 2H), 6.15 (s, 2H), 4.88 (s, 2H), 3.50 (q, J=6.9, 2H), 0.99 (t, J=6.9 Hz, 3H).

MS (APCI) m/z 400 (M+H)$^+$.

Anal. calcd for C$_{23}$H$_{21}$N$_5$O$_2$: C, 69.16; H, 5.30; N, 17.53. Found: C, 69.29; H, 5.22; N, 17.65.

Example 4

2-(Ethoxymethyl)-1-[(3-methylisoxazol-5-yl)methyl]-1H-imidazo[4,5-c]quinolin-4-amine

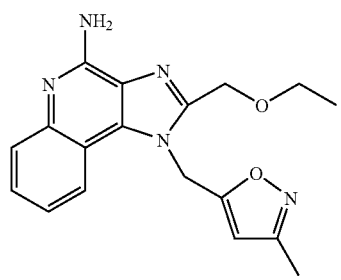

Part A

N-Hydroxyethanimidoyl chloride (prepared as described in Part D of Example 1, 2.10 g, 22.5 mmol) was added to a solution of 4-chloro-2-(ethoxymethyl)-1-prop-2-ynyl-1H-imidazo[4,5-c]quinoline prepared as described in Part D of Example 3, 5.39 g, 18.0 mmol) and triethylamine (3.70 mL, 27.0 mmol) in dichloromethane (60 mL). The solution was heated at reflux for 16 hours and then was concentrated under reduced pressure. The crude product was purified by flash chromatography (silica gel, gradient elution from 7:3 to 2:3 hexanes/ethyl acetate) to provide 4-chloro-2-(ethoxymethyl)-1-[(3-methylisoxazol-5-yl)methyl]-1H-imidazo[4,5-c]quinoline (4.21 g) as a white solid.

Part B

A slurry of 4-chloro-2-(ethoxymethyl)-1-[(3-methylisoxazol-5-yl)methyl]-1H-imidazo[4,5-c]quinoline (4.21 g, 11.8 mmol) in a solution of 7 M ammonia in methanol (50 mL) was heated at 150° C. for 22 hours in a Parr pressure vessel. The volatiles were removed under reduced pressure and the resulting solid was triturated with water. A tan solid was isolated and purified by flash chromatography (silica gel, gradient elution from 9:1 to 1:1 chloroform/CMA) to yield 43.2 mg of pure 2-(ethoxymethyl)-1-[(3-methylisoxazol-5-yl)methyl]-1H-imidazo[4,5-c]quinolin-4-amine as a white powder, mp 178.0-180.0° C.

$^1$H NMR (300 MHz, DMSO-d$_6$) δ 7.93 (d, J=7.5 Hz, 1H), 7.60 (d, J=7.5 Hz, 1H), 7.41 (t, J=7.1 Hz, 1H), 7.16 (t, J=7.0 Hz, 1H), 6.69 (s, 2H), 6.10 (s, 1H), 6.04 (s, 2H), 4.83 (s, 2H), 3.48 (q, J=7.0 Hz, 2H), 2.11 (s, 3H), 1.05 (t, J=7.0, 3H).

MS (APCI) m/z 338 (M+H)$^+$.

Anal. calcd for C$_{18}$H$_{19}$N$_5$O$_2$: C, 64.08; H, 5.68; N, 20.76. Found: C, 63.74; H, 5.43; N, 20.42.

Example 5

2-(Ethoxymethyl)-1-[(3-pyridin-3-ylisoxazol-5-yl)methyl]-1H-imidazo[4,5-c]quinolin-4-amine

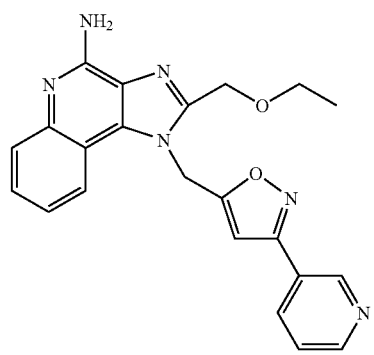

Part A

3-Pyridinecarboxaldehyde oxime was prepared by treating 3-pyridinecarboxaldehyde (10 mL, 106 mmol) with hydroxylamine hydrochloride (8.10 g, 117 mmol) and 50% aqueous sodium hydroxide (2 mL) in ethanol (100 mL) and water (200 mL) for 17 hours. The solution was adjusted to pH 14 with the addition of 50% (w/w) aqueous sodium hydroxide. The solution was extracted with several portions of dichloromethane. The combined organic layers were washed with brine, dried over magnesium sulfate, filtered, and concentrated under reduced pressure to yield 8.3 g of a white solid. The aqueous layers were combined and back-extracted with chloroform (5×1 L) to yield additional product. The total amount of 3-pyridinecarboxaldehyde oxime obtained was 12.24 g.

Part B

N-Chlorosuccinimide (1.09 g, 8.19 mmol) was added to a 6° C. solution of 3-pyridinecarboxaldehyde oxime (1.00 g, 8.19 mmol) in tetrahydrofuran (THF) (25 mL). The solution was heated at 50° C. for 2 h. 4-Chloro-2-(ethoxymethyl)-1-prop-2-ynyl-1H-imidazo[4,5-c]quinoline (prepared as described in Part D of Example 3, 1.96 g, 6.55 mmol) and triethylamine (1.70 mL, 12.3 mmol) were added to the reaction, which was heated at 50° C. for 17 hours. The volatiles were removed under reduced pressure and the residue was partitioned between dichloromethane and saturated aqueous potassium carbonate. The aqueous layer was extracted multiple times with dichloromethane and chloroform. The organic layers were combined, dried over sodium sulfate, filtered, and concentrated. The crude product was purified by flash chromatography (silica gel, gradient elution with 1:1 to 1:4 hexanes/ethyl acetate) to yield 4-chloro-2-(ethoxymethyl)-1-[(3-pyridin-3-ylisoxazol-5-yl)methyl]-1H-imidazo[4,5-c]quinoline (1.52 g).

Part C

A slurry of 4-chloro-2-(ethoxymethyl)-1-[(3-pyridin-3-ylisoxazol-5-yl)methyl]-1H-imidazo[4,5-c]quinoline (1.52 g, 3.62 mmol) in a solution of 7 M ammonia in methanol (15 mL) was heated at 150° C. for 20 hours in a Parr pressure vessel. The volatiles were removed under reduced pressure and the resulting residue was partitioned between dichloromethane and 1 M aqueous sodium hydroxide. The aqueous layer was extracted with several portions of dichloromethane.

The organic phases were combined, washed with brine, dried over magnesium sulfate, filtered, and concentrated under reduced pressure. The crude product was purified by flash chromatography (silica gel, gradient elution 10% to 30% CMA/chloroform) to yield 2-(ethoxymethyl)-1-[(3-pyridin-3-ylisoxazol-5-yl)methyl]-1H-imidazo[4,5-c]quinolin-4-amine (653 mg, 45%) as white powder that was dried under vacuum at 70° C., mp 240.0-242.0° C. $^1$H NMR (300 MHz, DMSO-d$_6$) δ 8.99 (d, J=1.7 Hz, 1H), 8.64 (dd, J=3.2, 1.6 Hz, 1H), 8.16-8.20 (m, 1H), 7.97 (d, J=7.5 Hz, 1H), 7.61 (d, J=7.4 Hz, 1H), 7.41-7.50 (m, 2H), 7.17 (t, J=7.0 Hz, 1H), 6.97 (s, 1H), 6.17 (s, 2H), 5.75 (s, 2H), 4.88 (s, 2H), 3.50 (q, J=7.0 Hz, 2H), 0.98 (t, J=7.0, 3H).

MS (APCI) m/z 401 (M+H)$^+$.

Anal. calcd for $C_{22}H_{20}N_6O_2 \cdot 0.1CH_2Cl_2$: C, 64.91; H, 4.98; N, 20.55. Found: C, 64.70; H, 4.95; N, 20.70.

Example 6

2-(Ethoxymethyl)-1-[3-(3-pyridin-3-ylisoxazol-5-yl)propyl]-1H-imidazo[4,5-c]quinolin-4-amine

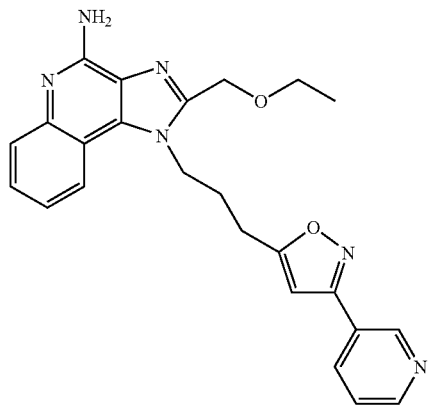

Part A p-Toluenesulfonyl chloride (21.4 g, 112 mmol) was added slowly to a stirred solution of 4-pentyn-1-ol (11.5 mL, 124 mL) and triethylamine (17.2 mL, 124 mmol) in dichloromethane (100 mL) at room temperature. After 22 hours, the solution was diluted with dichloromethane, washed with water, dried over sodium sulfate, filtered, and concentrated. The crude product was purified by flash chromatography (silica gel, gradient elution from 95:5 to 85:15 hexanes/ethyl acetate) to afford the product pent-4-ynyl 4-methylbenzenesulfonate (23.4 g, 87%) as a colorless oil.

Part B

A mixture of pent-4-ynyl 4-methylbenzenesulfonate (23.4 g, 98.2 mmol) and sodium azide (16.6 g, 255 mmol) in DMF (80 mL) was heated at 60° C. for 3.5 hours. The reaction was allowed to cool to room temperature and water was added until the remaining sodium azide dissolved. The solution was extracted with several portions of diethyl ether. The combined organic layers were washed with water, dried over magnesium sulfate, filtered, and concentrated to an oil. The oil was dissolved in diethyl ether (80 mL) and cooled to 0° C. Triphenylphosphine (25.8 g, 98.2 mmol) was added and gas evolution was observed. After 19 hours, water (10 mL) and tetrahydrofuran (50 mL) were added and the mixture was stirred for 20 hours at room temperature. The mixture was partitioned between 1 M hydrochloric acid (400 mL) and dichloromethane (400 mL). The aqueous phase was washed with dichloromethane. The aqueous phase was concentrated under reduced pressure to a white solid that was crystallized from ethanol/water to yield pent-4-yn-1-amine hydrochloride as a white powder (8.15 g).

Part C

Pent-4-yn-1-amine hydrochloride (5.48 g, 45.8 mmol) was added to a 6° C. solution of 2,4-dichloro-3-nitroquinoline (10.6 g, 43.6 mmol) and triethylamine (15.2 mL, 109 mmol) in dichloromethane (100 mL). After 30 minutes, the solution was allowed to warm to room temperature. After 5 hours, the volatiles were removed under reduced pressure and the solid residue was triturated with water and isolated by filtration. The filter cake was rinsed with water and toluene and was allowed to dry for several days to yield 2-chloro-3-nitro-N-pent-4-ynylquinolin-4-amine as an orange solid (13.16 g).

Part D

An aqueous solution (125 mL) of sodium dithionate (38.0 g, 218 mmol) was added to a solution of 2-chloro-3-nitro-N-pent-4-ynylquinolin-4-amine (12.64 g, 43.63 mmol) in ethanol (15 mL) and acetonitrile (130 mL). A fine white precipitate formed within seconds. After 2.5 hours, the volatiles were removed under reduced pressure leaving a yellow aqueous mixture that was diluted with water (1 L) and washed with dichloromethane (250 mL×3). The organic layers were combined, washed with water and brine, dried over magnesium sulfate, filtered, and concentrated to yield 2-chloro-N$^4$-pent-4-ynylquinoline-3,4-diamine as an amber oil (8.10 g) that was used without further purification.

Part E

Ethoxyacetyl chloride (96%, 4.40 g, 34.3 mmol) was added to a 6° C. solution of 2-chloro-N$^4$-pent-4-ynylquinoline-3,4-diamine (8.10 g, 31.2 mmol) and triethylamine (6.50 mL, 46.8 mmol) in dichloromethane (100 mL). Additional ethoxyacetyl chloride (3.0 g) was added after 45 minutes until all the starting material had been consumed. The solution was diluted with dichloromethane and washed with saturated aqueous potassium carbonate, water, and brine, dried over potassium carbonate, filtered, and concentrated to afford N-[2-chloro-4-(pent-4-ynylamino)quinolin-3-yl]-2-ethoxyacetamide as a pale yellow solid (10.23 g).

Part F

A solution of N-[2-chloro-4-(pent-4-ynylamino)quinolin-3-yl]-2-ethoxyacetamide (10.23 g, 29.58 mmol) and 6 M aqueous potassium carbonate (7.40 mL, 44.4 mmol) in 9:1 ethanol/water (100 mL) was heated at 50° C. for 16 hours. The volatiles were removed under reduced pressure and the resulting slurry was partitioned between ethyl acetate and water. The organic phase was washed with water (2×) and brine (2×), dried over magnesium sulfate, filtered, and concentrated to afford 4-chloro-2-(ethoxymethyl)-1-pent-4-ynyl-1H-imidazo[4,5-c]quinoline as a slightly impure tan solid (9.5 g).

Part G

4-Chloro-2-(ethoxymethyl)-1-pent-4-ynyl-1H-imidazo[4,5-c]quinoline (3.65 g, 11.1 mmol) was converted to 4-chloro-2-(ethoxymethyl)-1-[3-(3-pyridin-3-ylisoxazol-5-yl)propyl]-1H-imidazo[4,5-c]quinoline (1.78 g, 36%) following the method described in Parts A and B of Example 5.

Part H

A slurry of 4-chloro-2-(ethoxymethyl)-1-[3-(3-pyridin-3-ylisoxazol-5-yl)propyl]-1H-imidazo[4,5-c]quinoline (1.78 g, 3.97 mmol) in a solution of 7 M ammonia in methanol (20 mL) was heated at 150° C. for 20 hours in a Parr pressure vessel. The volatiles were removed under reduced pressure and the resulting oil was partitioned between dichloromethane and 1 M KOH. The aqueous layer was extracted with dichloromethane. The organic layers were combined, washed with water and brine, dried over magnesium sulfate, filtered, and concentrated. The crude product was purified by flash chromatography (silica gel, gradient elution from 9:1 to 4:1 chloroform/CMA). After concentration of the appropriate fractions, a white solid was obtained. The white solid was triturated with diethyl ether and dried at 80° C. under vacuum to provide 2-(ethoxymethyl)-1-[3-(3-pyridin-3-ylisoxazol-5-yl)propyl]-1H-imidazo[4,5-c]quinolin-4-amine as a white powder, mp 199.0-200.0° C.

$^1$H NMR (300 MHz, DMSO-$d_6$) δ 8.99 (d, J=2.5 Hz, 1H), 8.66 (dd, J=3.2, 1.7 Hz, 1H), 8.13 (dt, J=8.2, 1.9 Hz, 1H), 7.83 (t, J=8.0 Hz, 2H), 7.51 (t, J=7.1 Hz, 1H), 7.40 (m, 1H), 7.29 (t, J=7.0 Hz, 1H), 6.44 (s, 1H), 5.45 (s, 2H), 4.80 (s, 2H), 4.68 (t, J=7.9 Hz, 2H), 3.61 (q, J=7.0 Hz, 2H), 3.06 (t, J=7.3 Hz, 2H), 2.47 (m, 2H), 1.23 (t, J=7.0, 3H).

MS (APCI) m/z 429 (M+H)$^+$.

Anal. calcd for $C_{24}H_{24}N_6O_2 \cdot 0.4H_2O$: C, 66.16; H, 5.74; N, 19.29. Found: C, 66.53; H, 5.70; N, 18.93.

Example 7

2-(Ethoxymethyl)-1-[3-(3-phenylisoxazol-5-yl)propyl]-1H-imidazo[4,5-c]quinolin-4-amine

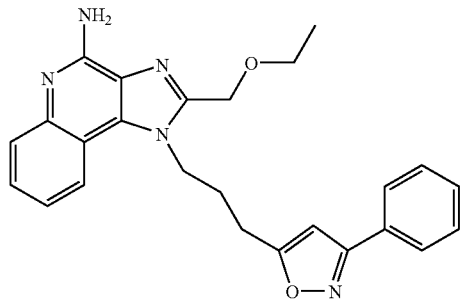

Part A

N-Hydroxybenzenecarboximidoyl chloride (prepared as described in Part A of Example 2, 2.61 g, 16.8 mmol) was added to a solution of 4-chloro-2-(ethoxymethyl)-1-pent-4-ynyl-1H-imidazo[4,5-c]quinoline (prepared as described in Part F of Example 6, 2.90 g, 8.39 mmol) and triethylamine (3.50 mL, 25.2 mmol) in dichloromethane at 6° C. The solution was heated at 50° C. under a nitrogen atmosphere for 4 hours. The solution was diluted with dichloromethane, transferred to a separatory funnel, washed with water and brine, dried over sodium sulfate, filtered, and concentrated to an oil. The oil was triturated with hexanes and the solvent was decanted. The oil was triturated with diethyl ether and a solid formed that was isolated by filtration to provide 4-chloro-2-(ethoxymethyl)-1-[3-(3-phenylisoxazol-5-yl)propyl]-1H-imidazo[4,5-c]quinoline (1.98 g). The filtrate was purified by flash chromatography (silica gel, gradient elution from 7:3 to 1:1 hexanes/ethyl acetate) to provide an additional 0.24 g of product. The total amount of 4-chloro-2-(ethoxymethyl)-1-[3-(3-phenylisoxazol-5-yl)propyl]-1H-imidazo[4,5-c]quinoline isolated was 2.22 g.

Part B

A mixture of 4-chloro-2-(ethoxymethyl)-1-[3-(3-phenylisoxazol-5-yl)propyl]-1H-imidazo[4,5-c]quinoline (2.22 g, 4.97 mmol) in a solution of 7 M ammonia in methanol (25 mL) was heated at 150° C. for 17 hours in a Parr pressure vessel. The volatiles were removed under reduced pressure and the resulting solid was triturated with 1 M aqueous sodium hydroxide and isolated by filtration. The crude product was purified by flash chromatography (silica gel, gradient elution from 10% to 20% CMA in chloroform). The appropriate fractions were combined and concentrated to yield a solid that was triturated with hot diethyl ether and 9:1 dichloromethane/methanol (10 mL). The final material was dried at 80° C. under vacuum to yield 2-(ethoxymethyl)-1-[3-(3-phenylisoxazol-5-yl)propyl]-1H-imidazo[4,5-c]quinolin-4-amine (954 mg) as a white powder, mp 171.0-172.0° C.

$^1$H NMR (300 MHz, DMSO-$d_6$) δ 7.99 (d, J=7.7 Hz, 1H), 7.83-7.85 (m, 2H), 7.62 (d, J=7.4 Hz, 1H), 7.46-7.52 (m, 3H), 7.46 (t, J=8.1 Hz, 1H), 7.21 (t, J=7.0 Hz, 1H), 6.90 (s, 1H), 6.60 (s, 2H), 4.77 (s, 2H), 4.68 (t, J=7.8 Hz, 2H), 3.53 (q, J=7.0 Hz, 2H), 3.09 (t, J=7.4 Hz, 2H), 2.30 (m, 2H), 1.12 (t, J=7.0 Hz, 3H).

MS (APCI) m/z 428 (M+H)$^+$.

Anal. calcd for $C_{25}H_{25}N_5O_2$: C, 70.24; H, 5.89; N, 16.38. Found: C, 69.97; H, 6.02; N, 16.52.

Example 8

2-(Ethoxymethyl)-1-[3-(3-methylisoxazol-5-yl)propyl]-1H-imidazo[4,5-c]quinolin-4-amine

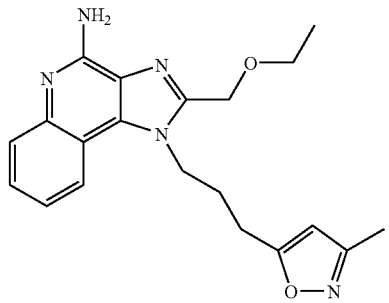

Part A

In the presence of triethylamine (5.2 mL, 10.7 mmol) in a solution of THF (50 mL), 4-chloro-2-(ethoxymethyl)-1-pent-4-ynyl-1H-imidazo[4,5-c]quinoline (prepared as described in Part F of Example 6, 3.50 g, 10.7 mmol) was reacted with N-hydroxyethanimidoyl chloride that was generated from acetaldehyde oxime (1.90 g, 32.1 mmol) and N-chlorosuccinimide (4.30 g, 32.1 mmol) using the method described in Part B of Example 5. The crude product was purified by flash chromatography (silica gel, gradient elution with 4:1 to 2:3 hexanes/ethyl acetate). The appropriate fractions were combined and concentrated to provide a solid that was triturated with diethylether. The solid was isolated by filtration and dried to yield 4-chloro-2-(ethoxymethyl)-1-[3-(3-methylisoxazol-5-yl)propyl]-1H-imidazo[4,5-c]quinoline (1.87 g) as a white solid.

Part B

4-Chloro-2-(ethoxymethyl)-1-[3-(3-methylisoxazol-5-yl)propyl]-1H-imidazo[4,5-c]quinoline (1.87 g, 4.86 mmol) was treated with a solution of 7 M ammonia in methanol (20 mL) according to the procedure described in Part C of Example 5. The crude product was purified by flash chromatography (silica gel, gradient elution from 5% to 20% CMA in chloroform). The appropriate fractions were combined and concentrated to yield a solid that was triturated with 9:1 dichloromethane/methanol. The final material was dried under vacuum to yield 2-(ethoxymethyl)-1-[3-(3-methylisoxazol-5-yl)propyl]-1H-imidazo[4,5-c]quinolin-4-amine (1.29 mg) as a white powder, mp 163.0-164.0° C.

$^1$H NMR (300 MHz, DMSO-d$_6$) δ 7.95 (d, J=8.1 Hz, 1H), 7.62 (d, J=7.6 Hz, 1H), 7.44 (t, J=7.4 Hz, 1H), 7.22 (t, J=7.5 Hz, 1H), 6.59 (s, 2H), 6.18 (s, 1H), 4.75 (s, 2H), 4.62 (t, J=7.7 Hz, 2H), 3.53 (q, J=7.0 Hz, 2H), 2.96 (t, J=7.4 Hz, 2H), 2.23 (m, 5H), 1.14 (t, J=7.0 Hz, 3H).

MS (APCI) m/z 366 (M+H)$^+$.

Anal. calcd for C$_{20}$H$_{23}$N$_5$O$_2$: C, 65.74; H, 6.34; N, 19.16. Found: C, 65.41; H, 6.41; N, 19.15.

Example 9

2-(Ethoxymethyl)-6,7-dimethyl-1-[(3-pyridin-3-yl-isoxazol-5-yl)methyl]-1H-imidazo[4,5-c]pyridin-4-amine

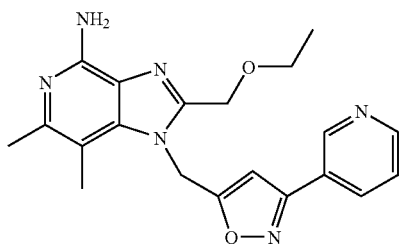

Part A

To dichloromethane (10 mL) at –78° C. was added dimethylsulfoxide (0.37 mL, 5.17 mmol) and oxalyl chloride (0.33 mL, 3.79 mmol). After several minutes, a solution of 2-[8-(ethoxymethyl)-5,6-dimethyl-7H-imidazo[4,5-c]tetraazolo[1,5-a]pyridin-7-yl]ethanol (prepared as described in U.S. Pat. No. 6,797,718, 1.00 g, 3.44 mmol) in dichloromethane (40 mL) was added dropwise followed by triethylamine (1.5 mL, 10.3 mmol). The mixture was allowed to warm to room temperature and more dichloromethane (80 mL) was added. The solution was transferred to a separatory funnel and washed with saturated aqueous potassium carbonate, water, and brine. The aqueous layers were combined and back-extracted with dichloromethane. The organic phases were combined, dried over sodium sulfate, filtered, and concentrated under reduced pressure to yield the product [8-(ethoxymethyl)-5,6-dimethyl-7H-imidazo[4,5-c]tetraazolo[1,5-a]pyridin-7-yl]acetaldehyde as a tan solid (0.86 g).

Part B

Diethyl 1-diazo-2-oxopropylphosphonate (0.90 g, 3.6 mmol) was prepared by the method of Bestmann, H. J. et al., *Synlett*, pp. 521-522 (1996) and added to a mixture of [8-(ethoxymethyl)-5,6-dimethyl-7H-imidazo[4,5-c]tetraazolo[1,5-a]pyridin-7-yl]acetaldehyde (0.86 g, 3.0 mmol) and potassium carbonate (0.82 g, 6.0 mmol) in methanol (10 mL) at room temperature. After 2.5 hours, the reaction was filtered and the filter cake was rinsed with a mixture of dichloromethane and methanol. The filtrate was diluted with dichloromethane and washed with water (2×) and brine (2×). The aqueous phases were combined and back-extracted with dichloromethane. The organic portions were combined, dried over magnesium sulfate, filtered, and concentrated. The yellow solid was triturated with diethyl ether and dried under vacuum to provide the slight impure product 8-(ethoxymethyl)-5,6-dimethyl-7-prop-2-ynyl-7H-imidazo[4,5-c]tetraazolo[1,5-a]pyridine (0.442 g) that was used without further purification.

Part C

In the presence of triethylamine (0.50 mL, 3.4 mmol), 8-(ethoxymethyl)-5,6-dimethyl-7-prop-2-ynyl-7H-imidazo[4,5-c]tetraazolo[1,5-a]pyridine (0.442 g, 1.55 mmol) was reacted with N-hydroxypyridine-3-carboximidoyl chloride generated from 3-pyridinecarboxyaldehyde oxime (prepared as described in Part A of Example 5, 0.38 g, 3.11 mmol) and N-chlorosuccinimide (0.42 g, 3.11 mmol) in THF (5 mL) using the method described in Part B of Example 5. After purification by flash chromatography (silica gel, elution with 95:5 dichloromethane/methanol) and trituration in diethyl ether, the product 8-(ethoxymethyl)-5,6-dimethyl-7-[(3-pyridin-3-ylisoxazol-5-yl)methyl]-7H-imidazo[4,5-c]tetraazolo[1,5-a]pyridine was obtained (0.171 g) as a white powder.

Part D

A mixture of 8-(ethoxymethyl)-5,6-dimethyl-7-[(3-pyridin-3-ylisoxazol-5-yl)methyl]-7H-imidazo[4,5-c]tetraazolo[1,5-a]pyridine (0.1712 g, 0.423 mmol) and triphenylphosphine (0.120 g, 0.466 mmol) in toluene (2 mL) was heated at reflux for five days. The solvent was removed and the resulting brown solvent was dissolved in 1 M hydrogen chloride in methanol (5 mL). The solution was heated at reflux for four hours and then concentrated to an oil. The oil was dissolved in hot water. A precipitate formed and was isolated by filtration. The filtrate was washed five times with dichloromethane and then adjusted to pH 14 with 50% (w/w) aqueous sodium hydroxide, resulting in a brown precipitate. The mixture was extracted with several portions of dichloromethane that were combined, washed with water and brine, dried over magnesium sulfate, filtered, and concentrated. The resulting white solid was triturated with diethyl ether and dried to yield 2-(ethoxymethyl)-6,7-dimethyl-1-[(3-pyridin-3-ylisoxazol-5-yl)methyl]-1H-imidazo[4,5-c]pyridin-4-amine as a white powder, mp 189.0-191.0° C.

$^1$H NMR (300 MHz, DMSO-d$_6$) δ 9.04 (d, J=1.5 Hz, 1H), 8.66 (dd, J=3.2, 1.6 Hz, 1H), 8.23 (dt, J=8.0, 1.8 Hz, 1H), 7.48-7.52 (m, 1H), 6.92 (s, 1H), 5.91 (s, 2H), 5.86 (s, 2H), 4.74 (s, 2H), 3.45 (q, J=7.0 Hz, 2H), 2.30 (s, 3H), 2.28 (s, 3H), 0.97 (t, J=7.0 Hz, 3H).

MS (APCI) m/z 379 (M+H)$^+$.

Anal. calcd for C$_{20}$H$_{22}$N$_6$O$_2$: C, 63.48; H, 5.86; N, 22.21. Found: C, 63.20; H, 6.03; N, 21.94.

Example 10

2-Ethoxymethyl-1-[2-(3,5,5-trimethyl-1,2,4-oxadiazol-4(5H)-yl)ethyl]-1H-imidazo[4,5-c]quinolin-4-amine

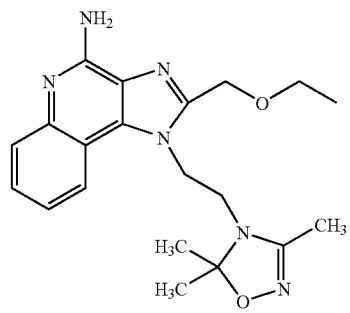

Part A 1,2-Diaminoethane (7.55 mL, 113 mmol) was added to a 0° C. solution of 2,4-dichloro-3-nitroquinoline (28.9 g, 119 mmol) and triethylamine (24.9 mL, 179 mmol) in dichloromethane (600 mL). The solution was allowed to warm slowly to room temperature and stir for 20 hours. The solvent was removed under reduced pressure and 5% aqueous $Na_2CO_3$ (300 mL) was added. The resulting slurry was stirred vigorously at 0° C. for four hours. A yellow solid was isolated by vacuum filtration and dried under vacuum. The solid was purified by suction filter chromatography (silica gel, gradient elution from 98:2 to 93:7 dichloromethane/methanol) to provide the product N-(2-chloro-3-nitroquinolin-4-yl)ethane-1, 2-diamine (16.0 g) that contained a small amount of an impurity.

Part B

Triethylamine (3.12 mL, 22.4 mmol) was added to a slurry of N-(2-chloro-3-nitroquinolin-4-yl)ethane-1,2-diamine (3.00 g, 11.2 mmol) in dichloromethane (80 mL). A solution of di-tert-butyl carbonate (2.95 g, 13.5 mmol) in dichloromethane (20 mL) was added over 5 minutes to the slurry. The solution was stirred at room temperature for three hours and then was partitioned between dichloromethane and saturated aqueous sodium bicarbonate. The aqueous layer was extracted with dichloromethane. The organic layers were combined and washed with brine, dried over magnesium sulfate, filtered, and concentrated to an orange solid. The crude product was purified by flash chromatography (silica gel, 3:1 hexanes/ethyl acetate as the eluent) to afford tert-butyl 2-[(2-chloro-3-nitroquinolin-4-yl)amino]ethylcarbamate (3.70 g) as a bright yellow solid.

Part C

A solution of $Na_2S_2O_4$ (10.3 g, 50.4 mmol) in water (40 mL) was added to a solution of tert-butyl 2-[(2-chloro-3-nitroquinolin-4-yl)amino]ethylcarbamate (3.70 g, 10.1 mmol). A white solid precipitated immediately and after 30 min the precipitate was removed by filtration. The filtrate was concentrated under reduced pressure, was diluted with saturated aqueous sodium bicarbonate, and was extracted with dichloromethane three times. The combined organic layers were washed with brine, dried over magnesium sulfate, filtered, and concentrated to a pale yellow oil. Purification by flash chromatography (silica gel, gradient elution with 2:1 to 1:1 hexanes/ethyl acetate) afforded tert-butyl 2-[(3-amino-2-chloroquinolin-4-yl)amino]ethylcarbamate (2.14 g) as a colorless oil.

Part D

A solution of ethoxyacetyl chloride (857 mg, 6.99 mmol) in acetonitrile (5 mL) was added to solution of tert-butyl 2-[(3-amino-2-chloroquinolin-4-yl)amino]ethylcarbamate (2.14 g, 6.35 mmol) in acetonitrile (20 mL). After five minutes, the solution was cooled in an ice bath and a white precipitate began to form. After one hour, the precipitate was isolated by filtration and dried under vacuum to afford the hydrochloride salt of tert-butyl 2-({2-chloro-3-[(ethoxyacetyl)amino]quinolin-4-yl}amino)ethylcarbamate (2.50 g).

Part E

To a solution of the hydrochloride salt of tert-butyl 2-({2-chloro-3-[(ethoxyacetyl)amino]quinolin-4-yl}amino)ethylcarbamate (2.50 g, 5.44 mmol) in 9:1 ethanol/water (50 mL) was added a solution of potassium carbonate (1.12 g, 8.16 mmol) in water (5 mL). The solution was heated to 50° C. for five hours. The solution was concentrated under reduced pressure and the residue was partitioned between saturated aqueous sodium bicarbonate and dichloromethane. The aqueous layer was extracted with two additional portions of dichloromethane. The combined organic layers were washed with brine, dried over magnesium sulfate, filtered, and concentrated to a pale yellow solid that was purified by flash chromatography (silica gel, gradient elution from 1:1 to 4:1 ethyl acetate/hexane) to afford the tert-butyl 2-(4-chloro-2-ethoxymethyl-1H-imidazo[4,5-c]quinolin-1-yl]ethylcarbamate as a white solid (1.55 g).

Part F

A solution of tert-butyl 2-(4-chloro-2-ethoxymethyl-1H-imidazo[4,5-c]quinolin-1-yl]ethylcarbamate (1.55 g, 3.83 mmol) in a solution of 4 M hydrogen chloride in dioxane (15 mL) was stirred at room temperature for two hours. An aqueous solution of 2 M sodium hydroxide was added to adjust the reaction to pH 13. The solution was extracted with several portions of dichloromethane. The combined organic layers were washed with brine, dried over magnesium sulfate, filtered, and concentrated. The crude product was purified by flash chromatography (silica gel, gradient elution from 97:3 to 97:5 dichloromethane/methanol) to afford 2-(4-chloro-2-ethoxymethyl-1H-imidazo[4,5-c]quinolin-1-yl)ethylamine (760 mg) as a white solid.

Part G

A mixture of 2-(4-chloro-2-ethoxymethyl-1H-imidazo[4, 5-c]quinolin-1-yl)ethylamine (760 mg, 2.49 mmol) and magnesium sulfate in 9:1 dichloromethane/acetone was stirred at room temperature for four hours. The mixture was filtered and the filtrate was concentrated. The residue was dissolved in dichloromethane (20 mL) and added to N-hydroxyethanimidoyl chloride (3.11 mmol). The N-hydroxyethanimidoyl chloride was prepared as follows: to a 0° C. solution of acetaldehyde oxime (184 mg, 3.11 mmol) in DMF (10 mL) was added N-chlorosuccinimide (415 mg, 3.11 mmol) over a period of five minutes. After 15 minutes, the solution was warmed to 50° C. for one hour. The solution was partitioned between water and ethyl acetate. The aqueous layer was extracted with two additional portions of ethyl acetate. The combined organic layers were washed with water and brine, dried over magnesium sulfate, filtered, and concentrated to provide N-hydroxyethanimidoyl chloride as a pale yellow oil. The dichloromethane solution from above was cooled in an ice bath and triethyamine (0.52 mL, 3.73 mmol) was added, resulting in the formation of a white precipitate. The mixture was allowed to warm slowly to room temperature and stir overnight. The solution was washed with saturated aqueous sodium bicarbonate and brine, dried over magnesium sulfate, filtered, and concentrated. The crude product was purified by flash chromatography (silica gel, gradient elution from 98:2 to 96:4 dichloromethane/methanol) to yield 4-chloro-2-ethoxymethyl-1-[2-(3,5,5-trimethyl-1,2,4-oxadiazol-4(5H)-yl)ethyl]-1H-imidazo[4,5-c]quinoline (680 mg) as a white solid.

Part H

A slurry of 4-chloro-2-ethoxymethyl-1-[2-(3,5,5-trimethyl-1,2,4-oxadiazol-4(5H)-yl)ethyl]-1H-imidazo[4,5-c]quinoline (670 mg, 1.67 mmol) in a solution of 7 M ammonia in methanol (20 mL) was sealed in a pressure vessel and heated to 150° C. After 15 hours, the volatiles were removed under reduced pressure and the residue was partitioned between saturated aqueous sodium bicarbonate and dichloromethane. The aqueous layer was extracted with two additional portions of dichloromethane. The combined organic layers were washed with brine, dried over magnesium sulfate, filtered, and concentrated. The crude product was purified by flash chromatography (silica gel, gradient elution from 97:3 to 95:5 dichloromethane/methanol) to afford 2-ethoxymethyl-1-[2-(3,5,5-trimethyl-1,2,4-oxadiazol-4(5H)-yl) ethyl]-1H-imidazo[4,5-c]quinolin-4-amine (350 mg) as a white solid that was recrystallized from acetonitrile to give white needles, mp 204-205° C.

$^1$H NMR (300 MHz, CDCl$_3$) δ 7.96 (dd, J=8.2, 1.0 Hz, 1H), 7.86 (dd, J=8.4, 1.0 Hz, 1H), 7.57 (ddd, J=8.4, 7.1, 1.3 Hz, 1H), 7.35 (ddd, J=8.3, 7.1, 1.3 Hz, 1H), 5.46 (br s, 2H), 4.83 (s, 2H), 4.80 (t, J=6.9 Hz, 2H), 3.66-3.57 (m, 4H), 1.85 (s, 3H), 1.39 (s, 6H), 1.25 (t, J=7.0 Hz, 3H).

MS (APCI) m/z 383 (M+H$^+$).

Anal. calcd for C$_{20}$H$_{26}$N$_6$O$_2$: C, 62.81; H, 6.85; N, 21.97. Found: C, 62.83; H, 7.20; N, 22.13.

Example 11

1-{[3-(4-Fluorophenyl)isoxazol-5-yl]methyl}-1H-imidazo[4,5-c][1,5]naphthyridin-4-amine

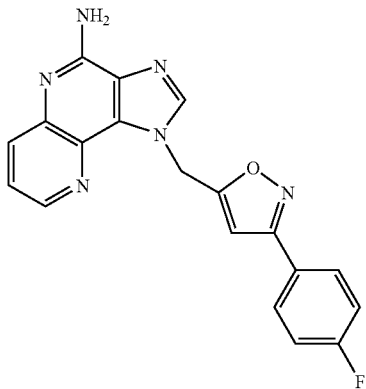

Part A

Propargylamine (54 mL, 0.98 mol) was added over a period of one hour to a suspension of 4-chloro-3-nitro[1,5]naphthyridine (186.4 g, 0.889 mol) and triethylamine (186 mL, 1.33 mol) in THF (1 L) while maintaining the reaction temperature at 25° C. The reaction was stirred for 45 minutes, and then deionized water (21 mL per gram of expected product) was added. The resulting suspension was stirred for about one hour and filtered to isolate a solid. The solid was washed with water until the filtrate was pH neutral and then dried under vacuum at 65° C. to provide 181.2 g of 3-nitro-N-prop-2-ynyl[1,5]naphthyridin-4-amine as a brown solid.

Part B

Aqueous sodium hydroxide (70 mL of 50% w/w) was added to a solution of 4-fluorobenzaldehyde (140.5 g, 1.132 mol) and hydroxylamine hydrochloride (86.5 g, 1.25 mol) in ethanol (1 L) and water (2 L), and the reaction was stirred at room temperature for one hour and then adjusted to pH 14 with the addition of 50% w/w aqueous sodium hydroxide. The mixture was extracted with several portions of dichloromethane and then several portions of chloroform. The combined extracts were concentrated under reduced pressure approximately one liter, filtered through a layer of CELITE filter agent and sodium sulfate, and concentrated again under reduced pressure to yield 127 g of 4-fluorobenzaldehyde oxime as a white solid.

Part C

N-Chlorosuccinimide (85.5 g, 438 mmol) was added to a solution of 4-fluorobenzaldehyde oxime (61.0 g, 438 mmol) in DMF (100 mL) at room temperature; an exotherm occurred. After the addition, the solution was heated at 40° C. for 30 minutes under nitrogen. The solution was poured onto ice and extracted with chloroform. The combined extracts were washed with brine, dried over magnesium sulfate, filtered, and concentrated under reduced pressure, and further dried under high vacuum for 16 hours to provide 52.23 g of 4-fluoro-N-hydroxybenzenecarboximidoyl chloride as an amber oil.

Part D

Under a nitrogen atmosphere, 4-fluoro-N-hydroxybenzenecarboximidoyl chloride (7.6 g, 44 mmol) was added to a heated solution (40° C.) of 3-nitro-N-prop-2-ynyl[1,5]naphthyridin-4-amine (5.0 g, 22 mmol) and anhydrous triethylamine (6.7 mL, 48 mmol) in anhydrous dichloromethane (150 mL). The reaction was heated at 40° C. for 1.7 hours and then concentrated under reduced pressure. The residue was triturated with water; the resulting solid was isolated by filtration, washed sequentially with toluene and a small amount of diethyl ether, and then dissolved in dichloromethane. The solution was concentrated under reduced pressure and dried under high vacuum to provide 6.00 g of N-{[3-(4-fluorophenyl)isoxazol-5-yl]methyl}-3-nitro[1,5]naphthyridin-4-amine as a brownish-yellow solid.

Part E

A Parr vessel was charged with 5% platinum on carbon (0.12 g), purged with nitrogen, and then charged sequentially with toluene (2 mL), N-{[3-(4-fluorophenyl)isoxazol-5-yl]methyl}-3-nitro[1,5]naphthyridin-4-amine (6.00 g, 16.4 mmol), toluene (73 mL), and isopropanol (5 mL). The vessel was purged with hydrogen three times and then placed under hydrogen pressure (50 psi, 3.4×10$^5$ Pa) for 16 hours. An analysis by high-performance liquid chromatography (HPLC) indicated the presence of starting material. The catalyst was removed by filtration and washed with hot dichloromethane and methanol. The filtrate was concentrated under reduced pressure, and the residue was dissolved in hot methanol (100 mL) and added to a Parr vessel. Catalytic 5% platinum on carbon (0.12 g) was added, and the reaction was placed under hydrogen pressure (50 psi, 3.4×10$^5$ Pa) for four hours. The catalyst was removed by filtration, and the filtrate was concentrated under reduced pressure to provide N$^4$-{[3-(4-fluorophenyl)isoxazol-5-yl]methyl}[1,5]naphthyridine-3,4-diamine.

Part F

Triethyl orthoformate (4.1 mL, 25 mmol) was added to a solution of the material from Part E and pyridine hydrochloride (0.04 g, 0.3 mmol) in toluene (1 L), and the reaction was heated at 110° C. in a nitrogen atmosphere for 1.5 hours. A Dean-Stark trap was used to collect the volatiles. The reaction mixture was then concentrated under reduced pressure, and the residue was partitioned between dichloromethane and 1 N aqueous sodium hydroxide. The aqueous fraction was extracted several times with dichloromethane, and the combined organic fractions were washed with water and brine, dried over magnesium sulfate, filtered, and concentrated under reduced pressure. The resulting solid was triturated with a mixture of diethyl ether and hexane, isolated by filtration, and dried under vacuum to provide 2.76 g of 1-{[3-(4-fluorophenyl)isoxazol-5-yl]methyl}-1H-imidazo[4,5-c][1,5]naphthyridine as a green powder.

Part G

3-Chloroperoxybenzoic acid (mCPBA) (2.4 g of 75% pure material) was added to a suspension of 1-{[3-(4-fluorophenyl)isoxazol-5-yl]methyl}-1H-imidazo[4,5-c][1,5]naphthyridine (2.76 g, 7.99 mmol) in dichloromethane (100 mL). The reaction was stirred at room temperature for 30 minutes; an analysis by TLC then indicated the presence of starting material. Additional mCPBA (0.065 g of 75%) was added, and the reaction was stirred for another 30 minutes and found to be complete by TLC analysis. Concentrated ammonium hydroxide (50 mL) and p-toluenesulfonyl chloride (1.68 g, 8.79 mmol) were sequentially added. The mixture was stirred for 30 minutes. The volatiles were removed under reduced pressure, and 1 N aqueous sodium hydroxide and water were added to the resulting mixture, which was filtered to isolate a solid. The solid was washed with diethyl ether. Additional solid precipitated from the aqueous filtrate, and was isolated by filtration and combined with the first solid to provide 2.48 g of 1-{[3-(4-fluorophenyl)isoxazol-5-yl]methyl}-5-oxido-1H-imidazo[4,5-c][1,5]naphthyridine, which was dissolved in a mixture of methanol (80 mL) and dichloromethane (80 mL). The resulting mixture was heated to 50° C., and concentrated ammonium hydroxide (20 mL) and benzenesulfonyl chloride (1.2 mL, 7.6 mmol) were added. The reaction was heated under a nitrogen atmosphere for one hour, and additional benzenesulfonyl chloride (0.5 mL) was added. The solvents were removed under reduced pressure, and the residue was purified by column chromatography on silica gel (eluting with 2% to 10% CMA in chloroform) followed by recrystallization from acetonitrile to provide 0.612 g of 1-{[3-(4-fluorophenyl)isoxazol-5-yl]methyl}-1H-imidazo[4,5-c][1,5]naphthyridin-4-amine as a white solid, mp 265.0-266.0° C.

MS (ESI) m/z 361 (M+H)+.

Anal. calcd for $C_{19}H_{13}FN_6O$: C, 63.33; H, 3.64; N, 23.32. Found: C, 63.20; H, 3.68; N, 23.43.

Example 12

2-(Ethoxymethyl)-1-{[3-(4-fluorophenyl)isoxazol-5-yl]methyl}-1H-imidazo[4,5-c][1,5]naphthyridin-4-amine

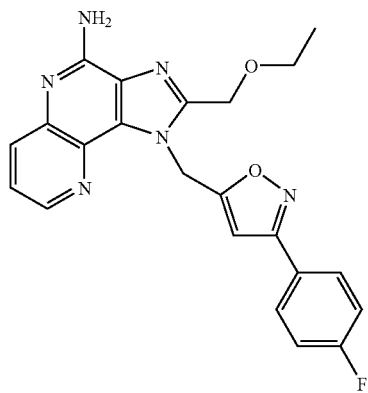

Part A

Under a nitrogen atmosphere, 4-fluoro-N-hydroxybenzenecarboximidoyl chloride (44.6 g, 257 mmol) was added to a mixture of 3-nitro-N-prop-2-ynyl[1,5]naphthyridin-4-amine (29.34 g, 129 mmol) and anhydrous triethylamine (39.5 mL, 283 mmol) in anhydrous dichloromethane (1 L). The reaction was stirred at 40° C. for 18 hours and then concentrated under reduced pressure. The residue was triturated with water; the resulting solid was isolated by filtration, washed sequentially with isopropanol and a small amount of diethyl ether, and then dried under vacuum to provide 15.02 g of N-{[3-(4-fluorophenyl)isoxazol-5-yl]methyl}-3-nitro[1,5]naphthyridin-4-amine as a brownish-green solid.

Part B

A solution of N-{[3-(4-fluorophenyl)isoxazol-5-yl]methyl}-3-nitro[1,5]naphthyridin-4-amine (15.02 g, 41.11 mmol) in hot methanol (4 L) was filtered to remove a solid and then added to a Parr vessel charged with 5% platinum on carbon (1.5 g) that had been purged with nitrogen and wet with methanol (50 mL). The vessel was purged with hydrogen three times and then placed under hydrogen pressure (25 psi, $1.7×10^5$ Pa) for 12 hours. The catalyst was removed by filtration and washed with a mixture of dichloromethane and methanol, and the filtrate was concentrated under reduced pressure to provide 8.3 g of $N^4$-{[3-(4-fluorophenyl)isoxazol-5-yl]methyl}[1,5]naphthyridine-3,4-diamine containing an impurity.

Part C

Under a nitrogen atmosphere, ethoxyacetyl chloride (1.6 g, 13 mmol) was added over a period of ten minutes to a cooled (6° C.) solution of $N^4$-{[3-(4-fluorophenyl)isoxazol-5-yl]methyl}[1,5]naphthyridine-3,4-diamine (4.1 g, 12 mmol) and anhydrous triethylamine (2.6 mL, 18 mmol) in anhydrous dichloromethane (150 mL). After the reaction was stirred for 30 minutes, an analysis by HPLC indicated the presence of starting material, and additional ethoxyacetyl chloride (1.1 g) was added. The reaction was stirred for an additional 30 minutes and then was diluted with dichloromethane and washed with saturated aqueous potassium carbonate. The aqueous layer was separated and extracted with dichloromethane, and the combined organic fractions were washed with water and brine, dried over sodium sulfate, filtered, and concentrated under reduced pressure to afford 2-ethoxy-N-[4-({[3-(4-fluorophenyl)isoxazol-5-yl]methyl}amino)[1,5]naphthyridin-3-yl]acetamide as a black oil.

Part D

A solution of the material from Part C and pyridine hydrochloride (0.028 g, 0.24 mmol) in toluene (100 mL) was heated at 110° C. under a nitrogen atmosphere for 22.5 hours. The volatiles were removed under reduced pressure, and the residue was dissolved in dichloromethane. The solution was washed sequentially with saturated aqueous potassium carbonate, water, and brine; dried over sodium sulfate; filtered; and concentrated under reduced pressure. The residue was purified by column chromatography on silica gel (eluting with ethyl acetate) and then triturated with a mixture of diethyl ether and hexane and isolated by filtration to provide 1.74 g of 2-(ethoxymethyl)-1-{[3-(4-fluorophenyl)isoxazol-5-yl]methyl}-1H-imidazo[4,5-c][1,5]naphthyridine.

Part E mCPBA (1.7 g of 75% pure material) was added to a solution of 2-(ethoxymethyl)-1-{[3-(4-fluorophenyl)isoxazol-5-yl]methyl}-1H-imidazo[4,5-c][1,5]naphthyridine (1.74 g, 4.31 mmol) in dichloromethane (50 mL). The reaction was stirred at room temperature for 30 minutes; an analysis by TLC then indicated the presence of starting material. Additional mCPBA (0.25 g of 75%) was added, and the reaction was stirred for another 30 minutes and found to be complete. The solvent was removed under reduced pressure, and the residue was triturated with diethyl ether and isolated by filtration to provide 1.64 g of 2-(ethoxymethyl)-1-{[3-(4-fluorophenyl)isoxazol-5-yl]methyl}-5-oxido-1H-imidazo[4,5-c][1,5]naphthyridine as a pale yellow solid.

Part F

Under a nitrogen atmosphere, a solution of 2-(ethoxymethyl)-1-{[3-(4-fluorophenyl)isoxazol-5-yl]methyl}-5-oxido-1H-imidazo[4,5-c][1,5]naphthyridine (1.64 g, 3.90 mmol) in anhydrous dichloromethane (50 mL) was cooled to 6° C., and a solution of trichloroacetyl isocyanate (0.51 mL, 4.29 mmol) in dichloromethane (5 mL) was added dropwise. The solution was stirred for 30 minutes, and then the solvent was removed under reduced pressure. The residue was treated with sodium methoxide in methanol (10 mL of a 25% w/w solution) and methanol (40 mL). The resulting mixture was stirred for 18 hours at room temperature. A precipitate was present and was isolated by filtration, washed with methanol and diethyl ether, and dried under high vacuum at 80° C. for 18 hours to provide 0.999 g of 2-(ethoxymethyl)-1-{[3-(4-fluorophenyl)isoxazol-5-yl]methyl}-1H-imidazo[4,5-c][1,5]naphthyridin-4-amine as a white solid, mp 190.0-191.0° C.

MS (ESI) m/z 419 (M+H)+.

Anal. calcd for $C_{22}H_{19}FN_6O_2 \cdot 0.3H_2O$: C, 62.35; H, 4.66; N, 19.83. Found: C, 62.05; H, 4.28; N, 19.71.

Example 13

1-{[3-(4-Fluorophenyl)isoxazol-5-yl]methyl}-2-methyl-1H-imidazo[4,5-c][1,5]naphthyridin-4-amine

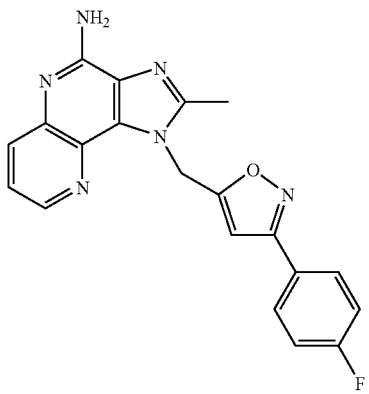

Part A

Triethyl orthoacetate (2.8 mL, 15.2 mmol) was added to a solution of $N^4$-{[3-(4-fluorophenyl)isoxazol-5-yl]methyl}[1,5]naphthyridine-3,4-diamine (prepared in Part B of Example 12, 3.4 g, 10.1 mmol) and pyridine hydrochloride (0.023 g, 0.20 mmol) in toluene (100 mL), and the reaction was heated at 110° C. under a nitrogen atmosphere for 15.5 hours. The reaction mixture was then concentrated under reduced pressure, and the residue was dissolved in dichloromethane. The work-up and purification procedures described in Part D of Example 12 were followed with the modification that the silica column was eluted with 5% methanol in ethyl acetate. 1-{[3-(4-Fluorophenyl)isoxazol-5-yl]methyl}-2-methyl-1H-imidazo[4,5-c][1,5]naphthyridine (1.15 g) was obtained as a light gray solid.

Part B

The method described in Part E of Example 12 was used to treat 1-{[3-(4-fluorophenyl)isoxazol-5-yl]methyl}-2-methyl-1H-imidazo[4,5-c][1,5]naphthyridine (1.15 g, 3.20 mmol) with mCPBA (0.94 g of 75% pure material followed by 0.25 g) to provide 1-{[3-(4-fluorophenyl)isoxazol-5-yl]methyl}-2-methyl-5-oxido-1H-imidazo[4,5-c][1,5]naphthyridine as a dark yellow solid.

Part C

The method described in Part F of Example 12 was followed using the material from Part B as the starting material with the modification that the reaction with sodium methoxide was stirred for 20 hours and found to be incomplete as evidenced by HPLC analysis. Additional sodium methoxide (15 mL of a 25% w/w solution in methanol) was added, and the reaction was stirred for an additional 16 hours. After the solid product was filtered and washed, it was recrystallized from acetonitrile and dried under high vacuum at 80° C. to provide 0.253 g of 1-{[3-(4-fluorophenyl)isoxazol-5-yl]methyl}-2-methyl-1H-imidazo[4,5-c][1,5]naphthyridin-4-amine as a white solid, mp 239.0-240.0° C.

MS (ESI) m/z 375 (M+H)+.

Anal. calcd for $C_{20}H_{15}FN_6O$: C, 64.17; H, 4.04; N, 22.45. Found: C, 64.01; H, 3.95; N, 22.50.

Example 14

1-{[3-(4-Fluorophenyl)isoxazol-5-yl]methyl}-2-propyl-1H-imidazo[4,5-c][1,5]naphthyridin-4-amine

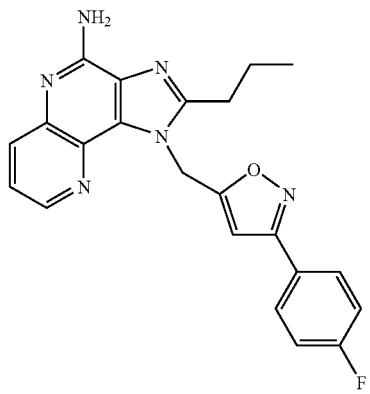

Part A

The methods described in Part A of Example 13 were used to treat $N^4$-{[3-(4-fluorophenyl)isoxazol-5-yl]methyl}[1,5]naphthyridine-3,4-diamine (2.6 g, 7.8 mmol) with trimethyl orthobutyrate (1.9 mL, 12 mmol) in the presence of pyridine hydrochloride (0.018 g, 0.16 mmol) and isolated and purify the final product with the modification that the silica column was eluting with 60-90% ethyl acetate in dichloromethane. 1-{[3-(4-Fluorophenyl)isoxazol-5-yl]methyl}-2-propyl-1H-imidazo[4,5-c][1,5]naphthyridine (1.08 g) was obtained as a white solid.

Part B

The method described in Part E of Example 12 was used to treat 1-{[3-(4-fluorophenyl)isoxazol-5-yl]methyl}-2-propyl-1H-imidazo[4,5-c][1,5]naphthyridine (1.08 g, 2.79 mmol) with mCPBA (1.1 g of 75% pure material followed by 0.35 g) with the modification that the trituration of the crude product was carried out with diethyl ether. 1-{[3-(4-Fluorophenyl)isoxazol-5-yl]methyl}-5-oxido-2-propyl-1H-imidazo[4,5-c][1,5]naphthyridine was obtained as a white solid.

Part C

The method described in Part F of Example 12 was followed using the material from Part B as the starting material with the modification that 40 mL of 25% w/w sodium methoxide in methanol were used in the second step with no additional methanol; the reaction was complete in 2.7 hours. After the solid product was filtered and washed, it was recrystallized from toluene and dried to provide 0.439 g of 1-{[3-(4-fluorophenyl)isoxazol-5-yl]methyl}-2-propyl-1H-imidazo[4,5-c][1,5]naphthyridin-4-amine as a white solid, mp 238.0-239.0° C.

MS (ESI) m/z 403 (M+H)+.

Anal. calcd for $C_{22}H_{19}FN_6O$: C, 65.66; H, 4.76; N, 20.88. Found: C, 65.82; H, 4.74; N, 20.79.

Example 15

(4-Amino-1-{[3-(4-fluorophenyl)isoxazol-5-yl]methyl}-1H-imidazo[4,5-c][1,5]naphthyridin-2-yl)methanol

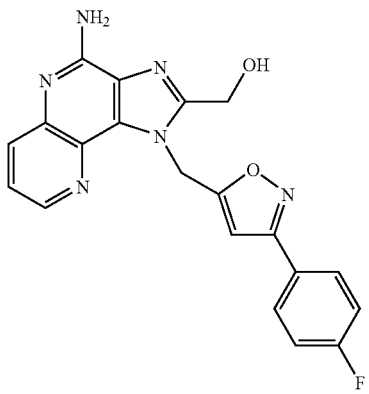

Under a nitrogen atmosphere, a solution of 2-(ethoxymethyl)-1-{[3-(4-fluorophenyl)isoxazol-5-yl]methyl}-1H-imidazo[4,5-c][1,5]naphthyridin-4-amine (0.40 g, 0.96 mmol) in dichloromethane (25 mL) was cooled on an ice bath, and boron tribromide (2.4 mL of a 1 M solution in dichloromethane) was added. The reaction was stirred for 17 hours, and an analysis by HPLC indicated the presence of starting material. Additional boron tribromide (1 mL) was added after 17 hours and then again after 32 hours of reaction time. After 32 hours of reaction time, methanol was added, and the solvents were removed under reduced pressure. The residue was triturated with water, isolated by filtration, washed with diethyl ether, recrystallized from methanol, and dried under high vacuum at 100° C. to provide 0.14 g of (4-amino-1-{[3-(4-fluorophenyl)isoxazol-5-yl]methyl}-1H-imidazo[4,5-c][1,5]naphthyridin-2-yl)methanol as a white solid, mp 247.0-248.0° C.

MS (ESI) m/z 391 (M+H)+.

Anal. calcd for $C_{20}H_{15}FN_6O_2$: C, 61.54; H, 3.87; N, 21.53. Found: C, 61.26; H, 3.90; N, 21.60.

Example 16

2-(Ethoxymethyl)-1-[2-(3-methyl-1-oxa-2,4-diazaspiro[4,4]non-2-en-4-yl)ethyl]-1H-imidazo[4,5-c]quinolin-4-amine

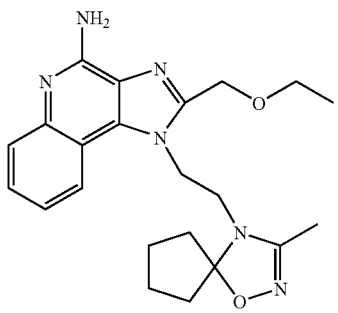

Part A

A mixture of 2-(4-chloro-2-ethoxymethyl-1H-imidazo[4,5-c]quinolin-1-yl)ethylamine (1.00 g, 3.28 mmol), cyclopentanone (0.32 mL, 3.6 mmol), and magnesium sulfate in dichloromethane was stirred at room temperature overnight. The mixture was filtered and the filtrate was concentrated under reduced pressure. The residue was dissolved in dichloromethane (20 mL) along with N-hydroxyethanimidoyl chloride, which was prepared from acetaldehyde oxime (242 mg, 4.10 mmol) and N-chlorosuccinimide (537 mg, 4.10 mmol) according to the method described in Part G of Example 10. The resulting solution was cooled in an ice bath and triethylamine (0.69 mL, 4.9 mmol) was added. The mixture was allowed to warm slowly to room temperature and stirred overnight. The work-up and purification procedures described in Part G of Example 10 were followed to provide 770 mg of 4-chloro-2-(ethoxymethyl)-1-[2-(3-methyl-1-oxa-2,4-diazaspiro[4,4]non-2-en-4-yl)ethyl]-1H-imidazo[4,5-c]quinoline as a clear, colorless oil.

Part B

The methods described in Part H of Example 10 were used to treat 4-chloro-2-(ethoxymethyl)-1-[2-(3-methyl-1-oxa-2,4-diazaspiro[4,4]non-2-en-4-yl)ethyl]-1H-imidazo[4,5-c]quinoline (770 mg, 1.80 mmol) with a solution of 7 M ammonia in methanol (20 mL) and isolate and purify the final product to provide 700 mg of 2-(ethoxymethyl)-1-[2-(3-methyl-1-oxa-2,4-diazaspiro[4,4]non-2-en-4-yl)ethyl]-1H-imidazo[4,5-c]quinolin-4-amine as white needles, mp 211-213° C.

MS (APCI) m/z 409 (M+H+).

Anal. calcd for $C_{22}H_{28}N_6O_2$: C, 64.69; H, 6.91; N, 20.57. Found: C, 64.47; H, 7.08; N, 20.83.

Example 17

1-{[3-(4-Fluorophenyl)isoxazol-5-yl]methyl}-6,7,8,9-tetrahydro-1H-imidazo[4,5-c][1,5]naphthyridin-4-amine

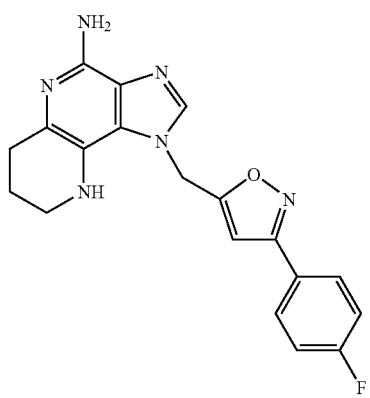

1-{[3-(4-Fluorophenyl)isoxazol-5-yl]methyl}-1H-imidazo[4,5-c][1,5]naphthyridin-4-amine (Example 11, 0.300 g, 0.833 mmol) was combined with platinum (IV) oxide (0.03 g) and trifluoroacetic acid (5 mL), and the mixture was placed under hydrogen pressure (45 psi, $3.1 \times 10^5$ Pa) for 24 hours. An analysis by liquid chromatography/mass spectrometry indicated the presence of starting material. The catalyst was removed by filtration, and the trifluoroacetic acid was removed under reduced pressure. The residue was combined with trifluoroacetic acid (5 mL) and platinum (IV) oxide (0.10 g), and the reaction was again placed under hydrogen pressure (45 psi, 3.1×10$^5$ Pa) for 24 hours. The catalyst was removed by filtration, and the trifluoroacetic acid was removed under reduced pressure. The resulting oil was dissolved in 6 N hydrogen chloride in ethanol and stirred for 30 minutes. The solvent was removed under reduced pressure, and the residue was dissolved in water. The solution was adjusted to pH 14 with the addition of a few drops of 50% w/w sodium hydroxide, and the resulting mixture was stirred for 30 minutes. A precipitate was present and was isolated by filtration, purified by column chromatography on silica gel (5% to 10% CMA in chloroform), triturated with diethyl ether, filtered, and dried to provide 0.0382 g of 1-{[3-(4-fluorophenyl)isoxazol-5-yl]methyl}-6,7,8,9-tetrahydro-1H-imidazo[4,5-c][1,5]naphthyridin-4-amine as a white powder, mp 227.0-228.0° C.

MS (ESI) m/z 365 (M+H)+.

Anal. calcd for $C_{19}H_{17}FN_6O$: C, 62.63; H, 4.70; N, 23.06. Found: C, 62.38; H, 4.62; N, 23.38.

Example 18

1-{[3-(4-Fluorophenyl)isoxazol-5-yl]methyl}-6,7-dimethyl-1H-imidazo[4,5-c]pyridin-4-amine

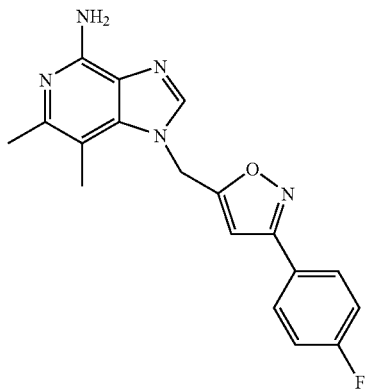

Part A

Under a nitrogen atmosphere, a solution of 2,4-dichloro-5,6-dimethyl-3-nitropyridine (137.9 g, 0.624 mol) in anhydrous DMF (1.4 L) was cooled to 0° C., and anhydrous triethylamine (109 mL, 0.780 mol) was added. Propargyl amine hydrochloride (4.72 g, 51.6 mmol) and propargyl amine (38.4 g, 0.697 mol) were sequentially added dropwise, and the reaction was allowed to warm to room temperature and then heated at 40° C. for 22 hours. The volatiles were removed under reduced pressure, and water (1.5 L) and solid sodium carbonate (75 g) were added to the resulting oil. The mixture was then extracted with dichloromethane, and the combined extracts were washed sequentially with water and brine, dried over sodium sulfate, filtered, and concentrated under reduced pressure. The crude product was purified by column chromatography on silica gel (eluting sequentially with 60:40 dichloromethane/hexane and dichloromethane) to provide 51.54 g of 2-chloro-5,6-dimethyl-3-nitro-N-prop-2-ynylpyridin-4-amine as a brown solid.

Part B

Under a nitrogen atmosphere, 4-fluoro-N-hydroxybenzenecarboximidoyl chloride (52.0 g, 225 mmol), prepared as described in Parts A through C of Example 11, was added to a solution of 2-chloro-5,6-dimethyl-3-nitro-N-prop-2-ynylpyridin-4-amine (26.92 g, 112.3 mmol) in anhydrous dichloromethane (1 L) at room temperature. Triethylamine (25 g, 250 mmol) was added; a precipitate formed. The resulting mixture was heated at 40° C. under nitrogen for 16 hours, diluted with dichloromethane, washed sequentially with aqueous potassium carbonate, water, and brine; dried over sodium sulfate; filtered; and concentrated under reduced pressure to a suspension. The suspension was filtered to isolate a yellow solid, which was washed with diethyl ether and dried under vacuum to provide 32.45 g of 2-chloro-N-{[3-(4-fluorophenyl)isoxazol-5-yl]methyl}-5,6-dimethyl-3-nitropyridin-4-amine.

Part C

Under a nitrogen atmosphere, 2-chloro-N-{[3-(4-fluorophenyl)isoxazol-5-yl]methyl}-5,6-dimethyl-3-nitropyridin-4-amine (25.00 g, 66.35 mmol), toluene (250 mL), triethylamine (11.1 mL, 79.6 mmol), and N,N-bis(4-methoxybenzyl)amine (18.8 g, 73.0 mmol) were combined and heated at reflux for three days. The volatiles were removed under reduced pressure, and the residue was partitioned between ethyl acetate and saturated aqueous potassium carbonate. The ethyl acetate layer was separated and concentrated under reduced pressure. The residue was dissolved in dichloromethane, and the resulting solution was washed sequentially with water and brine. The combined aqueous fractions were extracted with ethyl acetate. The combined organic fractions were dried over sodium sulfate, filtered, and concentrated under reduced pressure. The crude solid was triturated with ethanol, isolated by filtration, and washed with diethyl ether to provide 37.29 g of $N^4$-{[3-(4-fluorophenyl)isoxazol-5-yl]methyl}-$N^2$,$N^2$-bis(4-methoxybenzyl)-5,6-dimethyl-3-nitropyridine-2,4-diamine as an orange solid.

Part D

Under a nitrogen atmosphere, toluene (2 L) was added to a Parr vessel containing 5% platinum on carbon (3.6 g). $N^4$-{[3-(4-Fluorophenyl)isoxazol-5-yl]methyl}-$N^2$,$N^2$-bis(4-methoxybenzyl)-5,6-dimethyl-3-nitropyridine-2,4-diamine (36.85 g, 61.66 mmol) was added followed by ethanol (300 mL). The vessel was sealed, purged with hydrogen, and placed under hydrogen pressure (30 psi, 2.1×10$^5$ Pa) for 18 hours at room temperature. The catalyst was removed by filtration, and the filtrate was concentrated under reduced pressure to provide 39.25 g of $N^4$-{[3-(4-fluorophenyl)isoxazol-5-yl]methyl}-$N^2$,$N^2$-bis(4-methoxybenzyl)-5,6-dimethylpyridine-2,3,4-triamine as a yellow oil.

Part E $N^4$-{[3-(4-Fluorophenyl)isoxazol-5-yl]methyl}-$N^2$,$N^2$-bis(4-methoxybenzyl)-5,6-dimethylpyridine-2,3,4-triamine (6.00 g, 10.6 mmol), triethyl orthoformate (2.6 mL, 16 mmol), concentrated hydrochloride acid (0.2 mL), and toluene (30 mL) were combined at heated at reflux for 24 hours. An analysis by HPLC indicated the reaction was incomplete. Therefore, pyridine hydrochloride (0.25 g) was added, and the reaction vessel was fitted with a Dean-Stark trap. The reaction was heated at reflux for an additional 1.8 days, and additional triethyl orthoformate (1 mL) was added and heating was resumed. After the reaction was heated for a total of three days, it was allowed to cool to room temperature, and concentrated under reduced pressure. The residue was dissolved in dichloromethane, and the resulting solution was washed sequentially with aqueous potassium carbonate, water, and brine; dried over magnesium sulfate; and filtered. The solution was purified by column chromatography on silica gel (eluting with 5% ethyl acetate in dichloromethane) to provide 2.0 g of 1-{[3-(4-fluorophenyl)isoxazol-5-yl]methyl}-N,N-bis(4-methoxybenzyl)-6,7-dimethyl-1H-imidazo[4,5-c]pyridin-4-amine as a pale yellow solid.

Part F

A solution of 1-{[3-(4-fluorophenyl)isoxazol-5-yl]methyl}-N,N-bis(4-methoxybenzyl)-6,7-dimethyl-1H-imidazo[4,5-c]pyridin-4-amine (2.0 g, 3.5 mmol) in trifluoroacetic acid (20 mL) was stirred at room temperature for 16 hours. The trifluoroacetic acid was removed under reduced pressure, and the residue was triturated with aqueous hydrochloric acid (25 mL of 6 N) and ethanol (20 mL) for 30 minutes. The resulting mixture was adjusted to pH 14 with the addition of 50% (w/w) aqueous sodium hydroxide and stirred at 0° C. for 30 minutes. A solid was present and was isolated by filtration and purified by column chromatography on silica gel (eluting with 5% to 10% CMA in chloroform). The resulting solid was dried under high vacuum at 100° C. for 18 hours to provide 0.708 g of 1-{[3-(4-fluorophenyl)isoxazol-5-yl]methyl}-6,7-dimethyl-1H-imidazo[4,5-c]pyridin-4-amine as a white powder, mp 244.0-246.0° C.

MS (ESI) m/z 338 (M+H)+.

Anal. calcd for $C_{18}H_{16}FN_5O$: C, 64.09; H, 4.78; N, 20.76. Found: C, 63.40; H, 4.95; N, 20.76.

Example 19

2-(Ethoxymethyl)-1-{[3-(4-fluorophenyl)isoxazol-5-yl]methyl}-6,7-dimethyl-1H-imidazo[4,5-c]pyridin-4-amine

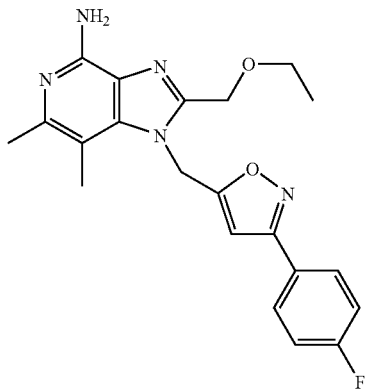

Part A

Under a nitrogen atmosphere, ethoxyacetyl chloride (1.4 g, 11 mmol) was added dropwise to a solution of $N^4$-{[3-(4-fluorophenyl)isoxazol-5-yl]methyl}-$N^2$,$N^2$-bis(4-methoxybenzyl)-5,6-dimethylpyridine-2,3,4-triamine (5.898 g, 10.39 mmol) and triethylamine (2.2 mL, 15 mmol) in dichloromethane (30 mL) at 0° C. After the reaction was stirred for 0.7 hours, an analysis by HPLC indicated the presence of starting material, and additional ethoxyacetyl chloride (0.54 g) was added. The stirring was continued, and after 1.5 hours, the reaction mixture was diluted with dichloromethane and washed sequentially with saturated aqueous potassium carbonate, water, and brine; dried over sodium sulfate, filtered, and concentrated under reduced pressure to provide 6.2 g of N-[2-[bis(4-methoxybenzyl)amino]-4-({[3-(4-fluorophenyl)isoxazol-5-yl]methyl}amino)-5,6-dimethylpyridin-3-yl]-2-ethoxyacetamide as a yellow oil.

Part B

The material from Part A, pyridine hydrochloride (1.1 g, 9.5 mmol), toluene (30 mL) were combined and heated at reflux for three days, allowed to cool to room temperature, and concentrated under reduced pressure. The residue was dissolved in dichloromethane, and the resulting solution was washed sequentially with aqueous potassium carbonate, water, and brine; dried over sodium sulfate; filtered; and concentrated under reduced pressure. The resulting reddish-orange oil (6.94 g) was purified by column chromatography on silica gel (240 g, eluting with 20% ethyl acetate in hexane) to provide 3.55 g of 2-(ethoxymethyl)-1-{[3-(4-fluorophenyl)isoxazol-5-yl]methyl}-N,N-bis(4-methoxybenzyl)-6,7-dimethyl-1H-imidazo[4,5-c]pyridin-4-amine.

Part C

A solution of 2-(ethoxymethyl)-1-{[3-(4-fluorophenyl)isoxazol-5-yl]methyl}-N,N-bis(4-methoxybenzyl)-6,7-dimethyl-1H-imidazo[4,5-c]pyridin-4-amine (3.55 g, 5.58 mmol) in trifluoroacetic acid (30 mL) was stirred at room temperature for three days. The trifluoroacetic acid was removed under reduced pressure, and the residue was triturated with hydrochloric acid (50 mL of a 6 N in ethanol) and water (10 mL) for 30 minutes. The resulting mixture was adjusted to pH 14 with the addition of 50% (w/w) aqueous sodium hydroxide and stirred for 30 minutes. The volatiles were removed under reduced pressure, and the residue was recrystallized from aceotnitrile after a hot filtration. Three crops of crystals were collected to provide 1.35 g of 2-(ethoxymethyl)-1-{[3-(4-fluorophenyl)isoxazol-5-yl]methyl}-6,7-dimethyl-1H-imidazo[4,5-c]pyridin-4-amine. A portion of this material was diluted with dichloromethane. The resulting solution was washed sequentially with aqueous potassium carbonate, water, and brine; purified by column chromatography on silica gel (250 g, eluting with 15% CMA in chloroform); and dried to provide 0.657 g of an analytically pure sample as a white powder, mp 246.0-247.0° C.

MS (ESI) m/z 396 (M+H)+.

Anal. calcd for $C_{21}H_{22}FN_5O_2$: C, 63.79; H, 5.61; N, 17.71. Found: C, 63.59; H, 5.50; N, 17.57.

Example 20

(4-Amino-1-{[3-(4-fluorophenyl)isoxazol-5-yl]methyl}-6,7-dimethyl-1H-imidazo[4,5-c]pyridin-2-yl)methanol

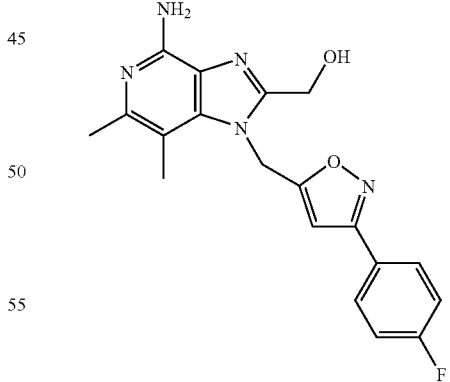

Under a nitrogen atmosphere, a solution of 2-(ethoxymethyl)-1-{[3-(4-fluorophenyl)isoxazol-5-yl]methyl}-6,7-dimethyl-1H-imidazo[4,5-c]pyridin-4-amine (0.8545 g, 2.161 mmol) in dichloromethane (50 mL) was cooled to about 6° C., and boron tribromide (5.4 mL of a 1 M solution in dichloromethane) was added dropwise. The reaction was heated at reflux under nitrogen for two hours and diluted with dichloromethane and methanol. The resulting solution was

Example 21

2-Ethyl-1-{[3-(4-fluorophenyl)isoxazol-5-yl]methyl}-6,7-dimethyl-1H-imidazo[4,5-c]pyridin-4-amine

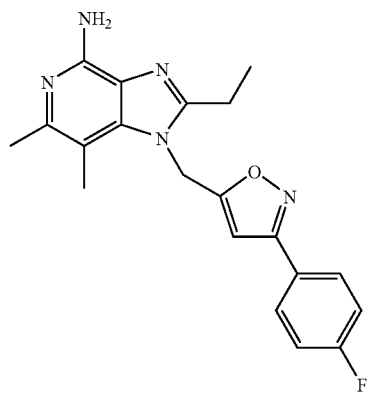

Part A $N^4$-{[3-(4-Fluorophenyl)isoxazol-5-yl]methyl}-$N^2,N^2$-bis(4-methoxybenzyl)-5,6-dimethylpyridine-2,3,4-triamine (6.00 g, 10.6 mmol), triethyl orthopropionate (3.2 mL, 16 mmol), concentrated hydrochloride acid (0.2 mL), and toluene (30 mL) were combined and treated according to the method described in Part E of Example 18 with the modification that no additional triethyl orthopropionate was added. 2-Ethyl-1-{[3-(4-fluorophenyl)isoxazol-5-yl]methyl}-N,N-bis(4-methoxybenzyl)-6,7-dimethyl-1H-imidazo[4,5-c]pyridin-4-amine (2.52 g) was obtained as a yellow solid.

Part B

Under a nitrogen atmosphere, a solution of 2-ethyl-1-{[3-(4-fluorophenyl)isoxazol-5-yl]methyl}-N,N-bis(4-methoxybenzyl)-6,7-dimethyl-1H-imidazo[4,5-c]pyridin-4-amine (2.52 g, 4.16 mmol) in trifluoroacetic acid (25 g) was stirred at room temperature for 20 hours. The trifluoroacetic acid was removed under reduced pressure, and the resulting red oil was stirred with aqueous hydrochloric acid (25 mL of 6 N) and ethanol (10 mL) for 30 minutes. The resulting mixture filtered to remove a solid impurity, cooled to 0° C., adjusted to pH 14 with the addition of 50% (w/w) aqueous sodium hydroxide, and stirred at for 30 minutes. A solid was present and was isolated by filtration and purified by sequential trituration with toluene, trituration with diethyl ether, and recrystallization from acetonitrile to provide 0.6488 g of 2-ethyl-1-{[3-(4-fluorophenyl)isoxazol-5-yl]methyl}-6,7-dimethyl-1H-imidazo[4,5-c]pyridin-4-amine as a white flocculant solid, mp 255.0-256.0° C.

MS (ESI) m/z 366 (M+H)+.

Anal. calcd for $C_{20}H_{20}FN_5O$: C, 65.74; H, 5.52; N, 19.17. Found: C, 65.62; H, 5.43; N, 19.14.

Example 22

1-{[3-(4-Fluorophenyl)isoxazol-5-yl]methyl}-2,6,7-trimethyl-1H-imidazo[4,5-c]pyridin-4-amine

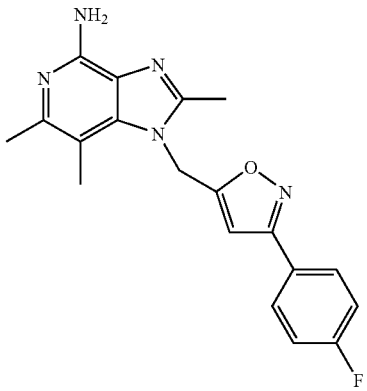

Part A $N^4$-{[3-(4-Fluorophenyl)isoxazol-5-yl]methyl}-$N^2,N^2$-bis(4-methoxybenzyl)-5,6-dimethylpyridine-2,3,4-triamine (6.00 g, 10.6 mmol), triethyl orthoacetate (2.9 mL, 16 mmol), concentrated hydrochloride acid (0.2 mL), and toluene (30 mL) were combined and treated according to the method described in Part E of Example 18 with the modification that no additional triethyl orthoacetate was added. 1-{[3-(4-Fluorophenyl)isoxazol-5-yl]methyl}-N,N-bis(4-methoxybenzyl)-2,6,7-trimethyl-1H-imidazo[4,5-c]pyridin-4-amine (1.48 g) was obtained as a yellow solid.

Part B

Under a nitrogen atmosphere, a solution of 1-{[3-(4-fluorophenyl)isoxazol-5-yl]methyl}-N,N-bis(4-methoxybenzyl)-2,6,7-trimethyl-1H-imidazo[4,5-c]pyridin-4-amine (1.48 g, 2.50 mmol) in trifluoroacetic acid (20 g) was stirred at room temperature for 24 hours. The solution was then worked-up and the product isolated as described in Part B of Example 21. After the desired product was collected by filtration, it was purified by column chromatography on silica gel (60 g, eluting with 5% to 10% CMA in chloroform) to provide 0.235 g of 1-{[3-(4-fluorophenyl)isoxazol-5-yl]methyl}-2,6,7-trimethyl-1H-imidazo[4,5-c]pyridin-4-amine as a white powder, mp 278.0-279.0° C.

MS (ESI) m/z 352 (M+H)+.

Anal. calcd for $C_{19}H_{18}FN_5O$: C, 64.95; H, 5.16; N, 19.93. Found: C, 64.78; H, 5.05; N, 20.12.

Example 23

1-{[3-(4-Fluorophenyl)isoxazol-5-yl]methyl}-6,7-dimethyl-2-propyl-1H-imidazo[4,5-c]pyridin-4-amine

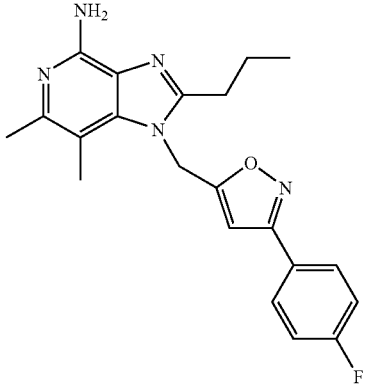

Part A

N⁴-{[3-(4-Fluorophenyl)isoxazol-5-yl]methyl}-N²,N²-bis(4-methoxybenzyl)-5,6-dimethylpyridine-2,3,4-triamine (6.00 g, 10.6 mmol), trimethyl orthobutyrate (2.4 g, 16 mmol), concentrated hydrochloride acid (0.2 mL), and toluene (30 mL) were combined and treated according to the method described in Part E of Example 18 with the modification that no additional trimethyl orthobutyrate was added. 1-{[3-(4-Fluorophenyl)isoxazol-5-yl]methyl}-N,N-bis(4-methoxybenzyl)-6,7-dimethyl-2-propyl-1H-imidazo[4,5-c]pyridin-4-amine (2.62 g) was obtained as a yellow solid.

Part B

Under a nitrogen atmosphere, a solution of 1-{[3-(4-fluorophenyl)isoxazol-5-yl]methyl}-N,N-bis(4-methoxybenzyl)-6,7-dimethyl-2-propyl-1H-imidazo[4,5-c]pyridin-4-amine (2.62 g, 4.23 mmol) in trifluoroacetic acid (25 mL) was stirred at room temperature for 2.7 days. The solution was then worked-up and the product isolated and purified as described in Part B of Example 21 to provide 0.549 g of 1-{[3-(4-fluorophenyl)isoxazol-5-yl]methyl}-6,7-dimethyl-2-propyl-1H-imidazo[4,5-c]pyridin-4-amine as a white powder, mp 227.0-229.0° C.

MS (ESI) m/z 380 (M+H)+.

Anal. calcd for $C_{21}H_{22}FN_5O$: C, 66.48; H, 5.84; N, 18.46. Found: C, 66.46; H, 5.65; N, 18.52.

Example 24

4-Chloro-1-{[3-(4-fluorophenyl)isoxazol-5-yl]methyl}-1H-imidazo[4,5-c]quinoline

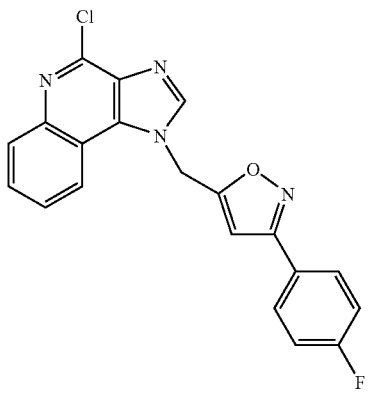

Part A

Under a nitrogen atmosphere, 4-fluoro-N-hydroxybenzenecarboximidoyl chloride (54 g, 230 mmol), prepared as described in Parts A through C of Example 11, was added to a solution of 2-chloro-3-nitro-N-prop-2-ynylquinolin-4-amine (30.2 g, 115 mmol), prepared as described in Part A of Example 3, in dichloromethane (1 L) at room temperature. Triethylamine (26 g, 250 mmol) was added; a precipitate formed. The resulting mixture was heated at 40° C. under nitrogen for 16.5 hours and concentrated under reduced pressure. The resulting solid was dissolved in ethyl acetate, and the work-up and isolation procedures described in Part B of Example 18 were followed to provide 36.12 g of 2-chloro-N-{[3-(4-fluorophenyl)isoxazol-5-yl]methyl}-3-nitroquinolin-4-amine as a yellow solid.

Part B

Under a nitrogen atmosphere, acetonitrile (2 L) was added to a Parr vessel containing 5% platinum on carbon (2.0 g) and 2-chloro-N-{[3-(4-fluorophenyl)isoxazol-5-yl]methyl}-3-nitroquinolin-4-amine (36.12 g, 90.58 mmol). The vessel was sealed, purged with nitrogen, and placed under hydrogen pressure (30 psi, $2.1 \times 10^5$ Pa) for 17 hours at room temperature. The catalyst was removed by filtration, and the filtrate was concentrated under reduced pressure. The resulting semi-solid was treated with diethyl ether, which was removed under reduced pressure to provide 33 g of 2-chloro-N⁴-{[3-(4-fluorophenyl)isoxazol-5-yl]methyl}quinoline-3,4-diamine as a yellow-orange solid. A portion of the material was purified by column chromatography on silica gel (6 g, eluting with 10% ethyl acetate in hexane) to provide 0.0298 g of an analytically pure sample as pale yellow crystals, mp 127-128.0° C.

MS (ESI) m/z 369 (M+H)+.

Anal. calcd for $C_{19}H_{14}ClFN_4O$: C, 61.88; H, 3.83; N, 15.19. Found: C, 61.67; H, 3.88; N, 15.14.

The reaction mixture from a separate reduction carried out in toluene was filtered to remove the catalyst, and the filtrate was used in the next step.

Part C

Pyridine hydrochloride (3 mg, 0.02 mmol) and triethyl orthoformate (0.3 mL, 1.7 mmol) were added to a solution of 2-chloro-N⁴-{[3-(4-fluorophenyl)isoxazol-5-yl]methyl}quinoline-3,4-diamine (0.4294 g, 1.164 mmol) in toluene (10 mL), and the reaction was heated at 110° C. for 16 hours. A solid was present and was isolated by filtration. The filtrate was concentrated under reduced pressure and triturated with diethyl ether to provide a solid. The two solids were combined and purified by column chromatography on silica gel (eluting with 1:1 ethyl acetate:hexane) to provide 0.259 g of 4-chloro-1-{[3-(4-fluorophenyl)isoxazol-5-yl]methyl}-1H-imidazo[4,5-c]quinoline as a white solid, mp 219.0-220.0° C.

MS (ESI) m/z 379 (M+H)+.

Anal. calcd for $C_{20}H_{12}ClFN_4O$: C, 63.42; H, 3.19; N, 14.79. Found: C, 63.49; H, 2.83; N, 14.73.

Example 25

1-{[3-(4-Fluorophenyl)isoxazol-5-yl]methyl}-1H-imidazo[4,5-c]quinolin-4-amine

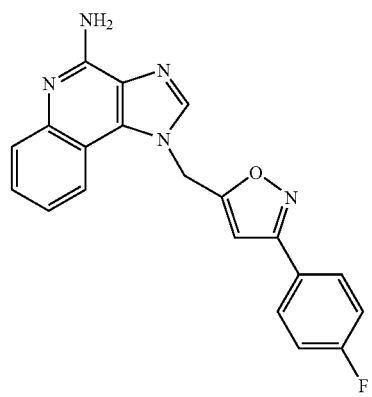

A mixture of 4-chloro-1-{[3-(4-fluorophenyl)isoxazol-5-yl]methyl}-1H-imidazo[4,5-c]quinoline (0.2322 g, 0.6130 mmol) and 7 N ammonia in methanol (10 mL) was sealed in a pressure vessel and heated at 150° C. for 22 hours and allowed to cool to room temperature. The volatiles were removed under reduced pressure, and the resulting orange solid was triturated with diethyl ether. The solid was then purified by column chromatography on silica gel (7 g, eluting with 10% to 20% CMA in chloroform), triturated with diethyl ether, isolated by filtration, and dried. The solid was then boiled in methanol in the presence of a small amount of 0.5 N sodium hydroxide in methanol. The mixture was allowed to cool to room temperature, and the solid was isolated by filtration and dried to provide 0.0259 g of 1-{[3-(4-fluorophenyl)isoxazol-5-yl]methyl}-1H-imidazo[4,5-c]quinolin-4-amine as a tan powder, mp 259.0-260.0° C.

MS (ESI) m/z 360 (M+H)+.

Anal. calcd for $C_{20}H_{14}FN_5O \cdot 0.5H_2O$: C, 65.21; H, 4.10; N, 19.01. Found: C, 64.90; H, 3.87; N, 18.81.

Example 26

2-Ethyl-1-{[3-(4-fluorophenyl)isoxazol-5-yl]methyl}-1H-imidazo[4,5-c]quinolin-4-amine

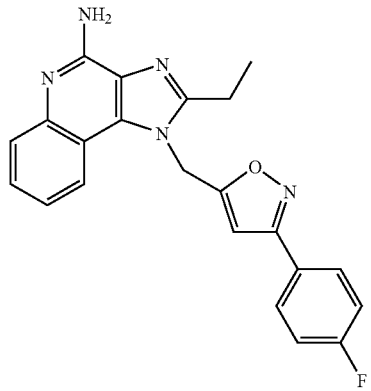

Part A

Under a nitrogen atmosphere, pyridine hydrochloride (0.020 g, 0.19 mmol), triethyl orthopropionate (2.5 g, 14 mmol), 2-chloro-$N^4$-{[3-(4-fluorophenyl)isoxazol-5-yl]methyl}quinoline-3,4-diamine (3.5 g, 9.5 mmol), and toluene (50 mL) were combined and heated at 110° C. for 18 hours. Most of the volatiles were removed under reduced pressure to provide a suspension. The solid was isolated by filtration, washed with diethyl ether, and dried to provide 2.624 g of 4-chloro-2-ethyl-1-{[3-(4-fluorophenyl)isoxazol-5-yl]methyl}-1H-imidazo[4,5-c]quinoline as a tan solid.

Part B

4-Chloro-2-ethyl-1-{[3-(4-fluorophenyl)isoxazol-5-yl]methyl}-1H-imidazo[4,5-c]quinoline (2.624 g, 6.451 mmol), 7 N ammonia in methanol (40 mL), and tetrakis(triphenylphosphine)palladium(0) were combined in a pressure vessel and heated at 120° C. for 16 hours. An analysis by HPLC indicated that the reaction was incomplete. The volatiles were removed under reduced pressure, and the residue was dissolved in chloroform. The solution was washed sequentially with aqueous potassium carbonate, water, and brine; dried over magnesium sulfate; filtered; and concentrated under reduced pressure. The resulting dark yellow solid was added to a pressure vessel with 7 N ammonia in methanol (60 mL), and the reaction was sealed and heated at 150° C. for 18 hours. The volatiles were removed under reduced pressure, and the residue was stirred with 0.5 N potassium hydroxide in methanol for 30 minutes. The resulting solid was isolated by filtration, diluted with dichloromethane, purified by column chromatography on silica gel (eluting with 5% to 10% CMA in chloroform), triturated with diethyl ether and filtered, and recrystallized from acetonitrile after a hot filtration. The crystals were isolated by filtration, washed with diethyl ether, and dried to provide 0.139 g of 2-ethyl-1-{[3-(4-fluorophenyl)isoxazol-5-yl]methyl}-1H-imidazo[4,5-c]quinolin-4-amine as a white powder, mp 232.0-233.0° C.

MS (ESI) m/z 388 (M+H)+.

Anal. calcd for $C_{22}H_{18}FN_5O$: C, 68.21; H, 4.68; N, 18.08. Found: C, 68.16; H, 4.29; N, 18.19.

Example 27

1-{[3-(4-Fluorophenyl)isoxazol-5-yl]methyl}-2-propyl-1H-imidazo[4,5-c]quinolin-4-amine

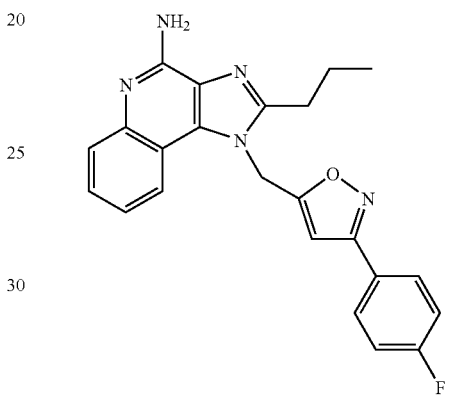

Part A

Under a nitrogen atmosphere, pyridine hydrochloride (0.020 g, 0.19 mmol), trimethyl orthobutyrate (2.1 g, 14 mmol), 2-chloro-$N^4$-{[3-(4-fluorophenyl)isoxazol-5-yl]methyl}quinoline-3,4-diamine (3.5 g, 9.5 mmol), and toluene (50 mL) were combined and heated at 110° C. for 18 hours. The volatiles were removed under reduced pressure. The crude product was purified by column chromatography on silica gel (250 g, eluting with 20% to 40% ethyl acetate in hexane) to provide 0.806 g of 4-chloro-1-{[3-(4-fluorophenyl)isoxazol-5-yl]methyl}-2-propyl-1H-imidazo[4,5-c]quinoline as a yellow solid.

Part B

A mixture of 4-chloro-1-{[3-(4-fluorophenyl)isoxazol-5-yl]methyl}-2-propyl-1H-imidazo[4,5-c]quinoline (0.806 g, 1.92 mmol) and 7 N ammonia in methanol (40 mL) was sealed in a pressure vessel and heated at 150° C. for 18 hours and allowed to cool to room temperature. The volatiles were removed under reduced pressure, and the resulting solid was stirred with 0.5 N sodium hydroxide in methanol. The solid was isolated by filtration, washed with diethyl ether, purified by column chromatography on silica gel (eluting with 5% to 10% CMA in chloroform), triturated with diethyl ether, isolated by filtration, and dried to provide 0.123 g of 1-{[3-(4-fluorophenyl)isoxazol-5-yl]methyl}-2-propyl-1H-imidazo[4,5-c]quinolin-4-amine as a white powder, mp 226.0-227.0° C.

MS (ESI) m/z 401 (M+H)+.

Anal. calcd for $C_{23}H_{20}FN_5O$: C, 68.81; H, 5.02; N, 17.45. Found: C, 68.67; H, 4.92; N, 17.53.

Example 28

1-{[3-(4-Fluorophenyl)isoxazol-5-yl]methyl}-2-methyl-1H-imidazo[4,5-c]quinolin-4-amine

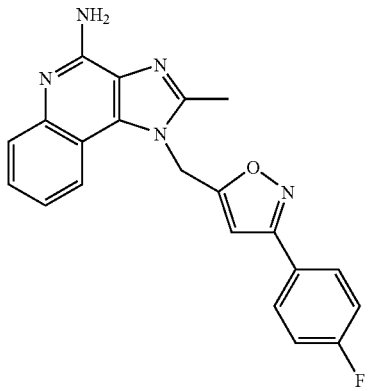

Part A

Pyridine hydrochloride (0.020 g, 0.19 mmol), triethyl orthoacetate (2.3 g, 14 mmol), 2-chloro-$N^4$-{[3-(4-fluorophenyl)isoxazol-5-yl]methyl}quinoline-3,4-diamine (3.5 g, 9.5 mmol), and toluene (50 mL) were combined and treated according to the method of Part A of Example 26 to provide 2.307 g of 4-chloro-1-{[3-(4-fluorophenyl)isoxazol-5-yl]methyl}-2-methyl-1H-imidazo[4,5-c]quinoline as a pale yellow solid.

Part B

4-Chloro-1-{[3-(4-fluorophenyl)isoxazol-5-yl]methyl}-2-methyl-1H-imidazo[4,5-c]quinoline (2.307 g, 5.873 mmol) was treated according to the method described in Part B of Example 27 using 60 mL of 7 N ammonia in methanol. Following the purification steps, the solid product was stirred for 16 hours in 25% potassium hydroxide in ethanol, isolated by filtration, washed with water and isopropyl alcohol, and dried. The resulting white solid was stirred for one hour with 6 N hydrogen chloride in ethanol, and the mixture was then adjusted to pH 14 with the addition of 6 N potassium hydroxide. The solid was isolated by filtration, washed with water and diethyl ether, and dried under high vacuum at 100° C. for 18 hours to provide 1-{[3-(4-fluorophenyl)isoxazol-5-yl]methyl}-2-methyl-1H-imidazo[4,5-c]quinolin-4-amine as a white powder, mp 294.0-296.0° C.

MS (ESI) m/z 374 (M+H)+.

Anal. calcd for $C_{21}H_{16}FN_5O$: C, 67.55; H, 4.32; N, 18.76. Found: C, 67.50; H, 4.28; N, 18.97.

Example 29

4-Chloro-2-(ethoxymethyl)-1-{[3-(4-fluorophenyl)isoxazol-5-yl]methyl}-1H-imidazo[4,5-c]quinoline

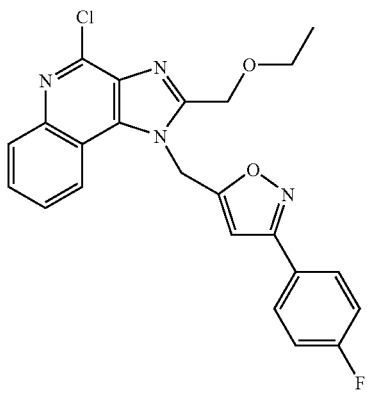

Part A

Under a nitrogen atmosphere, ethoxyacetyl chloride (5.5 g, 45 mmol) was added dropwise to a solution of 2-chloro-$N^4$-{[3-(4-fluorophenyl)isoxazol-5-yl]methyl}quinoline-3,4-diamine (15.00 g, 40.67 mmol) and triethylamine (8.5 mL, 61 mmol) in dichloromethane (200 mL) at 6° C. After the reaction was stirred for 30 minutes, an analysis by HPLC indicated the presence of starting material, and additional ethoxyacetyl chloride (1.01 g) was added. The stirring was continued, and over the course of five hours, a total of 13 g of ethoxyacetyl chloride was added. The work-up procedure described in Part A of Example 19 was followed to provide N-[2-chloro-4-({[3-(4-fluorophenyl)isoxazol-5-yl]methyl}amino)quinolin-3-yl]-2-ethoxyacetamide as an orange solid.

Part B

The material from Part A, pyridine hydrochloride (2.0 g, 2.0 mmol), toluene (500 mL) were combined under a nitrogen atmosphere and heated at 110° C. for 22 hours, allowed to cool to room temperature, and concentrated under reduced pressure. The residue was partitioned between dichloromethane and saturated aqueous potassium carbonate. The aqueous layer was separated and extracted with dichloromethane. The combined organic fractions were washed sequentially with water and brine, dried over magnesium sulfate, and filtered. The volume was reduced to 20 mL by concentration under reduced pressure, and a precipitate formed. The precipitate was isolated by filtration, washed with toluene and diethyl ether, and dried under vacuum to provide 12.6 g of 4-chloro-2-(ethoxymethyl)-1-{[3-(4-fluorophenyl)isoxazol-5-yl]methyl}-1H-imidazo[4,5-c]quinoline. A portion of the product was recrystallized from methanol to provide 0.509 g of an analytically pure sample as tan crystals, mp 189.0-190.0° C.

MS (ESI) m/z 437 (M+H)+.

Anal. calcd for $C_{23}H_{18}ClFN_4O_2$: C, 63.23; H, 4.15; N, 12.82. Found: C, 63.16; H, 4.16; N, 12.81.

Example 30

2-(Ethoxymethyl)-1-{[3-(4-fluorophenyl)isoxazol-5-yl]methyl}-1H-imidazo[4,5-c]quinolin-4-amine

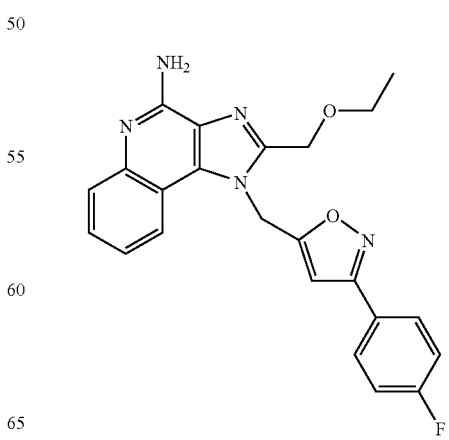

A mixture of 4-chloro-2-(ethoxymethyl)-1-{[3-(4-fluorophenyl)isoxazol-5-yl]methyl}-1H-imidazo[4,5-c]quinoline (3.00 g, 6.87 mmol) and 7 N ammonia in methanol (150 mL) was sealed in a pressure vessel and heated at 150° C. for 18 hours and allowed to cool to room temperature. A precipitate formed and was isolated by filtration, washed with diethyl ether, and dried to provide 1.858 g of product. Half of the material was further dried for three days at 100° C. under high vacuum to provide 0.816 g of 2-(ethoxymethyl)-1-{[3-(4-fluorophenyl)isoxazol-5-yl]methyl}-1H-imidazo[4,5-c]quinolin-4-amine as a white, crystalline solid, mp 203.0-204.0° C.

MS (ESI) m/z 418 (M+H)+.

Anal. calcd for $C_{23}H_{20}FN_5O_2$: C, 66.18; H, 4.83; N, 16.78. Found: C, 66.02; H, 4.67; N, 16.97.

Example 31

(4-Amino-1-{[3-(4-fluorophenyl)isoxazol-5-yl]methyl}-1H-imidazo[4,5-c]quinolin-2-yl)methanol

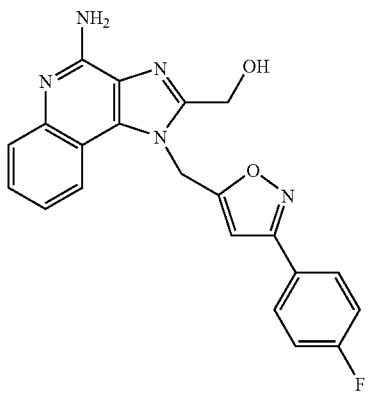

Under a nitrogen atmosphere, a solution of 2-(ethoxymethyl)-1-{[3-(4-fluorophenyl)isoxazol-5-yl]methyl}-1H-imidazo[4,5-c]quinolin-4-amine (0.9923 g, 2.377 mmol) in 1,2-dichloroethane (55 mL) was cooled to about 0° C., and boron tribromide (5.9 mL of a 1 M solution in dichloromethane) was added dropwise. After the reaction was stirred cold for 30 minutes, it was heated at 50° C. for six hours. An analysis by HPLC indicated the reaction was incomplete, and the reaction was again cooled to about 0° C., and additional boron tribromide (1.5 mL) was added dropwise. After the reaction was stirred cold for ten minutes, it was heated at 50° C. for 16 hours. Methanol (30 mL) was added, and the reaction mixture was allowed to cool to room temperature. After 16 hours, the precipitate from the reaction was isolated by filtration and washed sequentially with aqueous potassium hydroxide (30 mL of 1 N), methanol (15 mL), and diethyl ether (15 mL). The solid was then triturated with boiling acetonitrile and isolated by hot filtration to provide 0.161 g of (4-amino-1-{[3-(4-fluorophenyl)isoxazol-5-yl]methyl}-1H-imidazo[4,5-c]quinolin-2-yl)methanol as a white powder, mp 262.0-263.0° C.

MS (ESI) m/z 390 (M+H)+.

Anal. calcd for $C_{21}H_{16}FN_5O_2$: C, 64.78; H, 4.14; N, 17.99. Found: C, 64.53; H, 3.87; N, 18.11.

Example 32

2-(Fluoromethyl)-1-{[3-(4-fluorophenyl)isoxazol-5-yl]methyl}-1H-imidazo[4,5-c]quinolin-4-amine

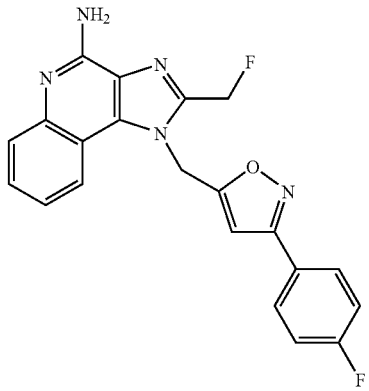

The methods described in Examples 30 and 31 were repeated on a larger scale to provide (4-amino-1-{[3-(4-fluorophenyl)isoxazol-5-yl]methyl}-1H-imidazo[4,5-c]quinolin-2-yl)methanol. The reaction described in Example 31 was heated at reflux and was complete within three hours. Under a nitrogen atmosphere, a suspension of (4-amino-1-{[3-(4-fluorophenyl)isoxazol-5-yl]methyl}-1H-imidazo[4,5-c]quinolin-2-yl)methanol (2.31 g, 5.93 mmol) in dichloromethane (100 mL) was cooled to −78° C. (Diethylamino)sulfur trifluoride (DAST) (0.95 mL, 7.2 mmol) was added dropwise. The mixture was stirred for 30 minutes at −78° C. and then was allowed to warm to room temperature slowly and stirred for one hour. The reaction mixture was diluted with dichloromethane and washed with saturated aqueous potassium carbonate. Additional dichloromethane and water were added to dissolve solids. The aqueous layer was separated and extracted with dichloromethane. The combined organic fractions were washed sequentially with water and brine, dried over sodium sulfate, filtered, and concentrated under reduced pressure. The crude product was purified by column chromatography on silica gel (eluting with 3% to 5% CMA in chloroform) followed by recrystallization from acetonitrile. The crystals were dried under high vacuum for 18 hours at 90° C. to provide 0.994 g of 2-(fluoromethyl)-1-{[3-(4-fluorophenyl)isoxazol-5-yl]methyl}-1H-imidazo[4,5-c]quinolin-4-amine as tan crystals, mp 192.0-193.0° C.

MS (ESI) m/z 392 (M+H)+.

Anal. calcd for $C_{21}H_{15}F_2N_5O$: C, 64.45; H, 3.86; N, 17.89. Found: C, 64.39; H, 3.72; N, 17.93.

Example 33

2-(Ethoxymethyl)-1-{2-[3-(4-fluorophenyl)isoxazol-5-yl]ethyl}-1H-imidazo[4,5-c]quinolin-4-amine

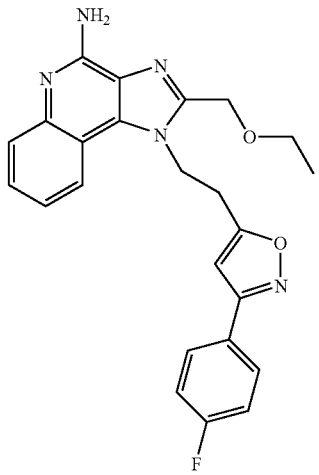

Part A

Under a nitrogen atmosphere, 4-fluoro-N-hydroxybenzenecarboximidoyl chloride (31 g, 180 mmol), prepared as described in Parts A through C of Example 11, was added dropwise to a solution of anhydrous triethylamine (19 mL, 210 mmol) and N-(3-butynyl)phthalimide (19.04 g, 95.58 mmol) in dichloromethane (1 L). The reaction was stirred at room temperature for 24 hours and then diluted with dichloromethane, washed sequentially with aqueous potassium carbonate, water, and brine; dried over potassium sulfate; filtered; and concentrated under reduced pressure. The resulting solid was triturated with ethanol, isolated by filtration, and washed with diethyl ether to provide 29.87 g of 2-{2-[3-(4-fluorophenyl)isoxazol-5-yl]ethyl}-1H-isoindole-1,3(2H)-dione. A portion of the product was recrystallized from isopropyl alcohol and dried to provide an analytically pure sample as white crystals, mp 155.0-156.0° C.

MS (ESI) m/z 337 (M+H)+.

Anal. calcd for $C_{19}H_{13}FN_2O_3$: C, 67.85; H, 3.90; N, 8.33. Found: C, 67.88; H, 3.86; N, 8.33.

Part B

A mixture of 2-{2-[3-(4-fluorophenyl)isoxazol-5-yl]ethyl}-1H-isoindole-1,3(2H)-dione (27.14 g, 80.70 mmol), hydrazine hydrate (9.8 mL, 202 mmol), and ethanol (700 mL) was heated at reflux under nitrogen for two hours. The reaction mixture was filtered to remove a solid, and the filtrate was concentrated under reduced pressure. The resulting oil was dissolved in ethyl acetate, and the solution was washed sequentially with water and brine, dried over sodium sulfate, filtered, and concentrated under reduced pressure to provide 16.14 g of 2-[3-(4-fluorophenyl)isoxazol-5-yl]ethylamine as a colorless oil.

Part C

Under a nitrogen atmosphere, triethylamine (14.9 mL, 107 mmoL) was added to a solution of 2,4-dichloro-3-nitroquinoline (17.29 g, 71.15 mol) in anhydrous 1-methyl-2-pyrrolidinone (NMP) (100 mL). The mixture was stirred until it was homogeneous and then was cooled to 6° C. 2-[3-(4-Fluorophenyl)isoxazol-5-yl]ethylamine (14.9 mL, 107 mmol) was added dropwise over a period of 30 minutes; the temperature did not rise above 10° C. during the addition. After the reaction was stirred for 1.75 hours, deionized water (100 mL) was added. A precipitate formed, and the mixture was stirred for 30 minutes. The precipitate was isolated by filtration, and washed with deionized water until the filtrate was pH 8. The filter cake was then washed sequentially with toluene (100 mL) and a small amount of diethyl ether and dried for 18 hours to provide 27.84 g of 2-chloro-N-{2-[3-(4-fluorophenyl)isoxazol-5-yl]ethyl}-3-nitroquinolin-4-amine as a bright yellow solid.

Part D

Under a nitrogen atmosphere, acetonitrile (1.5 L) was added to a Parr vessel containing 5% platinum on carbon (1.5 g), which had been wet with a small amount of acetonitrile, and 2-chloro-N-{2-[3-(4-fluorophenyl)isoxazol-5-yl]ethyl}-3-nitroquinolin-4-amine (23.20 g, 56.20 mmol). The vessel was sealed, purged three times with hydrogen, and placed under hydrogen pressure (30 psi, $2.1 \times 10^5$ Pa) for 18 hours at room temperature. The catalyst was removed by filtration, and the majority of the filtrate was concentrated under reduced pressure. A solid was present in the remaining filtrate and was isolated by filtration to provide 11.3 g of 2-chloro-$N^4$-{2-[3-(4-fluorophenyl)isoxazol-5-yl]ethyl}quinoline-3,4-diamine as a yellow solid.

Part E

Under a nitrogen atmosphere, ethoxyacetyl chloride (3.5 g, 28 mmol) was added dropwise to a solution of 2-chloro-$N^4$-{2-[3-(4-fluorophenyl)isoxazol-5-yl]ethyl}quinoline-3,4-diamine (9.0 g, 23.5 mmol) and anhydrous triethylamine (10.0 mL, 35.3 mmol) in anhydrous dichloromethane (75 mL) at 6° C. After the reaction was stirred for 30 minutes, an analysis by HPLC indicated the presence of starting material, and additional ethoxyacetyl chloride (2.0 g) was added. After the reaction was stirred for another 30 minutes, it was still incomplete, and additional ethoxyacetyl chloride (2.0 g) was added. The stirring was continued for an additional 30 minutes, and the work-up procedure described in Part A of Example 19 was followed to provide 11.12 g of N-[2-chloro-4-({2-[3-(4-fluorophenyl)isoxazol-5-yl]ethyl}amino)quinolin-3-yl]-2-ethoxyacetamide as a white solid.

Part F

A mixture of N-[2-chloro-4-({2-[3-(4-fluorophenyl)isoxazol-5-yl]ethyl}amino)quinolin-3-yl]-2-ethoxyacetamide (0.500 g, 1.07 mmol) and 7 N ammonia in methanol (7 mL) was sealed in a pressure vessel and heated at 150° C. for 12 hours and allowed to cool to room temperature. The reaction mixture was diluted in dichloromethane, and the resulting solution was washed sequentially with aqueous potassium carbonate, water, and brine; dried over sodium sulfate; filtered; and purified by column chromatography on silica gel (40 g, eluting with 5% to 10% CMA in chloroform). The product was then recrystallized from toluene (20 mL), and the crystals were isolated by filtration, washed with toluene, and dried provide 0.139 g of 2-(ethoxymethyl)-1-{2-[3-(4-fluorophenyl)isoxazol-5-yl]ethyl}-1H-imidazo[4,5-c]quinolin-4-amine as a white powder, mp 180.0-181.0° C. MS (ESI) m/z 432 (M+H)+.

Anal. calcd for $C_{24}H_{22}FN_5O_2$: C, 66.81; H, 5.14; N, 16.23. Found: C, 66.56; H, 5.15; N, 16.01.

Example 34

1-{2-[3-(4-Fluorophenyl)isoxazol-5-yl]ethyl}-2-propyl-1H-imidazo[4,5-c]quinolin-4-amine

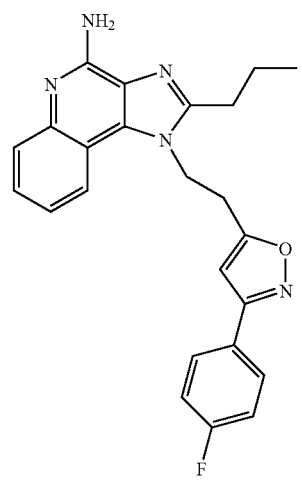

Part A

Under a nitrogen atmosphere, pyridine hydrochloride (1.6 g, 14 mmol), trimethyl orthobutyrate (1.62 g, 11.0 mmol), 2-chloro-$N^4$-{2-[3-(4-fluorophenyl)isoxazol-5-yl]ethyl}quinoline-3,4-diamine (2.10 g, 5.49 mmol), and toluene (50 mL) were combined and heated at reflux for four hours under a Dean-Stark trap. The volatiles were removed under reduced pressure. The resulting oil was dissolved in ethyl acetate, and the solution was washed sequentially with aqueous potassium carbonate, water, and brine; dried over sodium sulfate; filtered; and concentrated under reduced pressure. The crude product was purified by column chromatography on silica gel (eluting with 4:6 hexane:ethyl acetate) to provide 1.22 g of 4-chloro-1-{2-[3-(4-fluorophenyl)isoxazol-5-yl]ethyl}-2-propyl-1H-imidazo[4,5-c]quinoline as a pale yellow solid.

Part B

A mixture of 4-chloro-1-{2-[3-(4-fluorophenyl)isoxazol-5-yl]ethyl}-2-propyl-1H-imidazo[4,5-c]quinoline (1.22 g, 2.81 mmol) and 7 N ammonia in methanol (100 mL) was sealed in a pressure vessel and heated at 150° C. for 12 hours and allowed to cool to room temperature. The volatiles were removed under reduced pressure, and the crude product was purified by column chromatography on silica gel (eluting with 10% to 15% CMA in chloroform). The product was then triturated sequentially with toluene and hexane/diethyl ether to provide 0.312 g of 1-{2-[3-(4-fluorophenyl)isoxazol-5-yl]ethyl}-2-propyl-1H-imidazo[4,5-c]quinolin-4-amine as a white powder, mp 208.0-209.0° C.

HRMS (ESI) calcd for $C_{24}H_{22}FN_5O$: 416.1887, found: 416.1909.

Anal. calcd for $C_{24}H_{22}FN_5O$: C, 69.38; H, 5.34; N, 16.86. Found: C, 69.19; H, 5.27; N, 16.84.

Example 35

1-[(5-Butylisoxazol-3-yl)methyl]-1H-imidazo[4,5-c]quinolin-4-amine

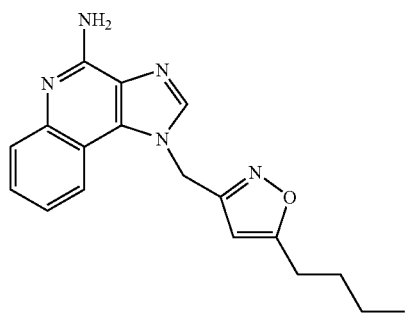

Part A

Water (50 mL) and trifluoroacetic acid (50 mL) were added to a solution of phthalimidoacetaldehyde diethyl acetal (30.0 g, 114 mmol) in chloroform (200 mL), and the reaction mixture was stirred at room temperature for 48 hours. The aqueous layer was separated, adjusted to pH 7 with the addition of sodium carbonate, and extracted with several portions of dichloromethane. The combined organic fractions were dried over magnesium sulfate, filtered, and concentrated under reduced pressure to provide 14.2 g of (1,3-dioxo-1,3-dihydro-2H-isoindol-2-yl)acetaldehyde as a white solid.

Part B

Hydroxylamine hydrochloride (5.74 g, 82.6 mmol) and triethylamine (31.4 mL, 225 mmol) were sequentially added to a solution of (1,3-dioxo-1,3-dihydro-2H-isoindol-2-yl)acetaldehyde (14.2 g, 75.1 mmol) in dichloromethane. The resultant suspension was stirred at room temperature for several hours and adjusted to pH 6 with the addition of saturated aqueous ammonium chloride. The aqueous layer was then separated and extracted with several portions of dichloromethane. The combined organic fractions were dried over magnesium sulfate, filtered, and concentrated under reduced pressure. The residue was purified by chromatography on a vacuum filter funnel (silica gel, eluting with 3% to 5% methanol in dichloromethane). The product was then dissolved in dichloromethane, and the solution was washed with 1 N hydrochloric acid. The aqueous layer was extracted a few times with dichloromethane, and the combined organic fractions were dried over magnesium sulfate, filtered, and concentrated to provide 13.05 g of (1,3-dioxo-1,3-dihydro-2H-isoindol-2-yl)ethanal oxime as a white solid.

Part C

N-Chlorosuccinimide (8.50 g, 63.7 mmol) was added to a solution of (1,3-dioxo-1,3-dihydro-2H-isoindol-2-yl)ethanal oxime (13.0 g, 63.7 mmol) in DMF (100 mL), and the solution was heated at 50° C. gently for two hours and allowed to cool to room temperature. The solution was diluted with ethyl acetate and washed three times with water and once with brine, dried over magnesium sulfate, filtered, and concentrated to provide 15.0 g of 2-(1,3-dioxo-1,3-dihydro-2H-isoindol-2-yl)-N-hydroxyethanimidoyl chloride as a pale yellow solid.

Part D

1-Hexyne (5.16 g, 62.9 mmol) and triethylamine (6.36 g, 62.9 mmol) were sequentially added to a suspension of 2-(1,3-dioxo-1,3-dihydro-2H-isoindol-2-yl)-N-hydroxyethanimidoyl chloride (5.0 g, 21 mmol) in chloroform (80 mL). The solution was stirred overnight at room temperature, washed sequentially with 0.5 M hydrochloric acid and brine, dried over magnesium sulfate, filtered, and concentrated under reduced pressure. The crude product was purified by flash column chromatography on silica gel (eluting with 3:1 to 1:1 hexane:ethyl acetate) to provide 2.14 g of 2-[(5-butylisoxazol-3-yl)methyl]-1H-isoindole-1,3(2H)-dione as a white, crystalline solid.

Part E

A solution of hydrazine hydrate (888 mg, 15.1 mmol) in THF (5 mL) was added to a solution of 2-[(5-butylisoxazol-3-yl)methyl]-1H-isoindole-1,3(2H)-dione (2.14 g, 7.53 mmol) in 2:1 ethanol:THF (60 mL), and the solution was heated at reflux gently for four hours. A precipitate formed and was removed by filtration and washed with THF. The filtrate was concentrated under reduced pressure to provide 1.0 g of (5-butylisoxazol-3-yl)methylamine as a pale yellow solid.

Part F

4-Chloro-3-nitroquinoline (1.35 g, 6.48 mmol) and triethylamine (1.36 mL, 9.73 mmol) were sequentially added to a solution of (5-butylisoxazol-3-yl)methylamine (1.00 g, 6.48 mmol) in dichloromethane, and the solution was stirred for 48 hours at room temperature. The volatiles were removed under reduced pressure, and the residue was purified by flash column chromatography on silica gel (eluting with 3% methanol in dichloromethane) to provide 1.33 g of N-[(5-butylisoxazol-3-yl)methyl]-3-nitroquinolin-4-amine as a yellow, crystalline solid.

Part G

Catalytic 5% platinum on carbon (150 mg) was added to a suspension of N-[(5-butylisoxazol-3-yl)methyl]-3-nitroquinolin-4-amine (1.33 g, 4.08 mmol) in acetonitrile (50 mL), and the mixture was placed under hydrogen pressure (40 psi, $2.8 \times 10^5$ Pa) for six hours. The mixture was filtered through a layer of CELITE filter agent, and the filtrate was concentrated under reduced pressure to provide 1.19 g of $N^4$-[(5-butylisoxazol-3-yl)methyl]quinoline-3,4-diamine.

Part H

Triethyl orthoformate (0.80 mL, 4.80 mmol) and pyridine hydrochloride (0.092 g, 0.80 mmol) were sequentially added to a solution of N⁴-[(5-butylisoxazol-3-yl)methyl]quinoline-3,4-diamine (1.19 g, 4.00 mmol) in acetonitrile (100 mL), and the solution was heated gently at reflux overnight. An analysis by HPLC indicated the presence of starting material, and additional triethyl orthoformate and pyridine hydrochloride were added. The solution was heated at reflux for an additional 24 hours. The solvents were removed under reduced pressure, and the residue was partitioned between dichloromethane and saturated aqueous sodium bicarbonate. The aqueous layer was separated and extracted with dichloromethane, and the combined organic fractions were washed with brine, dried over magnesium sulfate, filtered, and concentrated under reduced pressure. The crude product was purified by flash column chromatography on silica gel (eluting with 3% to 8% methanol in dichloromethane) to provide 1.06 g of 1-[(5-butylisoxazol-3-yl)methyl]-1H-imidazo[4,5-c]quinoline as an orange solid.

Part I mCPBA (930 mg of 77% pure material, 4.2 mmol) was added to a solution of 1-[(5-butylisoxazol-3-yl)methyl]-1H-imidazo[4,5-c]quinoline (1.06 g, 3.46 mmol) in chloroform (40 mL), and the solution was stirred for 1.5 hours at room temperature. p-Toluenesulfonyl chloride (726 g, 3.81 mmol) and concentrated ammonium hydroxide (15 mL) were then added, and the mixture was stirred vigorously for three hours at room temperature. Saturated aqueous sodium bicarbonate was added, and the aqueous layer was separated and extracted several times with chloroform. The combined organic fractions were washed with brine, dried over magnesium sulfate, filtered, and concentrated under reduced pressure. The resulting orange solid was purified by flash column chromatography on silica gel (eluting with 4% to 8% methanol in dichloromethane) to provide 0.92 g of 1-[(5-butylisoxazol-3-yl)methyl]-1H-imidazo[4,5-c]quinolin-4-amine as a tan crystalline solid, mp 201-203° C.

¹H NMR (300 MHz, d₆-DMSO) δ 8.28 (s, 1H), 7.88 (d, J=8.1 Hz, 1H), 7.42 (m, 2H), 7.15 (t, J=8.2 Hz, 1H), 6.75 (br s, 2H), 6.19 (s, 1H), 5.93 (s, 2H), 2.71-2.65 (m, 2H), 1.55-1.49 (m, 2H), 1.28-1.21 (m, 2H), 0.83 (t, J=7.3 Hz, 3H); HRMS (ESI) calcd for $C_{18}H_{19}N_5O$: 322.1668; found: 322.1684.

Example 36

2-Propyl-1-[(5-pyridin-3-ylisoxazol-3-yl)methyl]-1H-imidazo[4,5-c]quinolin-4-amine

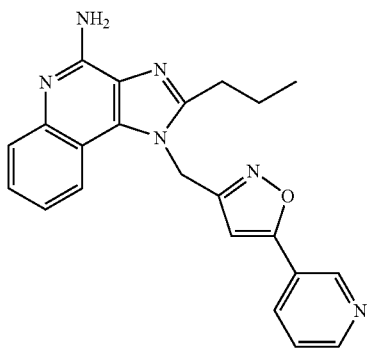

Part A

The method described in Part D of Example 35 was followed using 3-ethynylpyridine (3.24 g, 31.4 mmol) instead of 1-hexyne with the modification that the eluent used for chromatographic purification was a gradient of 3:1 hexane:ethyl acetate to 100% ethyl acetate to 9:1 ethyl acetate:dichloromethane. 2-[(5-Pyridin-3-ylisoxazol-3-yl)methyl]-1H-isoindole-1,3(2H)-dione (2.95 g) was obtained as a yellow solid.

Part B

2-[(5-Pyridin-3-ylisoxazol-3-yl)methyl]-1H-isoindole-1,3(2H)-dione (2.95 g, 9.67 mmol) was treated with hydrazine hydrate (1.14 g, 19.3 mmol) according to the method described in Part E of Example 35 to provide (5-pyridin-3-ylisoxazol-3-yl)methylamine as a pale yellow solid.

Part C

4-Chloro-3-nitroquinoline (2.09 g, 9.99 mmol) and triethylamine (2.10 mL, 15.0 mmol) were sequentially added to a solution of (5-pyridin-3-ylisoxazol-3-yl)methylamine (2.09 g, 9.99 mmol) in dichloromethane, and the solution was stirred overnight at room temperature. The resultant red solution was washed sequentially with saturated aqueous sodium bicarbonate and brine, dried over magnesium sulfate, filtered, and concentrated under reduced pressure. The residue was purified by flash column chromatography on silica gel (eluting with 2% to 5% methanol in dichloromethane) to provide 1.17 g of 3-nitro-N-[(5-pyridin-3-ylisoxazol-3-yl)methyl]quinolin-4-amine as a yellow-orange solid.

Part D

3-Nitro-N-[(5-pyridin-3-ylisoxazol-3-yl)methyl]quinolin-4-amine (1.17 g, 3.37 mmol) was hydrogenated in the presence of 5% platinum on carbon (0.120 g) according to the method described in Part G of Example 35 to provide 0.96 g of N⁴-[(5-pyridin-3-ylisoxazol-3-yl)methyl]quinoline-3,4-diamine.

Part E

The methods of Part H of Example 35 were used to treat N⁴-[(5-pyridin-3-ylisoxazol-3-yl)methyl]quinoline-3,4-diamine (0.95 g, 2.98 mmol) with trimethyl orthobutyrate (0.57 mL, 3.6 mmol) and pyridine hydrochloride (0.069 g, 0.60 mmol) and purify the product to provide 0.930 g of 2-propyl-1-[(5-pyridin-3-ylisoxazol-3-yl)methyl]-1H-imidazo[4,5-c]quinoline as a tan solid.

Part F

The methods described in Part I of Example 35 were used to treat 2-propyl-1-[(5-pyridin-3-ylisoxazol-3-yl)methyl]-1H-imidazo[4,5-c]quinoline (0.920 g, 3.00 mmol) with mCPBA (0.808 g of 77% pure material, 3.6 mmol) followed by p-toluenesulfonyl chloride (0.629 g, 3.30 mmol) and concentrated ammonium hydroxide (15 mL) and purify the final product to provide 0.46 g of 2-propyl-1-[(5-pyridin-3-ylisoxazol-3-yl)methyl]-1H-imidazo[4,5-c]quinolin-4-amine as a tan crystalline solid, mp 206-207° C.

¹H NMR (300 MHz, d₆-DMSO) δ 9.06 (d, J=2.2 Hz, 1H), 8.66 (m, 1H), 8.23 (d, J=8.0 Hz, 1H), 7.94 (d, J=8.2 Hz, 1H), 7.65-7.25 (m, 3H), 7.16-7.12 (m, 2H), 6.55 (br s, 2H), 5.98 (s, 2H), 2.93 (t, J=7.4 Hz, 2H), 1.86-1.81 (m, 2H), 1.02 (t, J=7.2 Hz, 3H).

HRMS (ESI) calcd for $C_{22}H_{21}N_6O$: 385.1777; found: 385.1781.

Example 37

2-(Ethoxymethyl)-1-[(5-phenylisoxazol-3-yl)methyl]-1H-imidazo[4,5-c]quinolin-4-amine

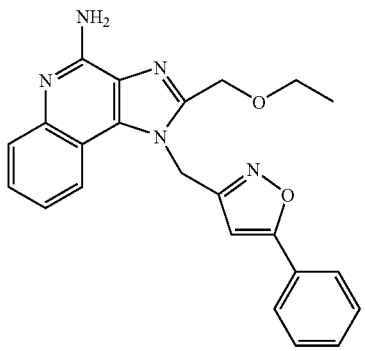

Part A

The methods described in Part D of Example 35 were followed using phenylacetylene (5.35 g, 52.4 mmol) instead of 1-hexyne to provide 3.50 g of 2-[(5-phenylisoxazol-3-yl)methyl]-1H-isoindole-1,3(2H)-dione as a pale yellow, crystalline solid.

Part B

2-[(5-Phenylisoxazol-3-yl)methyl]-1H-isoindole-1,3(2H)-dione (3.48 g, 11.4 mmol) was treated with hydrazine hydrate (1.35 g, 22.9 mmol) according to the method described in Part E of Example 35 to provide (5-phenylisoxazol-3-yl)methylamine as a pale yellow solid.

Part C

A suspension of 4-chloro-3-nitroquinoline (2.29 g, 11.0 mmol) and (5-phenylisoxazol-3-yl)methylamine (1.92 g, 11.0 mmol) in dichloromethane (200 mL) was cooled to 0° C., and triethylamine (2.30 mL, 16.5 mmol) was added. The resultant solution was allowed to warm to room temperature slowly and stirred overnight. The volatiles were removed under reduced pressure, and the residue was purified by flash column chromatography on silica gel (eluting with 3% to 8% methanol in dichloromethane) to provide 2.90 g of 3-nitro-N-[(5-phenylisoxazol-3-yl)methyl]quinolin-4-amine.

Part D

3-Nitro-N-[(5-phenylisoxazol-3-yl)methyl]quinolin-4-amine (2.90 g, 8.37 mmol) was hydrogenated in the presence of 5% platinum on carbon according to the method described in Part G of Example 35 to provide 2.06 g of N-[(5-phenylisoxazol-3-yl)methyl]quinoline-3,4-diamine.

Part E

A solution of ethoxyacetyl chloride (0.87 g, 7.1 mmol) in acetonitrile (10 mL) was added to a solution of $N^4$-[(5-phenylisoxazol-3-yl)methyl]quinoline-3,4-diamine (2.05 g, 6.48 mmol) in acetonitrile (100 mL), and the solution was stirred at room temperature overnight. The volatiles were removed under reduced pressure, and the residue was dissolved in 3:1 ethanol:water (100 mL). Solid sodium hydroxide (389 mg, 9.72 mmol) was added, and the solution was heated at reflux overnight. The ethanol was removed under reduced pressure, and the resultant aqueous solution was adjusted to pH 5 with the additional of dilute hydrochloric acid. The acidic solution was extracted several times with dichloromethane, and the combined organic fractions were washed with brine, dried over magnesium sulfate, filtered, and concentrated under reduced pressure. The crude product was purified by flash column chromatography on silica gel (eluting with 4% to 6% methanol in dichloromethane to provide 0.650 g of 2-(ethoxymethyl)-1-[(5-phenylisoxazol-3-yl)methyl]-1H-imidazo[4,5-c]quinoline as a white solid.

Part F

The methods described in Part I of Example 35 were used to treat 2-(ethoxymethyl)-1-[(5-phenylisoxazol-3-yl)methyl]-1H-imidazo[4,5-c]quinoline (0.650 g, 1.69 mmol) with mCPBA (0.455 g of 77% pure material, 2.0 mmol) followed by p-toluenesulfonyl chloride (0.355 g, 1.86 mmol) and concentrated ammonium hydroxide (15 mL) and purify the final product to provide 0.38 g of 2-(ethoxymethyl)-1-[(5-phenylisoxazol-3-yl)methyl]-1H-imidazo[4,5-c]quinolin-4-amine as a tan crystalline solid, mp 221-223° C.

$^1$H NMR (300 MHz, $d_6$-DMSO) δ 8.01 (d, J=7.4 Hz, 1H), 7.80 (m, 2H), 7.60 (d, J=7.4 Hz, 1H), 7.49 (m, 3H), 7.44 (t, J=8.2 Hz, 1H), 7.15 (t, J=8.2 Hz, 1H), 6.91 (s, 1H), 6.70 (br s, 2H), 6.04 (s, 2H), 4.88 (s, 2H), 3.53 (q, J=7.0 Hz, 2H), 1.02 (t, J=7.0 Hz, 3H). HRMS (ESI) calcd for $C_{23}H_{21}N_5O_2$: 400.1774; found: 400.1784.

Examples 38-65

Part A

The methods described in Examples 30 and 31 were repeated on a larger scale to provide (4-amino-1-{[3-(4-fluorophenyl)isoxazol-5-yl]methyl}-1H-imidazo[4,5-c]quinolin-2-yl)methanol. The reaction described in Example 31 was heated at reflux and was complete within three hours. Thionyl chloride (0.45 mL, 6.17 mmol) was added dropwise to a suspension of (4-amino-1-{[3-(4-fluorophenyl)isoxazol-5-yl]methyl}-1H-imidazo[4,5-c]quinolin-2-yl)methanol (1.2 g, 3.08 mmol) in dichloromethane (30 mL), and the mixture was stirred at room temperature for 1.8 hours. The volatiles were removed under reduced pressure, and the residue was combined with material from another run, triturated with a mixture of ethanol and diethyl ether, and isolated by filtration to provide 1.54 g 2-(chloromethyl)-1-{[3-(4-fluorophenyl)isoxazol-5-yl]methyl}-1H-imidazo[4,5-c]quinolin-4-amine hydrochloride.

Part B

A secondary amine (0.15 mmol, 1.5 equivalents) from the table below was added to a test tube containing 2-(chloromethyl)-1-{[3-(4-fluorophenyl)isoxazol-5-yl]methyl}-1H-imidazo[4,5-c]quinolin-4-amine hydrochloride (44 mg, 0.097 mmol), N,N-diisopropylethylamine (0.057 mL, 0.33 mmol), and N,N-dimethylacetamide (DMA) (1 mL). The test tube was capped and heated overnight at 60° C. The volatiles were removed from each tube by vacuum centrifugation.

The compounds were purified by reversed phase prep HPLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent added to each test tube, the structure of the resulting compound, and the observed accurate mass for the isolated trifluoroacetate salt.

Examples 38-65
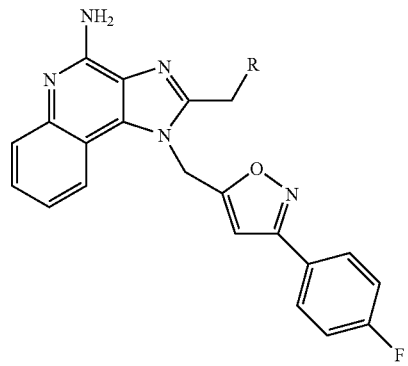
| Example | Reagent | R | Measured Mass (M + H) |
|---|---|---|---|
| 38 | None | Cl | 408.1008 |
| 39 | Pyrrolidine | pyrrolidinyl | 443.1994 |
| 40 | 2-(Methylamino)ethanol | H₃C-N(CH₃)-CH₂CH₂-OH | 447.1921 |
| 41 | Piperidine | piperidinyl | 457.2122 |
| 42 | Morpholine | morpholinyl | 459.1958 |
| 43 | N-Ethyl-N-propylamine | H₃C-N(Et)-CH₂CH₃ | 459.2310 |
| 44 | 2-Ethylaminoethanol | H₃C-N(Et)-CH₂CH₂-OH | 461.2097 |
| 45 | 3-Methylpiperidine | 3-methylpiperidinyl | 471.2268 |
| 46 | 4-Methylpiperidine | 4-methylpiperidinyl | 471.2292 |

-continued

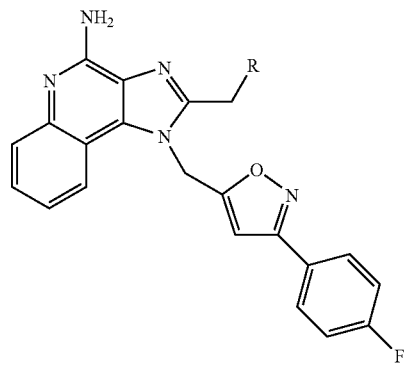

| Example | Reagent | R | Measured Mass (M + H) |
|---|---|---|---|
| 47 | 1-Methylpiperazine | (1-methyl-4-methylpiperazine) | 472.2256 |
| 48 | 3-Hydroxypiperidine | (1-methyl-3-hydroxypiperidine) | 473.2093 |
| 49 | 4-Hydroxypiperidine | (1-methyl-4-hydroxypiperidine) | 473.2111 |
| 50 | 2-(Propylamino)ethanol | (N-propyl-N-(2-hydroxyethyl)amino) | 475.2244 |
| 51 | Diethanolamine | (N,N-bis(2-hydroxyethyl)amino) | 477.2047 |
| 52 | N-Methylaniline | (N-methyl-N-phenylamino) | 479.2035 |
| 53 | 3-(Cyclopropylamino)propionitrile | (N-cyclopropyl-N-(2-cyanoethyl)amino) | 482.2105 |
| 54 | N-Propylcyclopropanemethylamine | (N-propyl-N-(cyclopropylmethyl)amino) | 485.2430 |

-continued

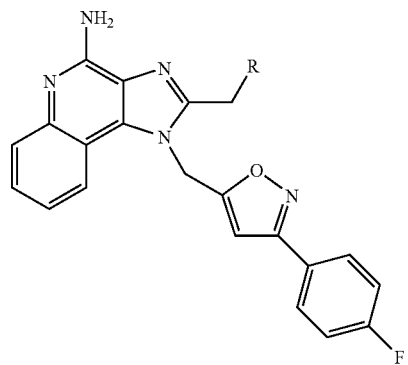

| Example | Reagent | R | Measured Mass (M + H) |
|---|---|---|---|
| 55 | 3-(Dimethylamino)pyrrolidine | (1-methylpyrrolidin-3-yl)-N,N-dimethylamino | 486.2397 |
| 56 | N-Methylhomopiperazine | 4-methyl-1,4-diazepan-1-yl | 486.2385 |
| 57 | 2-Piperidinemethanol | (1-methylpiperidin-2-yl)methanol | 487.2227 |
| 58 | 3-(Hydroxymethyl)piperidine | (1-methylpiperidin-3-yl)methanol | 487.2288 |
| 59 | 4-(Hydroxymethyl)piperidine | (1-methylpiperidin-4-yl)methanol | 487.2223 |
| 60 | N-Methylbenzylamine | N-methyl-N-benzyl | 493.2114 |
| 61 | Isonipecotamide | 1-methylpiperidine-4-carboxamide | 500.2188 |

-continued

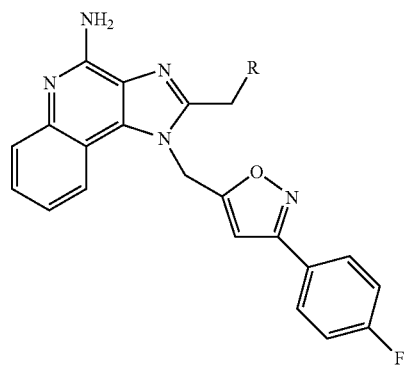

| Example | Reagent | R | Measured Mass (M + H) |
|---|---|---|---|
| 62 | Nipecotamide | 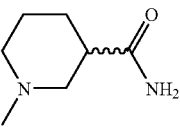 | 500.2159 |
| 63 | 1-Methyl-4-(Methylamino)piperidine |  | 500.2526 |
| 64 | Isonipecotic acid | 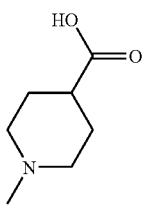 | 501.2057 |
| 65 | Nipecotic acid | 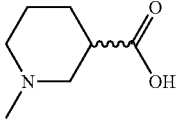 | 501.2013 |

Exemplary Compounds

Certain exemplary compounds, including some of those described above in the examples, have the following Formulas (IIb, IIc, IIIc, IIId, IVc, IVd, Vc, or Vd) and the following R' and R₂ substituents, wherein each line of the table is matched with Formula IIb, IIc, IIIc, IIId, IVc, IVd, Vc, or Vd to represent a specific embodiment of the invention.

IIb

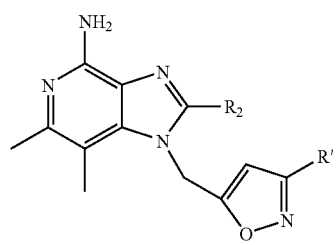

IIc

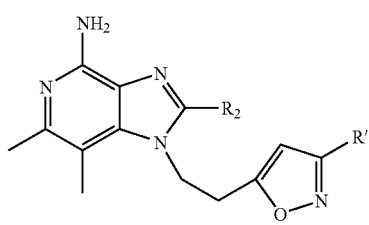

IIIc

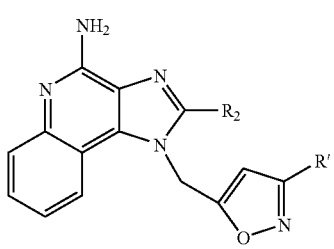

-continued

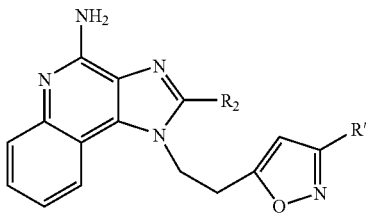

IIId

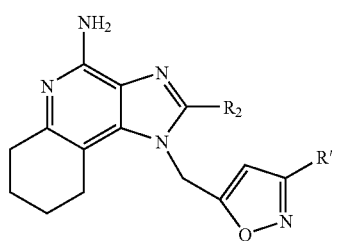

IVc

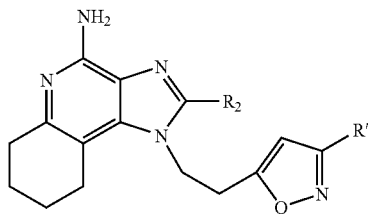

IVd

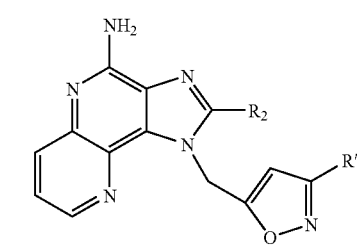

Vc

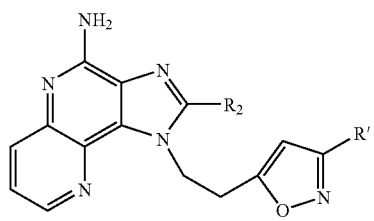

Vd

| R' | R₂ |
|---|---|
| methyl | hydrogen |
| phenyl | hydrogen |
| 4-fluorophenyl | hydrogen |
| pyridin-3-yl | hydrogen |
| methyl | methyl |
| phenyl | methyl |
| 4-fluorophenyl | methyl |
| pyridin-3-yl | methyl |
| methyl | ethyl |
| phenyl | ethyl |
| 4-fluorophenyl | ethyl |
| pyridin-3-yl | ethyl |
| methyl | n-propyl |
| phenyl | n-propyl |
| 4-fluorophenyl | n-propyl |
| pyridin-3-yl | n-propyl |
| methyl | ethoxymethyl |
| phenyl | ethoxymethyl |
| 4-fluorophenyl | ethoxymethyl |

-continued

| R' | R₂ |
|---|---|
| pyridin-3-yl | ethoxymethyl |
| methyl | hydroxymethyl |
| phenyl | hydroxymethyl |
| 4-fluorophenyl | hydroxymethyl |
| pyridin-3-yl | hydroxymethyl |
| methyl | 2-hydroxyethyl |
| phenyl | 2-hydroxyethyl |
| 4-fluorophenyl | 2-hydroxyethyl |
| pyridin-3-yl | 2-hydroxyethyl |
| methyl | fluoromethyl |
| phenyl | fluoromethyl |
| 4-fluorophenyl | fluoromethyl |
| pyridin-3-yl | fluoromethyl |

Certain exemplary compounds, including some of those described above in the Examples, have the following Formulas (IId, IIIe, IVe, or Ve) and the following R' and R₂ substituents, wherein each line of the table is matched with Formula IId, IIIe, IVe, or Ve to represent a specific embodiment of the invention.

IId

IIIe

IVe

Ve

| R' | R₂ |
|---|---|
| butyl | hydrogen |
| phenyl | hydrogen |

-continued

| | |
|---|---|
| 4-fluorophenyl | hydrogen |
| pyridin-3-yl | hydrogen |
| butyl | methyl |
| phenyl | methyl |
| 4-fluorophenyl | methyl |
| pyridin-3-yl | methyl |
| butyl | ethyl |
| phenyl | ethyl |
| 4-fluorophenyl | ethyl |
| pyridin-3-yl | ethyl |
| butyl | n-propyl |
| phenyl | n-propyl |
| 4-fluorophenyl | n-propyl |
| pyridin-3-yl | n-propyl |
| butyl | ethoxymethyl |
| phenyl | ethoxymethyl |
| 4-fluorophenyl | ethoxymethyl |
| pyridin-3-yl | ethoxymethyl |
| butyl | hydroxymethyl |
| phenyl | hydroxymethyl |
| 4-fluorophenyl | hydroxymethyl |
| pyridin-3-yl | hydroxymethyl |
| butyl | 2-hydroxyethyl |
| phenyl | 2-hydroxyethyl |
| 4-fluorophenyl | 2-hydroxyethyl |
| pyridin-3-yl | 2-hydroxyethyl |
| butyl | fluoromethyl |
| phenyl | fluoromethyl |
| 4-fluorophenyl | fluoromethyl |
| pyridin-3-yl | fluoromethyl |

Compounds of the invention have been found to induce cytokine biosynthesis when tested using the methods described below.

Cytokine Induction in Human Cells

An in vitro human blood cell system is used to assess cytokine induction. Activity is based on the measurement of interferon ($\alpha$) and tumor necrosis factor ($\alpha$) (IFN-$\alpha$ and TNF-$\alpha$, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 $\mu$M. Controls include cell samples with media only, cell samples with DMSO only (no compound), and cell samples with reference compound.

Incubation

The solution of test compound is added at 60 $\mu$M to the first well containing RPMI complete and serial 3 fold dilutions are made in the wells. The PBMC suspension is then added to the wells in an equal volume, bringing the test compound concentrations to the desired range (usually 30-0.014 $\mu$M). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-$\alpha$ by ELISA and for TNF-$\alpha$ by IGEN/BioVeris Assay.

Interferon ($\alpha$) and Tumor Necrosis Factor ($\alpha$) Analysis

IFN-$\alpha$ concentration is determined with a human multi-subtype colorimetric sandwich ELISA (Catalog Number 41105) from PBL Biomedical Laboratories, Piscataway, N.J. Results are expressed in pg/mL.

The TNF-$\alpha$ concentration is determined by ORIGEN M-Series Immunoassay and read on an IGEN M-8 analyzer from BioVeris Corporation, formerly known as IGEN International, Gaithersburg, Md. The immunoassay uses a human TNF-$\alpha$ capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-$\alpha$ and IFN-$\alpha$ (y-axis) as a function of compound concentration (x-axis).

Analysis of the data has two steps. First, the greater of the mean DMSO (DMSO control wells) or the experimental background (usually 20 pg/mL for IFN-$\alpha$ and 40 pg/mL for TNF-$\alpha$) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-$\alpha,\alpha$-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration ($\mu$molar) is the lowest of the tested compound concentrations that induces a response over a fixed cytokine concentration for the tested cytokine (usually 20 pg/mL for IFN-$\alpha$ and 40 pg/mL for TNF-$\alpha$). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of the Formula III:

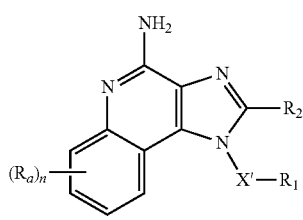

wherein:
X' is selected from the group consisting of —CH(R$_9$)—, —CH(R$_9$)-alkylene-, and —CH(R$_9$)-alkenylene-;
R$_1$ is selected from the group consisting of:

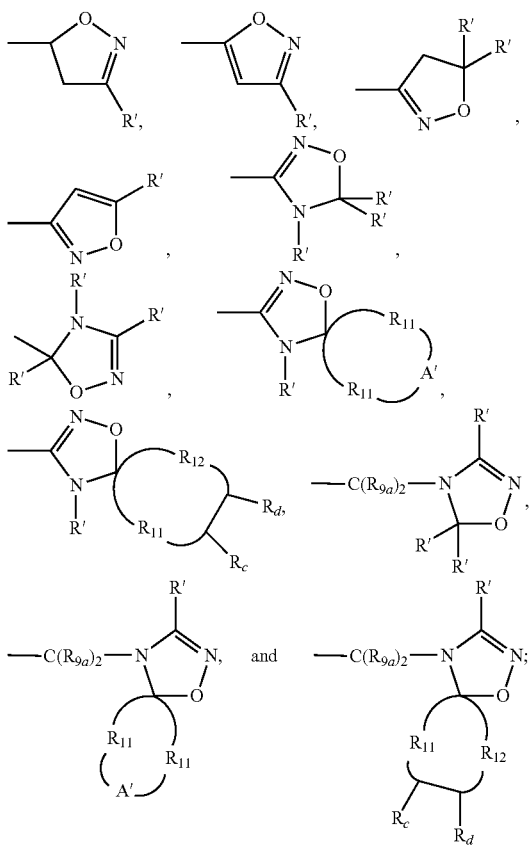

R' is selected from the group consisting of:
  hydrogen,
  alkyl,
  alkenyl,
  aryl,
  arylalkylenyl,
  heteroaryl,
  heteroarylalkylenyl,
  heterocyclyl,
  heterocyclylalkylenyl, and
  alkyl, alkenyl, aryl, arylalkylenyl, heteroaryl, heteroarylalkylenyl, heterocyclyl, or heterocyclylalkylenyl, substituted by one or more substituents selected from the group consisting of:
    hydroxy,
    alkyl,
    haloalkyl,
    hydroxyalkyl,
    alkoxy,
    dialkylamino,
    —S(O)$_{0-2}$-alkyl,
    —S(O)$_{0-2}$-aryl,
    —NH—S(O)$_2$-alkyl,
    —NH—S(O)$_2$-aryl,
    haloalkoxy,
    halogen,
    nitrile,
    nitro
    aryl,
    heteroaryl,
    heterocyclyl,
    aryloxy,
    arylalkyleneoxy,
    —C(O)—O-alkyl,
    —C(O)—N(R$_8$)$_2$,
    —N(R$_8$)—C(O)-alkyl,
    —O—(CO)-alkyl, and
    —C(O)-alkyl;
R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;
R$_{11}$ is C$_{1-6}$ alkylene or C$_{2-6}$ alkenylene, wherein the alkylene or alkenylene is optionally interrupted by one heteroatom;
R$_{12}$ is selected from the group consisting of a bond, C$_{1-5}$ alkylene, and C$_{2-5}$ alkenylene, wherein the alkylene or alkenylene is optionally interrupted by one heteroatom;
  wherein the total number of atoms in the ring which includes R$_{11}$ or R$_{12}$ is 4 to 9;
A' is selected from the group consisting of —O—, —S(O)$_{0-2}$—, —N(-Q-R$_4$)—, and —C(R$_{9a}$)$_2$—;
R$_a$ is selected from the group consisting of halogen, alkyl, haloalkyl, alkoxy, and —N(R$_9$)$_2$;
n is an integer from 0 to 4;
R$_2$ is selected from the group consisting of:
  —R$_4$,
  —X—R$_4$,
  —X—Y—R$_4$, and
  —X—R$_5$;
X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;
Y is selected from the group consisting of:
  —S(O)$_{0-2}$—,
  —S(O)$_2$—N(R$_8$)—,
  —C(R$_6$)—,
  —C(R$_6$)—O—,
  —O—C(R$_6$)—,
  —O—C(O)—O—,
  —N(R$_8$)-Q-,

—C(R$_6$)—N(R$_8$)—,
—O—C(R$_6$)—N(R$_8$)—,
—C(R$_6$)—N(OR$_9$)—,

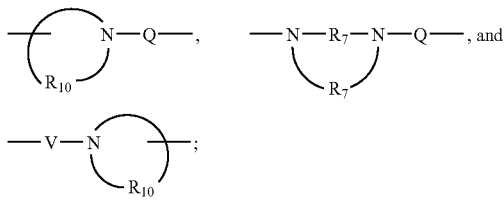

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, arlkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_5$ is selected from the group consisting of:

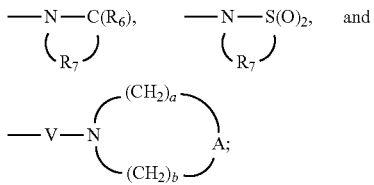

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, and arylalkylenyl;
R$_9$ is selected from the group consisting of hydrogen and alkyl;
R$_{9a}$ is selected from the group consisting of hydrogen and C$_{1-4}$ alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, and S(O)$_2$—N(R$_8$)—;
V is selected from the group consisting of —C(R$_6$)—, —O—C(R$_6$)—, and —S(O)$_2$—; and a and b are each independently an integer from 1 to 6 with the proviso that a+b is ≦7; or a pharmaceutically acceptable salt thereof.

2. The compound or salt of claim 1 wherein n is 0.
3. The compound or salt of claim 1 wherein X' is C$_{1-4}$ alkylene.
4. The compound or salt of claim 1 wherein R$_1$ is selected from the group consisting of:

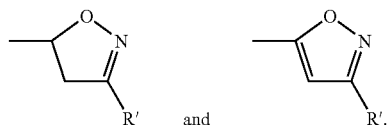

5. The compound or salt of claim 1 wherein R$_1$ is

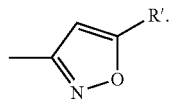

6. The compound or salt of claim 1 wherein R' is selected from the group consisting of methyl; butyl; phenyl which is unsubstituted or substituted by one or more substituents selected from the group consisting of fluorine and trifluoromethyl; and 3-pyridyl.
7. The compound or salt of claim 1 wherein R$_2$ is hydrogen; alkoxyalkylenyl; hydroxyalkylenyl; haloalkylenyl; heterocyclyalkylenyl that is unsubstituted or substituted by one or more substituents selected from the group consisting of methyl, hydroxyl, hydroxymethyl, and dimethylamino; —R$_4$; —X—R$_4$; or —Y—Y—R$_4$; wherein:
X is C$_{1-2}$ alkylene optionally terminated by heterocyclylene;
Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, or —C(R$_6$)—N(OR$_9$)—; wherein
R$_8$ is selected from the group consisting of hydrogen, alkyl, arylalkylenyl, and hydroxyalkylenyl; and
R$_4$ is alkyl that is unsubstituted or substituted by one or more substituents selected from the group consisting of hydroxy; cyano; aryl; or heterocyclyl that is unsubstituted or substituted by alkyl with the proviso that when Y is —C(R$_6$)—O— or —C(R$_6$)—N(R$_8$)—, then R$_4$ may also be hydrogen.
8. The compound or salt of claim 1 wherein R$_2$ is hydrogen, C$_{1-4}$ alkyl, C$_{1-4}$ alkyl-O—C$_{1-4}$ alkylenyl, or hydroxyC$_{1-4}$ alkylenyl.
9. A pharmaceutical composition comprising a therapeutically effective amount of a compound or salt of claim 1 and a pharmaceutically acceptable carrier.

* * * * *